US012290531B2

(12) United States Patent
Curley et al.

(10) Patent No.: US 12,290,531 B2
(45) Date of Patent: May 6, 2025

(54) COMPOSITIONS TARGETING BCMA AND METHODS OF USE THEREOF

(71) Applicant: Takeda Pharmaceutical Company Limited, Osaka (JP)

(72) Inventors: Michael Curley, Cambridge, MA (US); Ertan Eryilmaz, Cambridge, MA (US); Shawn Jennings, Cambridge, MA (US); LeeAnn Talarico, Cambridge, MA (US); Taylor Hickman, Cambridge, MA (US); Christina Sheau Fen Wong, Cambridge, MA (US); Kathryn Fraser, Cambridge, MA (US); Haiqing Wang, Cambridge, MA (US); Alessandra Piersigilli, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 18/640,982

(22) Filed: Apr. 19, 2024

(65) Prior Publication Data

US 2024/0350544 A1 Oct. 24, 2024

Related U.S. Application Data

(63) Continuation of application No. PCT/JP2022/040573, filed on Oct. 19, 2022.

(60) Provisional application No. 63/257,822, filed on Oct. 20, 2021, provisional application No. 63/257,846, filed on Oct. 20, 2021.

(51) Int. Cl.
| | |
|---|---|
| *A61K 35/17* | (2015.01) |
| *A61K 39/00* | (2006.01) |
| *A61K 47/20* | (2006.01) |
| *A61K 47/26* | (2006.01) |
| *A61K 47/42* | (2017.01) |
| *A61P 35/02* | (2006.01) |
| *C07K 16/28* | (2006.01) |

(52) U.S. Cl.
CPC .......... *A61K 35/17* (2013.01); *A61K 39/4613* (2023.05); *A61K 39/4631* (2023.05); *A61K 39/464416* (2023.05); *A61K 47/20* (2013.01); *A61K 47/26* (2013.01); *A61K 47/42* (2013.01); *A61P 35/02* (2018.01); *C07K 16/2878* (2013.01); *A61K 2239/13* (2023.05); *A61K 2239/21* (2023.05); *A61K 2239/25* (2023.05); *A61K 2239/48* (2023.05); *C07K 2317/565* (2013.01)

(58) Field of Classification Search
CPC ........................ A61K 39/4631; A61K 2239/13
See application file for complete search history.

(56) References Cited

U.S. PATENT DOCUMENTS

2019/0144515 A1    5/2019  Sievers et al.

FOREIGN PATENT DOCUMENTS

| WO | WO-2018026819 A2 * | 2/2018 | ............. A61K 35/17 |
|---|---|---|---|
| WO | 2018/237006 A1 | 12/2018 | |
| WO | 2021/160133 A1 | 8/2021 | |

OTHER PUBLICATIONS

International Preliminary Report on Patentability, Ch. I for International Patent Application No. PCT/JP2022/040573 dated Apr. 23, 2024 (16 pages).
International Search Report for International Patent Application No. PCT/JP2022/040573 dated Jun. 5, 2023 (9 pages).
Chmielewski, et al., "Trucks, the fourth-generation CAR T cells: Current developments and clinical translation", Advances in Cell and Gene Therapy 3(3): 2020 (10 pages).
Fujiwara, et al., "Hinge and Transmembrane Domains of Chimeric Antigen Receptor Regulate Receptor Expression and Signaling Threshold", Cells, vol. 9, No. 5, 2020, 1-17, DOI: 10.3390. cells 9051182 (17 pages).
Muller, et al., "The CD28-Transmembrane Domain Mediates Chimeric Antigen Receptor Heterodimerization with CD28", Frontiers in Immunology 12: 639818, 2021 (14 pages).
Roex, et al., "Safety and clinical efficacy of BCMA CAR-T-cell therapy in multiple myeloma", J. Hermatol. & Oncol. 13(1): 2020 (14 pages).
Teoh, et al., "CAR T-cell therapy in multiple myeloma: more room for improvement", Blood Cancer Journal 11(4): 84, 2021 (18 pages).

* cited by examiner

*Primary Examiner* — Meera Natarajan
*Assistant Examiner* — Francesca Edgingtongiordano
(74) *Attorney, Agent, or Firm* — Proskauer Rose LLP

(57) ABSTRACT

This present invention relates to BCMA binders (e.g. antibodies) and chimeric antigen receptor (CAR) constructs comprising a BCMA antigen binding molecule. The BCMA binders specifically bind to BCMA. The present BCMA CARs further comprise a hinge region (e.g., CD28 hinge), a transmembrane domain, and one or more intracellular NK cell signalling domains. NK cells expressing a BCMA CAR has increased efficacy in killing cancer cells. Provided herein also include therapeutic uses of the BCMA binders and BCMA CARs.

6 Claims, 22 Drawing Sheets

Specification includes a Sequence Listing.

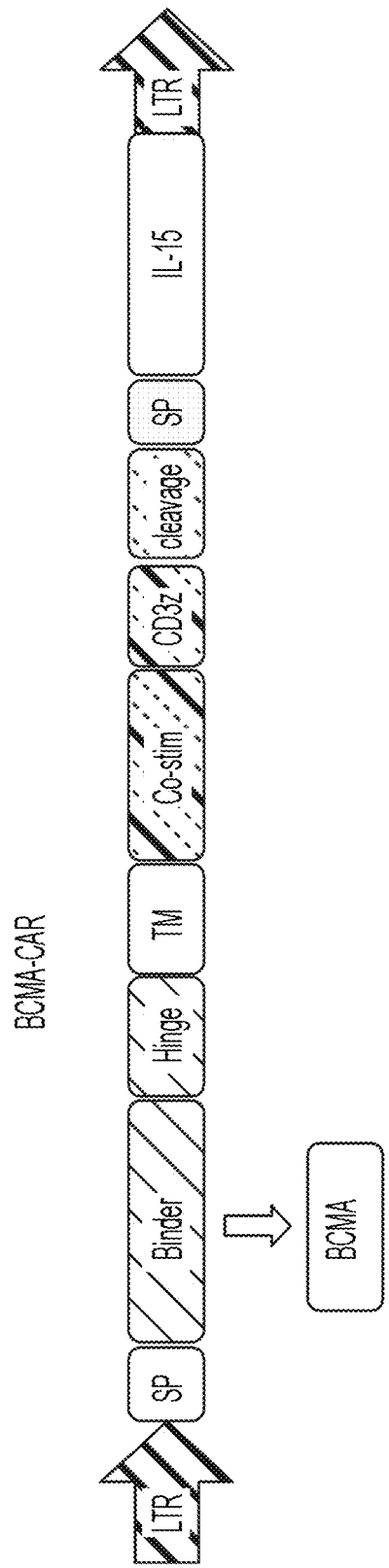
[Fig. 1]

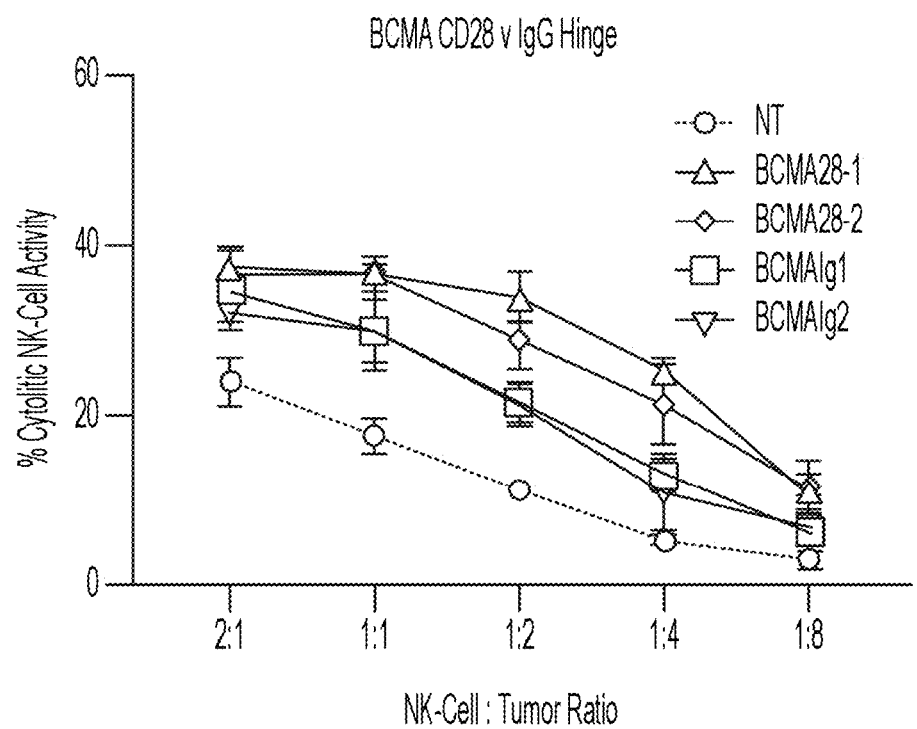
[Fig. 2]

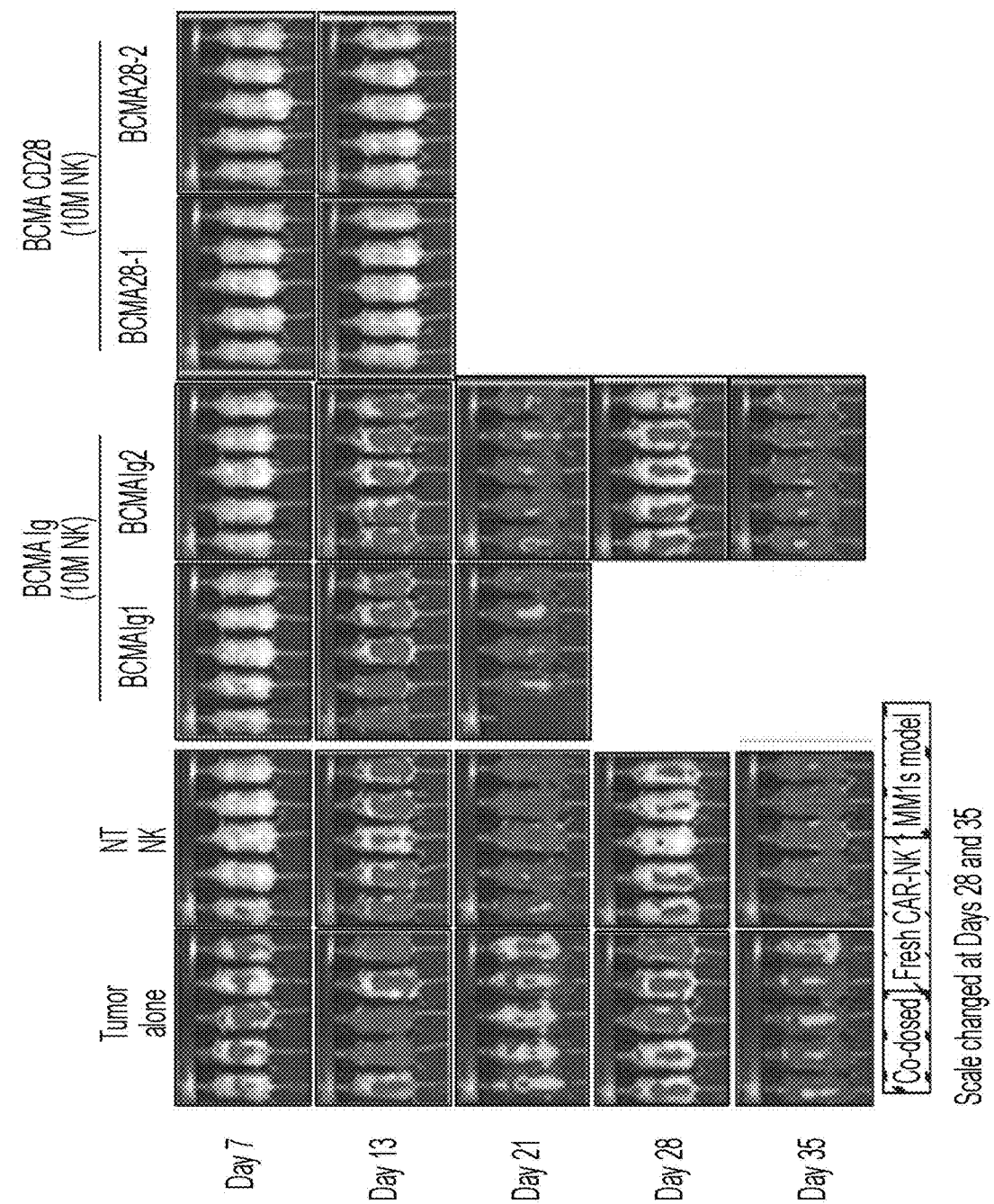
[Fig. 3]

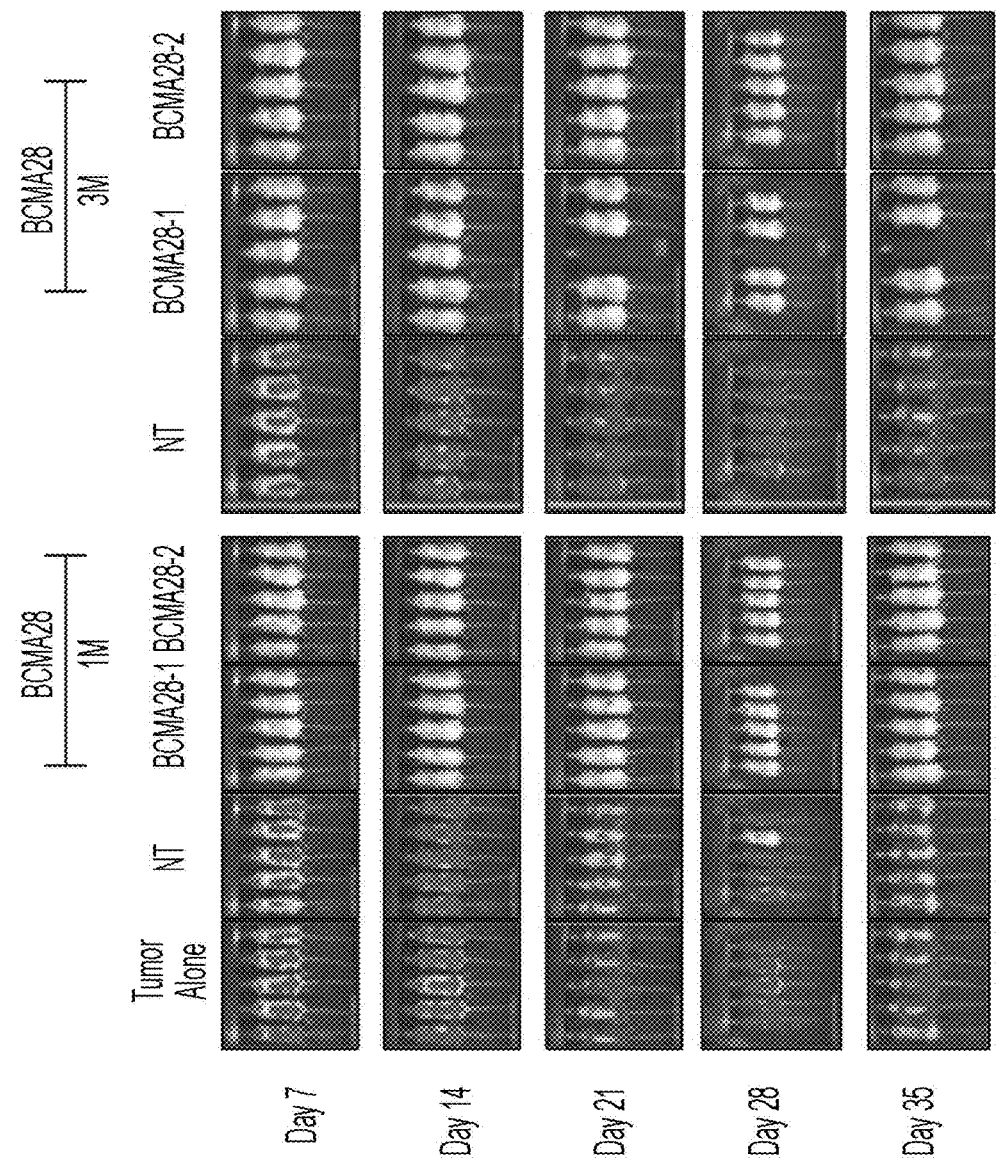
[Fig. 4]

[Fig. 5]
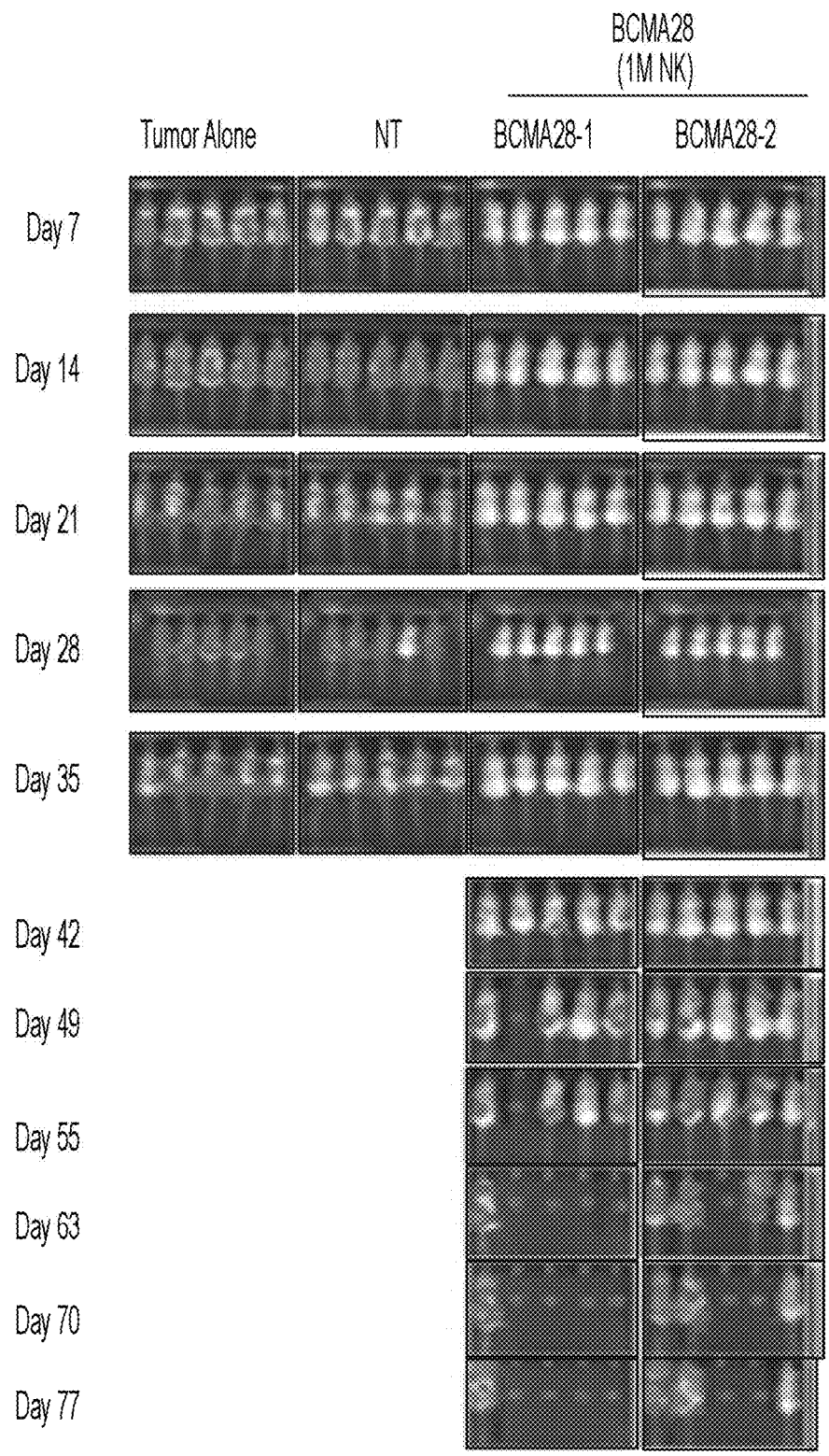
* Deaths related to toxicity/tumor burden

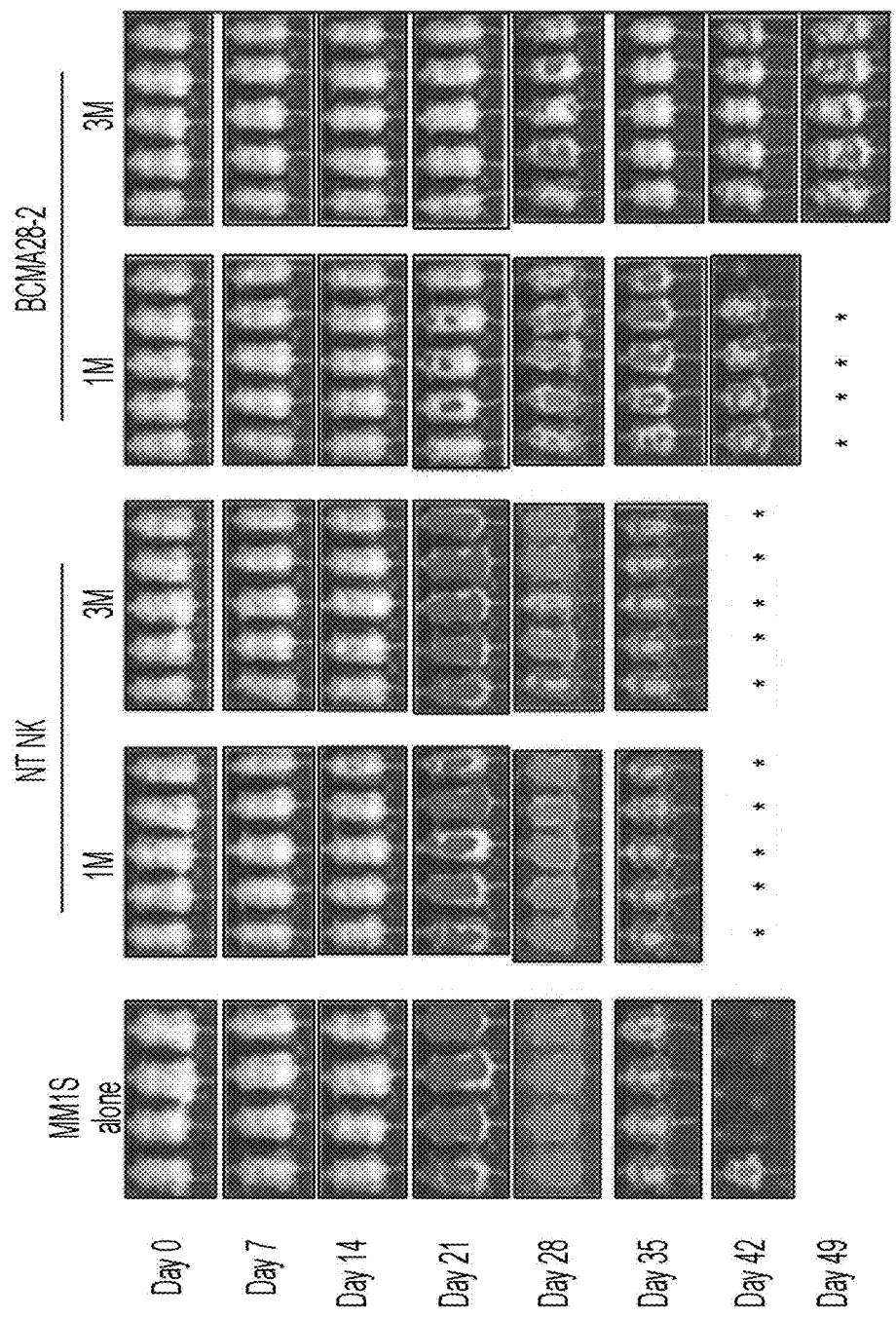
[Fig. 6]

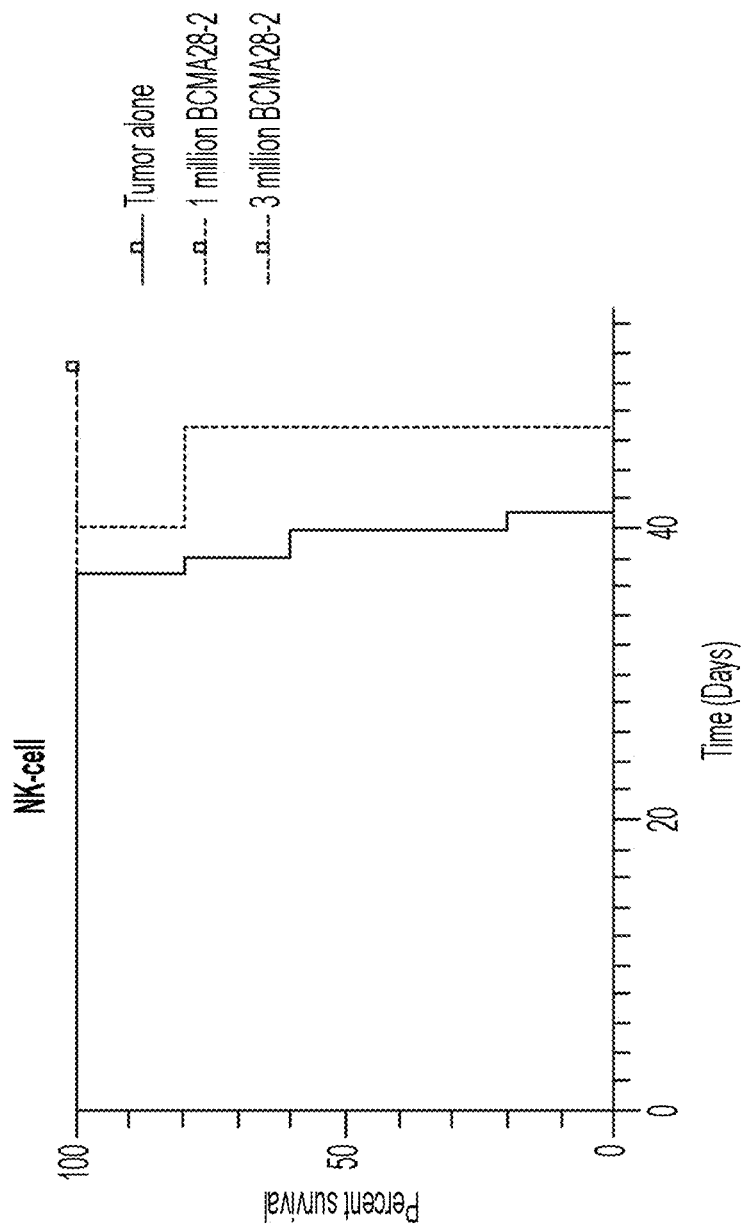
[Fig. 7]

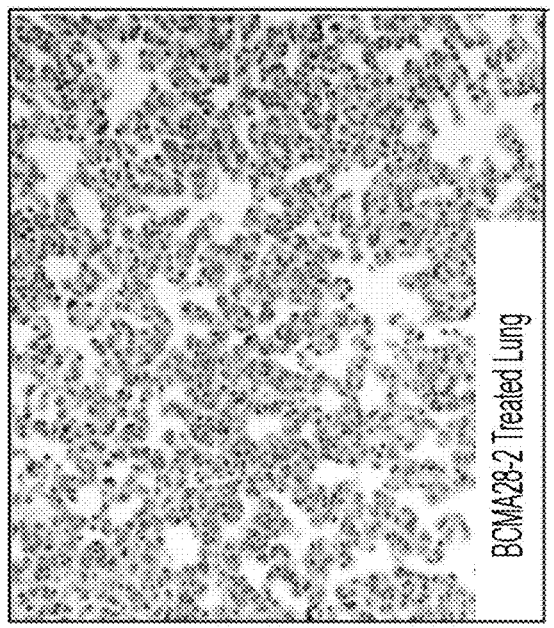
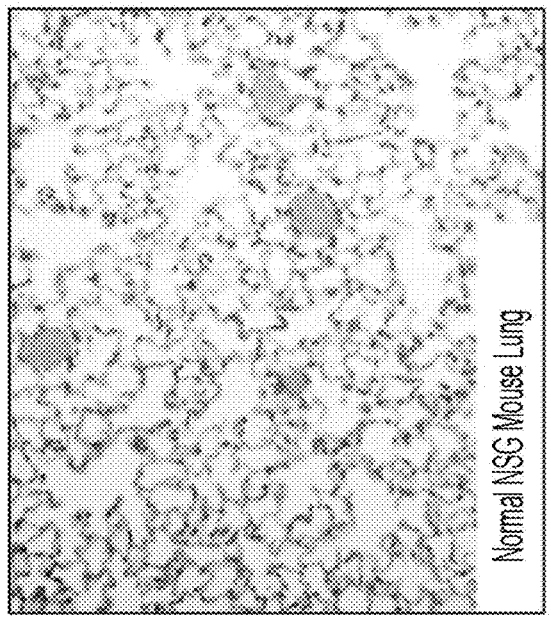
[Fig. 8]

[Fig. 9A]
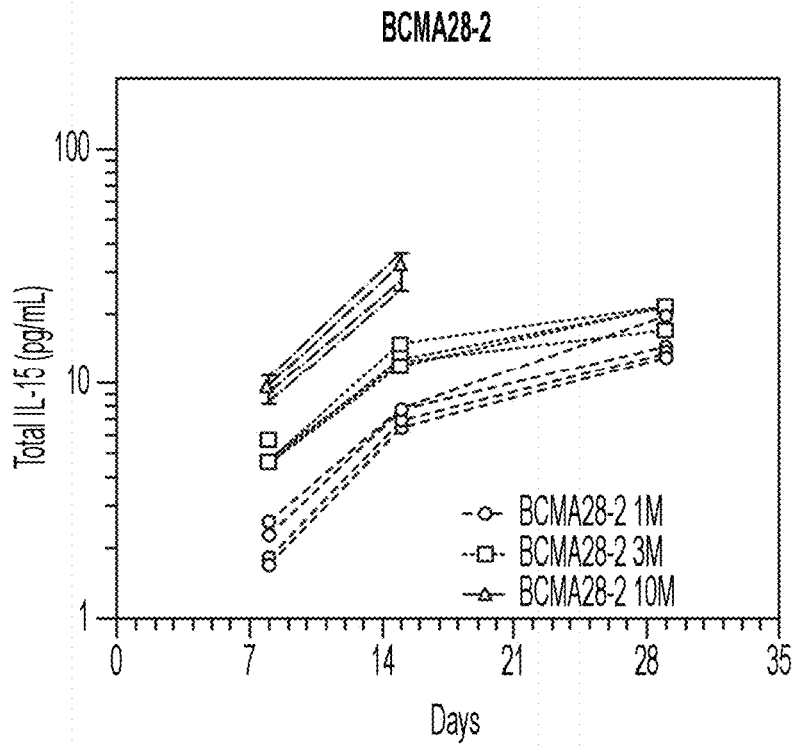
[Fig. 9B]
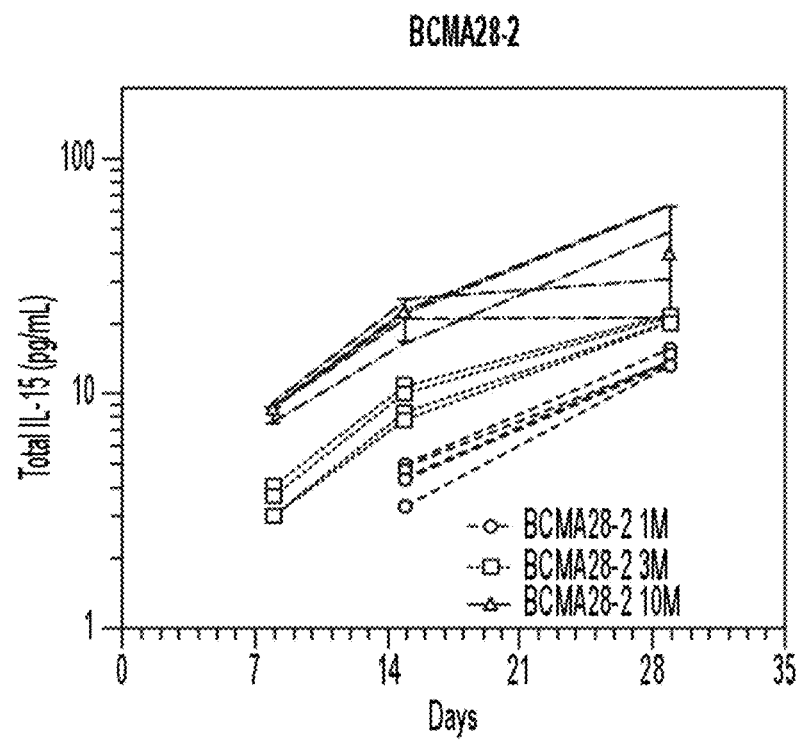

[Fig. 9C]
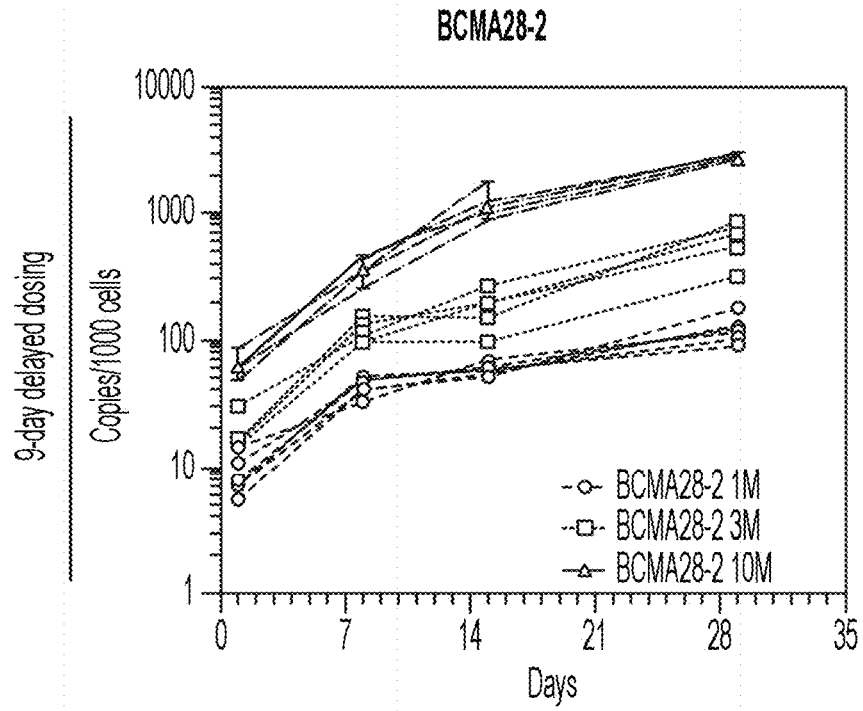
[Fig. 9D]
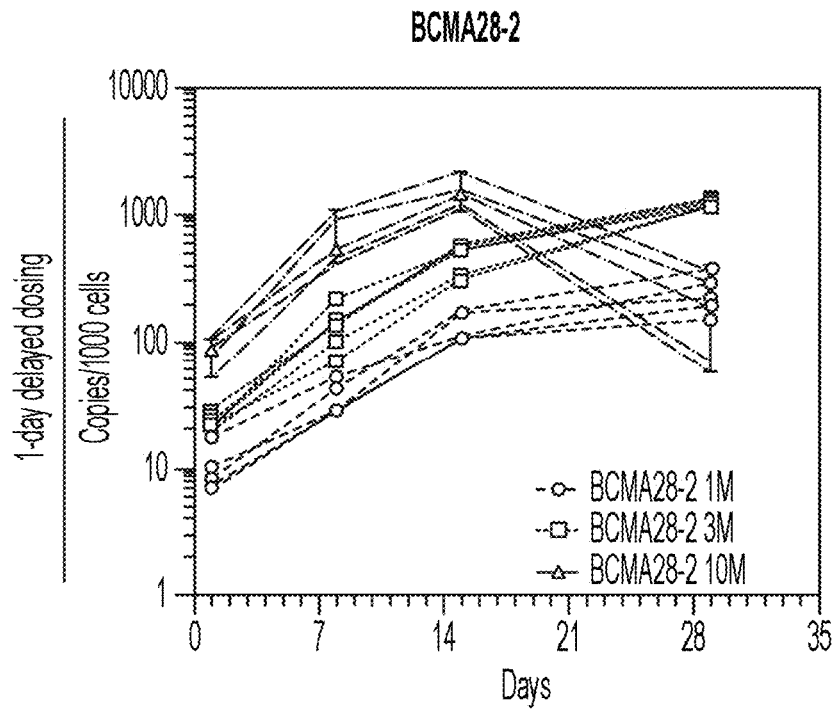

[Fig. 10A]
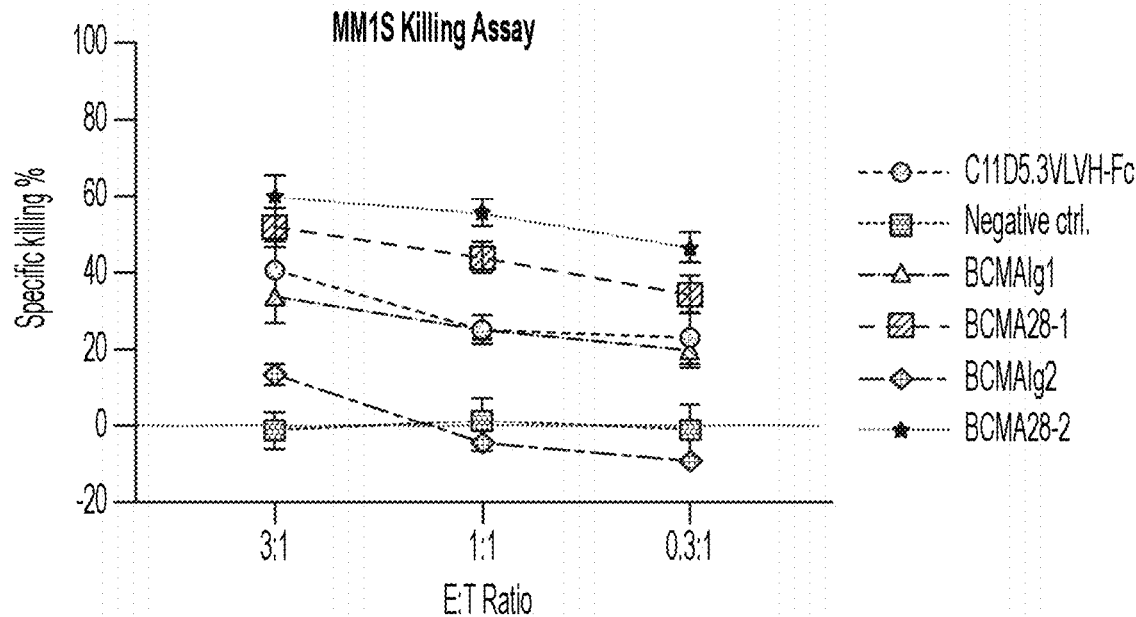
[Fig. 10B]
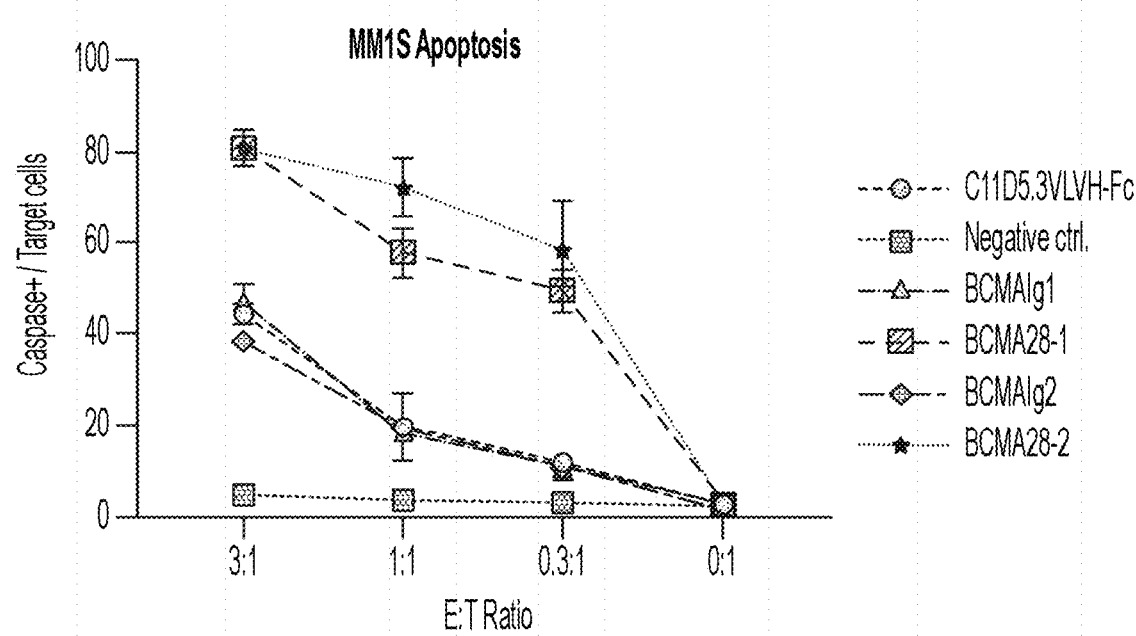

[Fig. 10C]
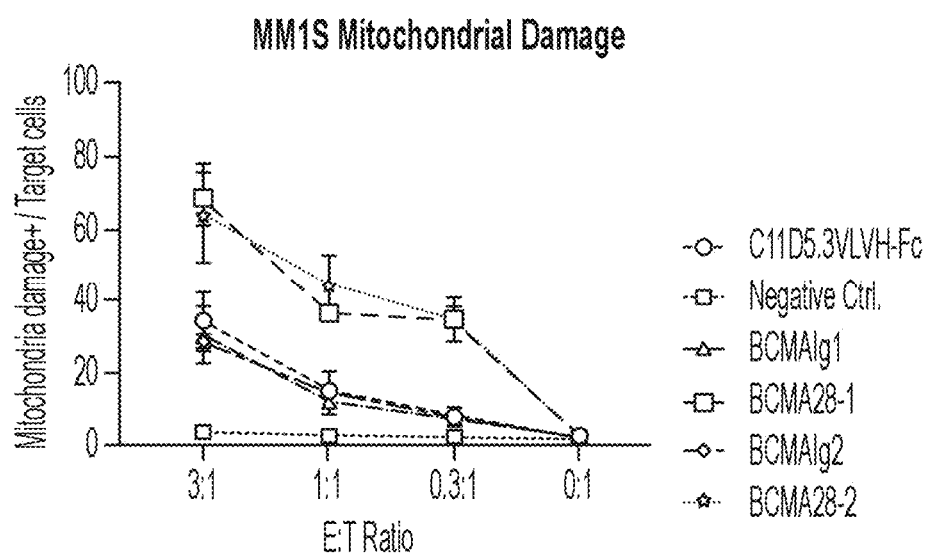

[Fig. 11A]
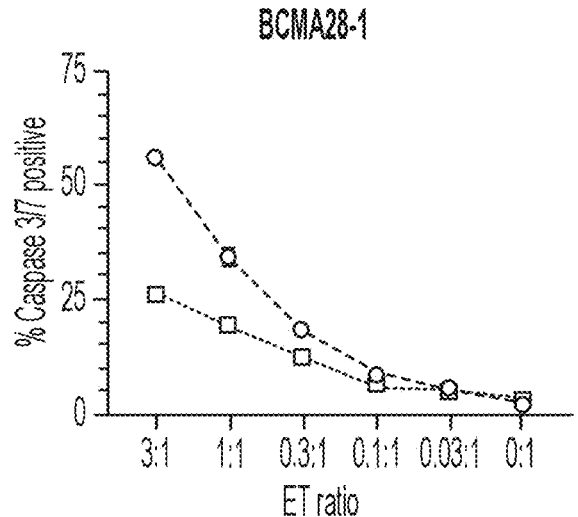
[Fig. 11B]
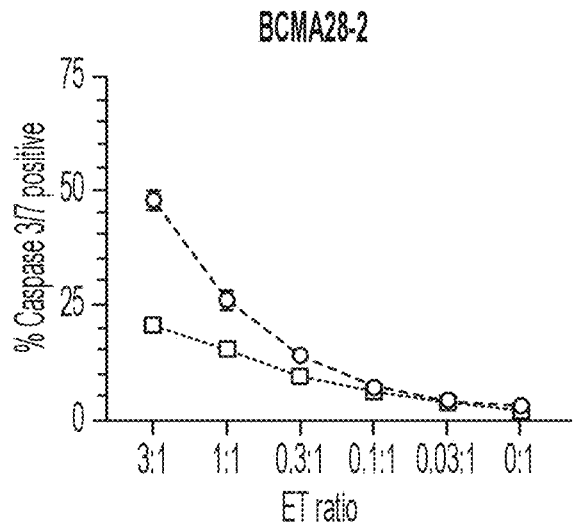
[Fig. 11C]
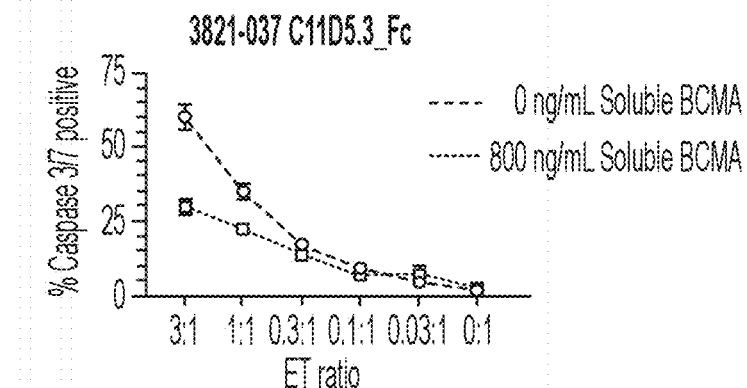

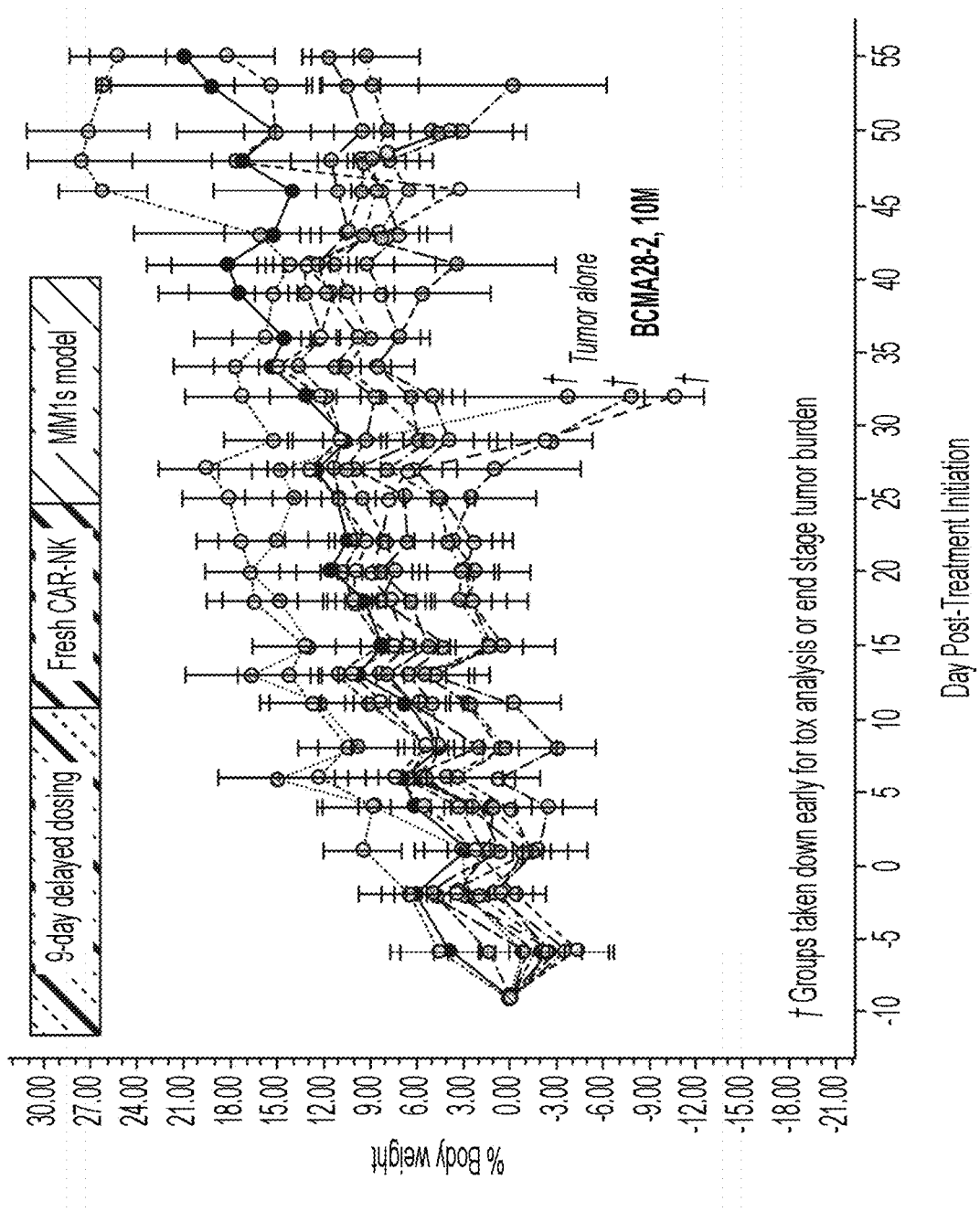
[Fig. 12A]

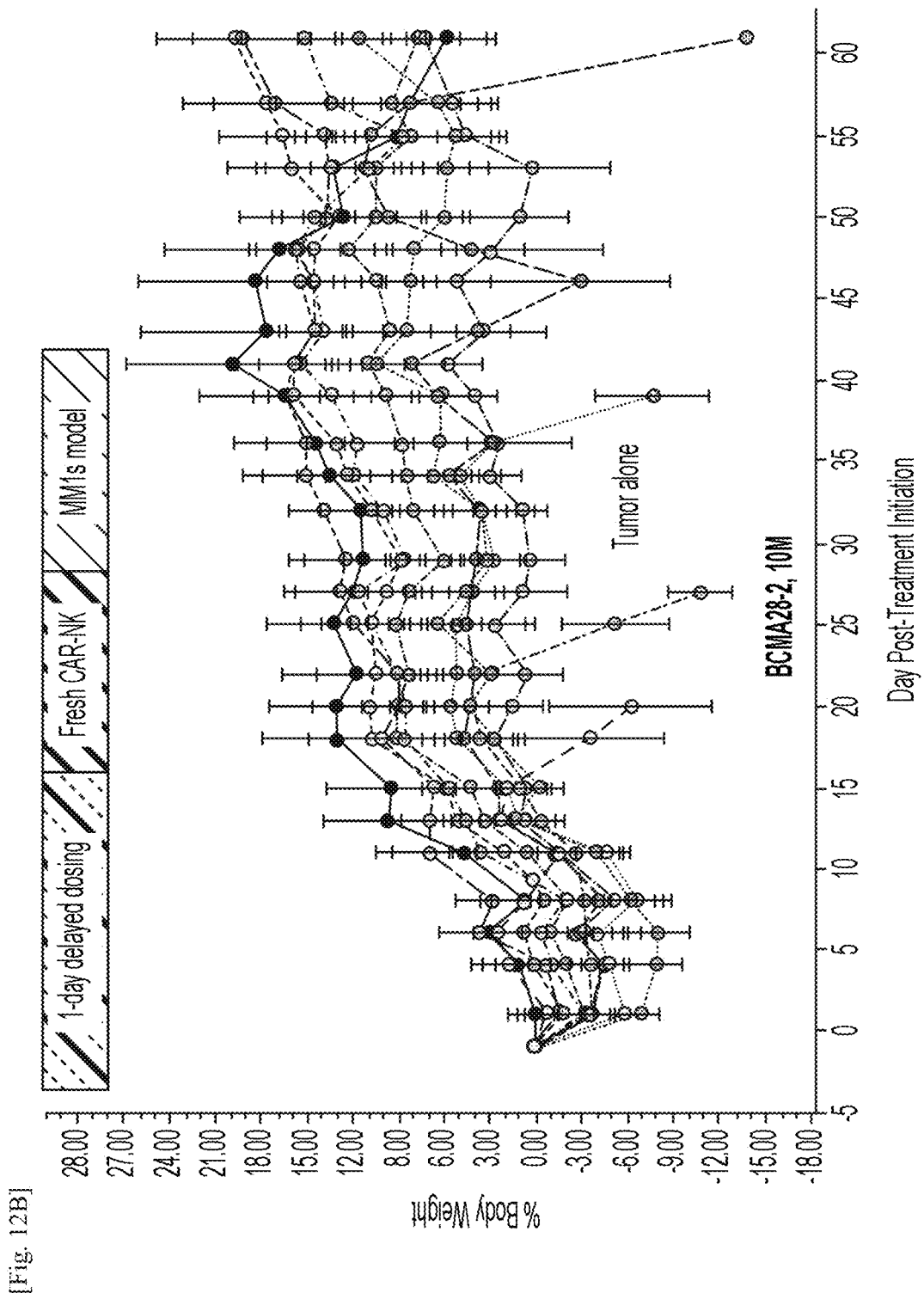
[Fig. 12B]

[Fig. 13]
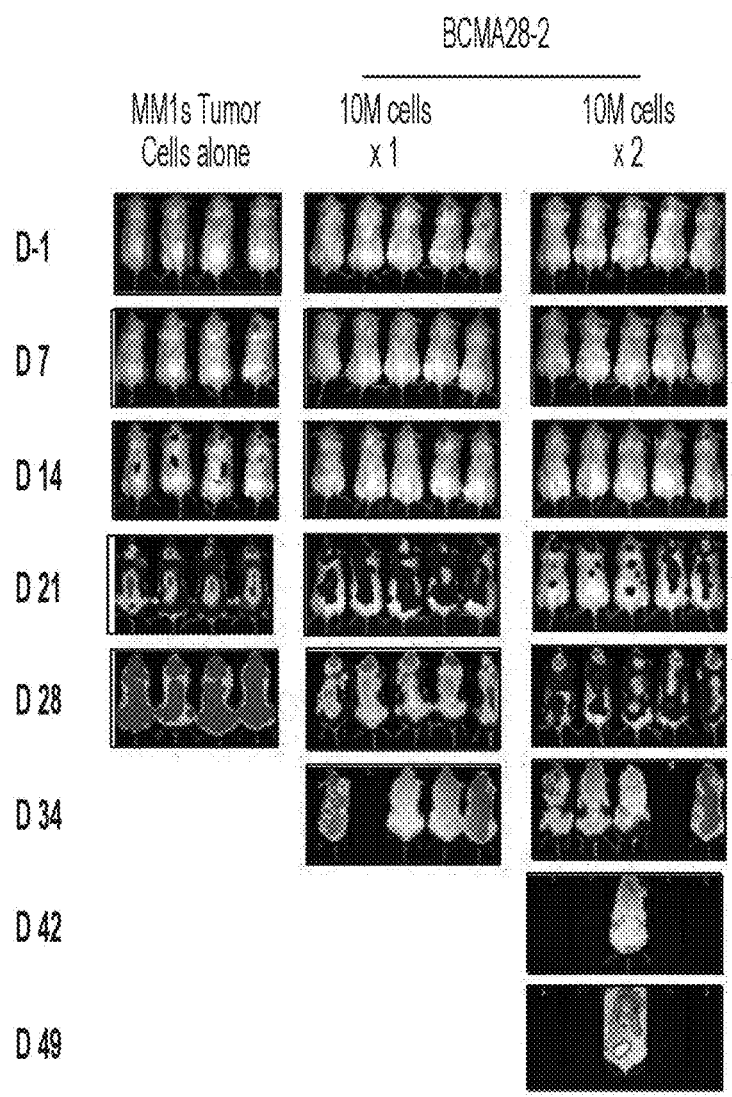

[Fig. 14A]
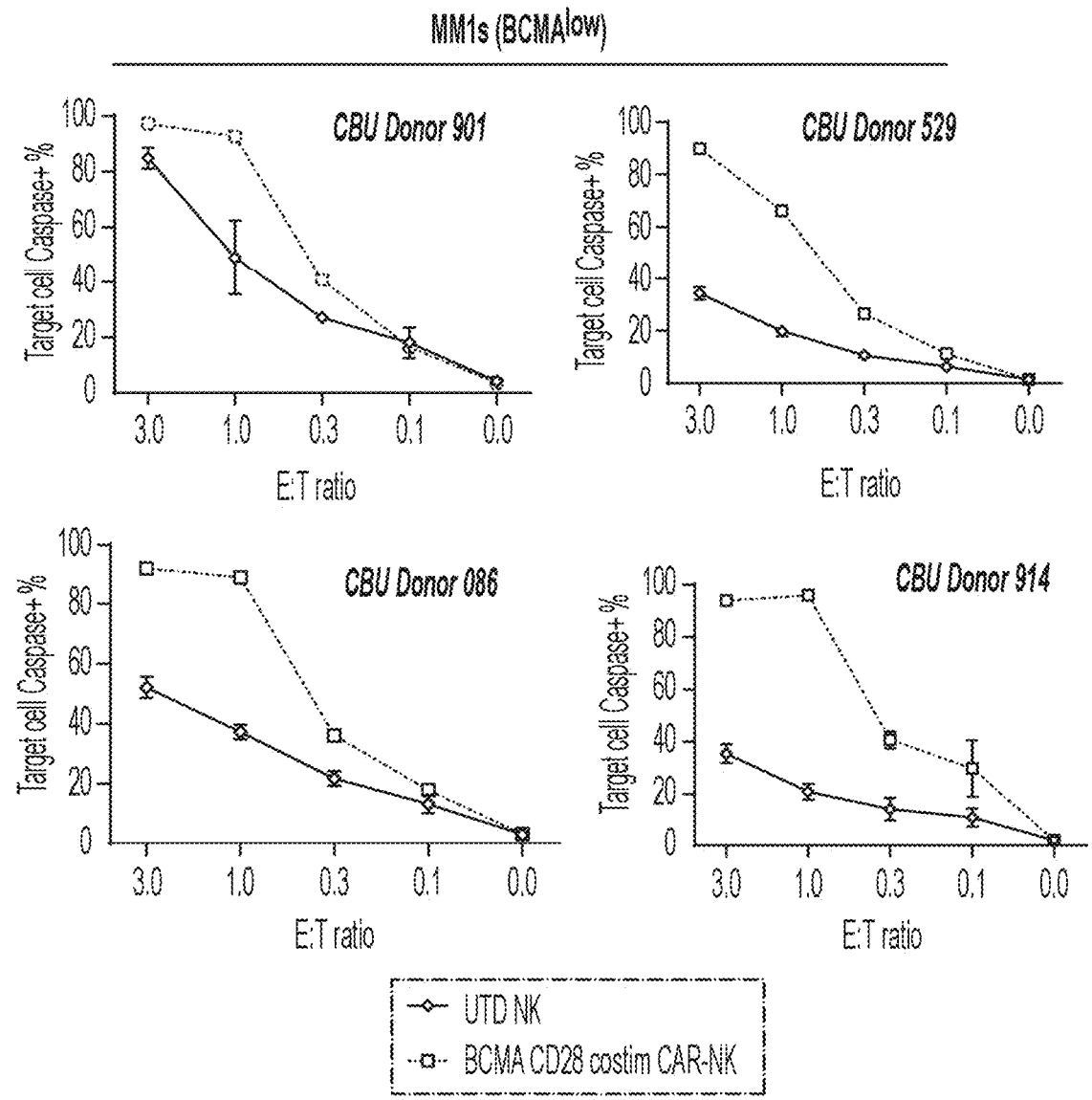

[Fig. 14B]
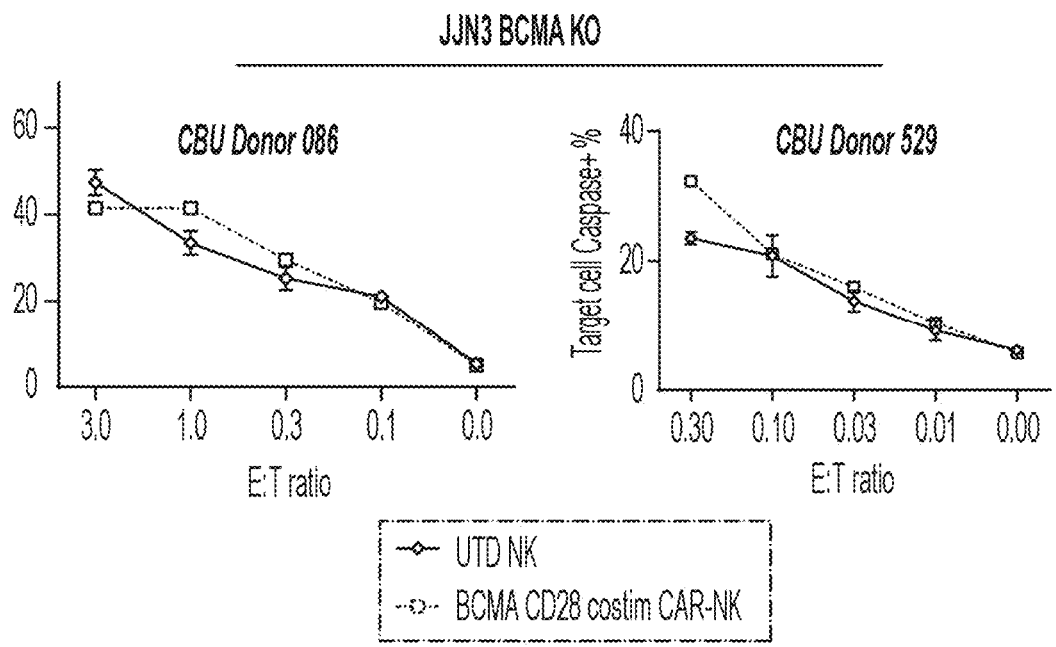
[Fig. 14C]
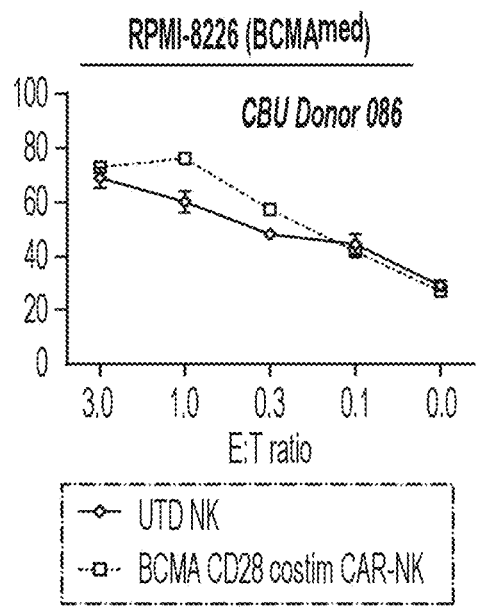

[Fig. 14D]
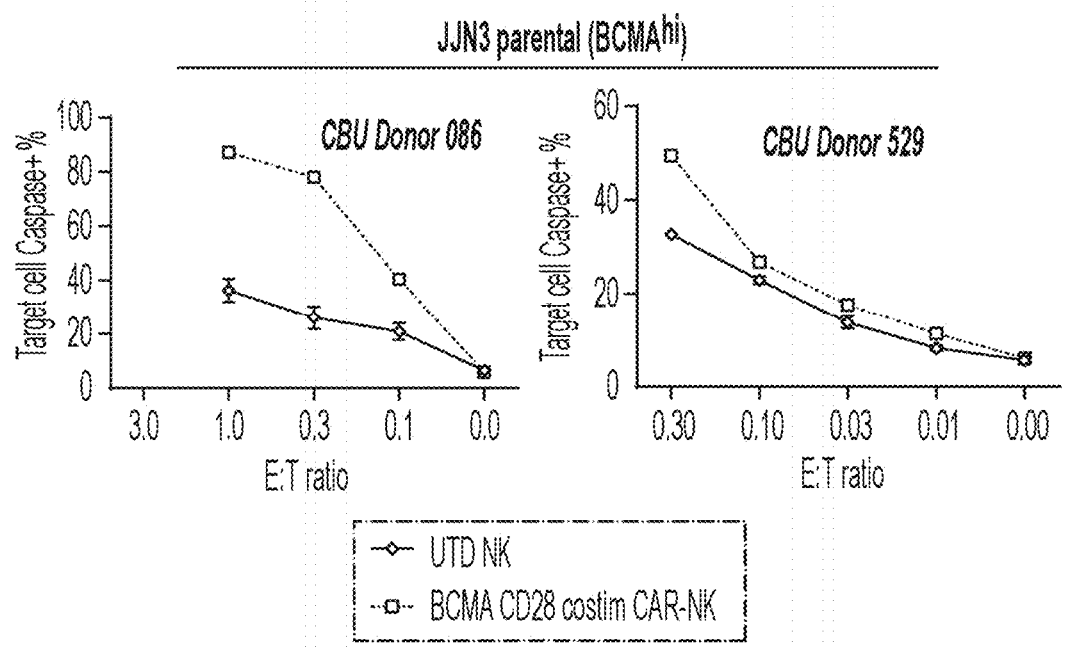

[Fig. 15A]
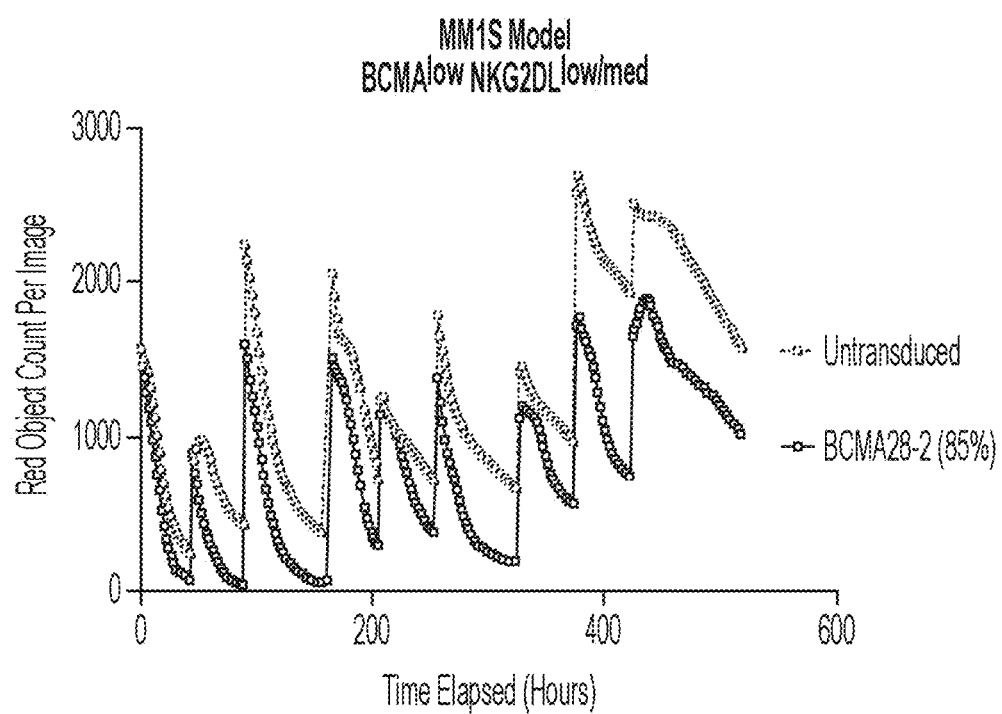

[Fig. 15B]
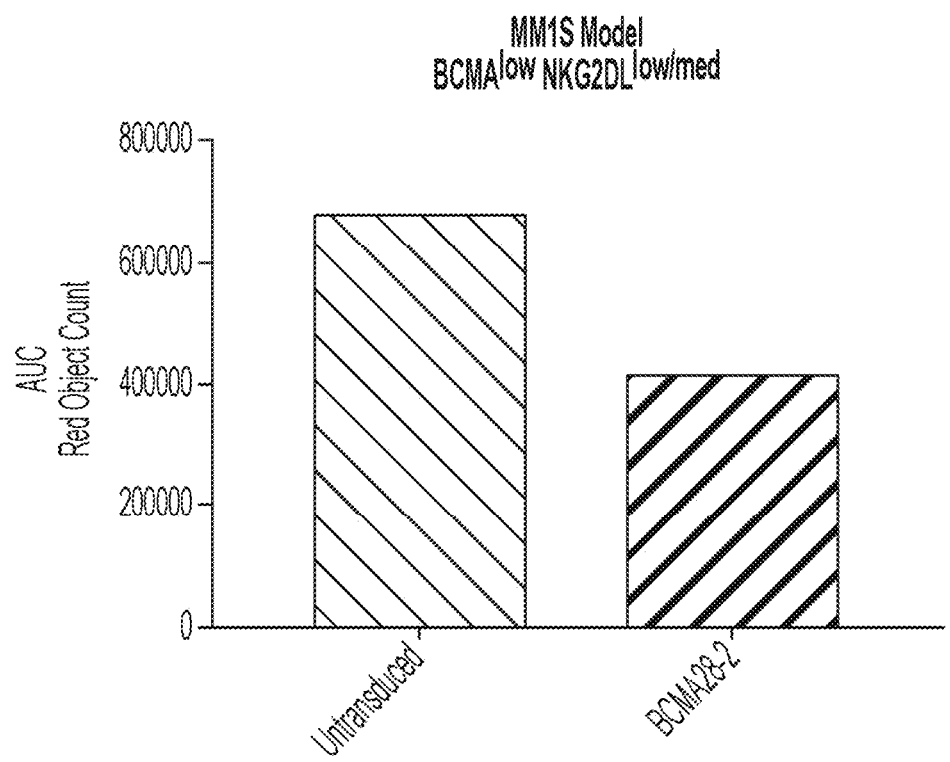

[Fig. 16]
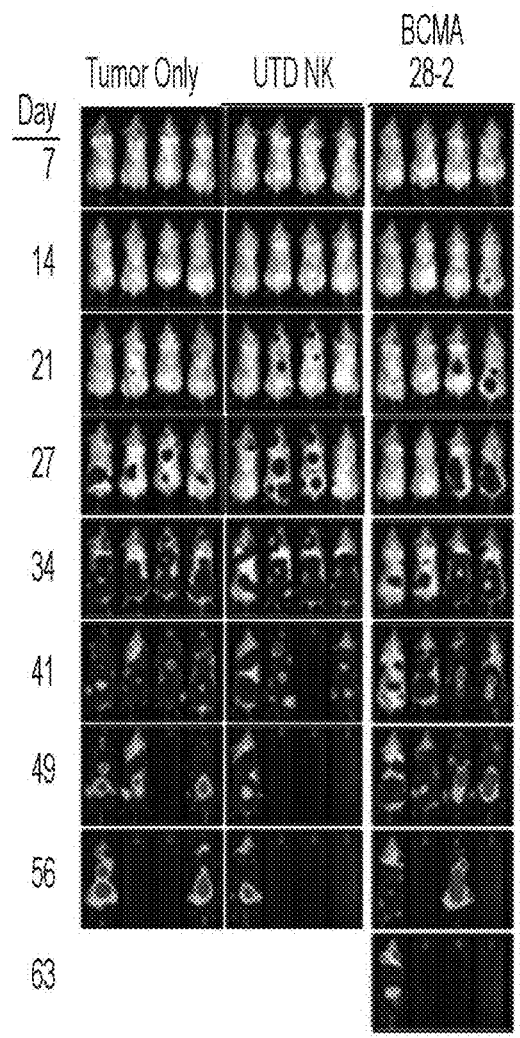

COMPOSITIONS TARGETING BCMA AND METHODS OF USE THEREOF

CROSS REFERENCE TO RELATED APPLICATIONS

This application claims priority to, and the benefit of, U.S. provisional application No. 63/257,822, filed on Oct. 20, 2021; and U.S. provisional application No. 63/257,846 filed on Oct. 20, 2021 and is a U.S. continuation application of PCT/JP2022/040573 filed on Oct. 19, 2022; the contents of each of which are hereby incorporated by reference in their entireties.

INCORPORATION BY REFERENCE OF SEQUENCE LISTING

The instant application is being filed with an electronically filed Sequence Listing in XML format. The sequence listing file entitled MIL-019WO1_SL_Cor, was created on Oct. 23, 2024, and is 112 kilobytes in size; the information in electronic format of the Sequence Listing is incorporated herein by reference in its entirety.

BACKGROUND

B-cell maturation antigen (also known as BCMA, CD269, TNFRSF17), a non-glycosylated type I transmembrane protein, is a member of the tumor necrosis receptor superfamily that is preferentially expressed in differentiated plasma cells. BCMA has been shown to overexpress in various cancers, particularly various B-cell related cancers including lymphomas, multiple myeloma, among other cancers. Targeting BCMA has emerged as a promising approach for treating BCMA positive cancers including lymphomas, multiple myeloma and other cancers. The most common treatment modalities for targeting BCMA include BCMA specific antibodies (e.g., bispecific antibody constructs including BiTE® (bispecific T-cell engager) immuno-oncology therapies), antibody-drug conjugates (ADCs), and chimeric antigen receptor (CAR)-modified immune cell therapy.

Chimeric antigen receptor (CAR) technologies are designed to not only mitigate general immunosuppressive tumor microenvironment but also for redirecting of immune effector cells to cell surface tumor specific antigens. CARs are artificially generated for expression on immune effector cells as trans-membrane receptors to identify tumor cell surface antigen.

Natural killer (NK) cells are attractive contenders for CAR engineering because they mediate effective cytotoxicity against tumor cells and, unlike T-cells, lack the potential to cause graft-versus-host disease (GVHD) in the allogeneic setting. Thus, NK cells could be made available as an off-the-shelf cellular therapy product for immediate clinical use. CAR-NK cells also retain their intrinsic capacity to recognize and target tumor cells through their native receptors, thus in principle, making disease escape through down-regulation of the CAR target antigen less likely than is observed with CAR-T cells.

The present disclosure provides novel anti-BCMA antibodies and B-cell maturation antigen (BCMA) targeting CAR-NK cells that are able to target BCMA antigens on cancer cells through optimized CAR configurations.

SUMMARY

The present invention provides novel human anti-BCMA antibodies, antigen binding fragments thereof, and among other things, novel BCMA CAR constructs comprising new BCMA binders, and BCMA-CAR expressing NK cells. Also provided in the present invention include methods of use of the new BCMA binders, BCMA CARs and/or BCMA-CAR expressing NK cells for treatment of cancers associated with BCMA abnormalities. The present invention is directed to antibodies and antigen binding fragments thereof, and polynucleotides that encode human anti-BCMA antibodies, and a chimeric antigen receptor (CAR) comprising the present anti-BCMA antibodies or antigen binding fragments thereof, that specifically bind to BCMA. In particular, the present invention is based on the observation that the CAR-NK cells targeting BCMA comprising a CAR-containing CD28 hinge domain were unexpectedly more effective in tumor suppression in mouse multiple myeloma models, compared to CAR-NK cells expressing an equivalent CAR construct except with a different (e.g., IgG1) hinge domain. Thus, the present invention provides improved BCMA-CAR constructs for signalling in NK cells, resulting in more efficacious immunotherapy for BCMA-positive tumors.

In one aspect of the present invention, provided herein include human anti-BCMA antibodies and antigen-binding fragments thereof; such human anti-BCMA antibodies and fragments thereof bind to human BCMA with high specificity and affinity.

In some embodiments, the present anti-BCMA antibody or antigen-binding fragment thereof comprises a heavy chain variable region comprising three heavy chain complementarity regions (HCDRs), wherein HCDR1 comprises SYAIH (SEQ ID NO: 2), HCDR2 comprises VTWHDG-SNKYYAESVMG (SEQ ID NO: 3), and HCDR3 comprises AKFGEPQYFQH (SEQ ID NO: 4).

In some embodiments, the present anti-BCMA antibody or antigen-binding fragment thereof binds to BCMA with a $K_D$ of greater than 0 and less than 150 nM. In some embodiments, the anti-BCMA antibody or antigen-binding fragment thereof binds to BCMA with a $K_D$ of greater than 1 pM and less than 10 nM. In some embodiments, the anti-BCMA antibody or antigen-binding fragment thereof binds to BCMA presented on human cells with an EC50 of between 0.05 to 0.5 µg/ml.

In some embodiments, the anti-BCMA antibody or antigen-binding fragment thereof comprises three light chain variable regions (LCDRs), wherein the LCDR2 comprises AASTLQS (SEQ ID NO: 7).

In some embodiments, the anti-BCMA antibody or antigen-binding fragment thereof comprises three light chain variable regions (LCDRs), wherein the LCDR1 comprises RASQGISSYLA (SEQ ID NO: 11), LCDR2 comprises AASTLQS (SEQ ID NO: 7) and LCDR3 comprises QQLN-SYPWT (SEQ ID NO: 14).

In some embodiments, the anti-BCMA antibody or antigen-binding fragment thereof comprises three light chain variable regions (LCDRs), wherein the LCDR1 comprises RASQGINNYLA (SEQ ID NO: 6), LCDR2 comprises AASTLQS (SEQ ID NO: 7) and LCDR3 comprises QQLKSYPFT (SEQ ID NO: 8).

In some embodiments, the anti-BCMA antibody or antigen-binding fragment thereof comprises three light chain variable regions (LCDRs), wherein the LCDR1 comprises RASQGISSYLA (SEQ ID NO: 11), LCDR2 comprises AASTLQS (SEQ ID NO: 7) and LCDR3 comprises QQLN-SYPFT (SEQ ID NO: 12).

In some embodiments, the BCMA antibody or antigen-binding fragment thereof is an antibody comprising an IgG constant region.

In one embodiment, the present disclosure encompasses an anti-BCMA antibody or antigen-binding fragment thereof comprising, three LCDRs, wherein, LCDR1 comprises RASQGIX$_1$X$_2$YLA (SEQ ID NO: 79), LCDR2 comprises AASTLQS (SEQ ID NO: 7), and/or LCDR3 comprises QQLX$_3$SYPX$_4$T (SEQ ID NO: 80); wherein, X$_1$ is selected from S or N;
X$_2$ is selected from S or N;
X$_3$ is selected from N or K; and/or
X$_4$ is selected from F or W.

In some embodiments, the anti-BCMA antibody or antigen binding fragment thereof comprises a variable heavy chain region (VH) comprising SEQ ID NO: 1. In some embodiments, the anti-BCMA antibody or antigen binding fragment thereof comprises a VH at least 85%, at least 90%, at least 95%, at least 96%, at least 97%, at least 98% or at least 99% identical to SEQ ID NO: 1. In some embodiments, the BCMA antibody or antigen binding fragment thereof comprises a VH comprising SEQ ID NO: 9. In some embodiments, the antibody or the antigen binding fragment thereof comprises a VH at least 85%, at least 90%, at least 95%, at least 96%, at least 97%, at least 98% or at least 99% identical to SEQ ID NO: 9.

In some embodiments, the anti-BCMA antibody or antigen binding fragment thereof comprises a variable light chain region (VL) comprising SEQ ID NO: 5, 10 or 13. In some embodiments, the BCMA antibody or antigen binding fragment thereof comprises a VL at least 90%, at least 95%, at least 96%, at least 97%, at least 98% or at least 99% identical to SEQ ID NO: 5, 10 or 13.

In some embodiments, the BCMA antigen binding fragment is selected from the group consisting of an IgA antibody, IgG antibody, IgE antibody, IgM antibody, bi- or multi-specific antibody, Fab fragment, Fab' fragment, F(ab')2 fragment, Fd' fragment, Fd fragment, isolated CDRs or sets thereof; single-chain variable fragment (scFv), polypeptide-Fc fusion, single domain antibody, cameloid antibody; masked antibody, Small Modular ImmunoPharmaceutical ("SMIPs™"), single chain, Tandem diabody, VHHs, Anticalin, Nanobody, minibodies, BiTE, ankyrin repeat protein, DARPIN, Avimer, DART, TCR-like antibody, Adnectin, Affilin, Trans-body; Affibody, TrimerX, MicroProtein, Fynomer, Centyrin; and KALBITOR.

In some embodiments, the anti-BCMA antibody or antigen binding fragment thereof comprises a single-chain variable fragment (scFv). In some embodiments, the anti-BCMA antibody or antigen binding fragment comprises a linker sequence. In some embodiments, the anti-BCMA antibody or antigen binding fragment comprises a linker selected from SEQ ID NO: 15-18. In some embodiments, the anti-BCMA antibody or antigen binding fragment comprises a signal peptide. In some embodiments, the anti-BCMA antibody or antigen binding fragment thereof comprises a scFv of SEQ ID NOs: 85-87. In some embodiments, the anti-BCMA antibody or antigen binding fragment thereof comprises a scFv at least 80%, at least 85%, at least 90%, at least 95%, at least 95%, at least 96%, at least 97%, at least 98% or at least 99% identical to SEQ ID Nos: 85-87.

In some embodiments, the present disclosure encompasses a pharmaceutical composition comprising an anti-BCMA antibody or antigen-binding fragment thereof as described herein and a pharmaceutically acceptable carrier. As non-limiting examples, the anti-BCMA antibody or antigen-binding fragment thereof comprises:
a heavy chain variable region comprising three heavy chain complementarity regions (HCDRs), wherein HCDR1 comprises SYAIH (SEQ ID NO: 2), HCDR2 comprises VTWHDGSNKYYAESVMG (SEQ ID NO: 3), and HCDR3 comprises AKFGEPQYFQH (SEQ ID NO: 4). In other examples, the anti-BCMA antibody or fragment thereof may comprises a light chain variable complementarity determining region (LCDR) 2 comprises AASTLQS (SEQ ID NO: 7).

As a non-limiting example, the present anti-BCMA antibody, or antigen binding fragment thereof comprises three HCDRs including a HCDR1 comprising SYAIH (SEQ ID NO: 2), a HCDR2 comprising VTWHDGSNKYYAESVMG (SEQ ID NO: 3), and a HCDR3 comprising AKFGEPQYFQH (SEQ ID NO: 4), and three LCDRs including a LCDR1 comprising RASQGINNYLA (SEQ ID NO: 6), a LCDR2 comprising AASTLQS (SEQ ID NO: 7) and LCDR3 comprising QQLKSYPFT (SEQ ID NO: 8).

In one embodiment, the present anti-BCMA antibody, or antigen binding fragment thereof comprises three HCDRs including a HCDR1 comprising SYAIH (SEQ ID NO: 2), a HCDR2 comprising VTWHDGSNKYYAESVMG (SEQ ID NO: 3), and a HCDR3 comprising AKFGEPQYFQH (SEQ ID NO: 4), and three LCDRs including a LCDR1 comprising RASQGISSYLA (SEQ ID NO: 11), a LCDR2 comprising AASTLQS (SEQ ID NO: 7) and a LCDR3 comprising QQLNSYPWT (SEQ ID NO: 14).

In another embodiment, the present anti-BCMA antibody, or antigen binding fragment thereof comprises three HCDRs including a HCDR1 comprising SYAIH (SEQ ID NO: 2), a HCDR2 comprising VTWHDGSNKYYAESVMG (SEQ ID NO: 3), and a HCDR3 comprising AKFGEPQYFQH (SEQ ID NO: 4), and three LCDRs including a LCDR1 comprising RASQGISSYLA (SEQ ID NO: 11), a LCDR2 comprising AASTLQS (SEQ ID NO: 7) and a LCDR3 comprising QQLNSYPFT (SEQ ID NO: 12).

In another aspect of the present invention, provided includes a chimeric antigen receptor (CAR) comprising an extracellular BCMA binding domain, a CD28 hinge region, a transmembrane domain, and one or more intracellular cell signalling domains, wherein the BCMA binding domain comprises an anti-BCMA antibody or an antigen-binding fragment thereof as described herein. Accordingly the BCMA binding CAR as described herein recognizes and binds to a BCMA antigen specifically.

In some embodiments, the present invention provides a polynucleotide that encodes a chimeric antigen receptor (CAR) comprising a BCMA antigen binding domain, a CD28 hinge region, a transmembrane domain, and one or more intracellular cell signalling domains. In some embodiments, the polynucleotide may comprise at least one modification.

In some embodiments, the polynucleotide comprises a sequence that encodes a BCMA antigen binding domain comprising: (a) a heavy chain variable region complementarity determining region (HCDR) 1 comprising SEQ ID NO: 2, (b) a HCDR2 comprising SEQ ID NO: 3, and (c) a HCDR3 comprising SEQ ID NO: 4.

In some embodiments, the polynucleotide comprises a sequence that encodes a BCMA antigen binding domain comprising: (a) a light chain variable region complementarity determining region (LCDR) 1 comprising SEQ ID NO: 6, (b) a LCDR2 comprising SEQ ID NO: 7, and (c) a LCDR3 comprising SEQ ID NO: 8. In some embodiments, the polynucleotide comprises a sequence that encodes a BCMA antigen binding domain comprising: (a) a LCDR1 comprising SEQ ID NO: 11, (b) a LCDR2 comprising SEQ ID NO: 7 and (c) a LCDR3 comprising SEQ ID NO: 12. In some embodiments, the polynucleotide comprises a sequence that encodes a BCMA antigen binding domain comprising: (a) a LCDR1 comprising SEQ ID NO: 11, (b) a LCDR2 comprising SEQ ID NO: 7, and (c) a LCDR3 comprising SEQ ID NO: 14.

In some embodiments, the polynucleotide encodes a BCMA antigen binding domain comprising an amino acid sequence at least about 95%, at least about 96%, at least about 97%, at least about 98%, at least about 99%, or about 100% identical to SEQ ID NO: 1 or 9. In some embodiments, the polynucleotide encodes a BCMA antigen binding domain comprising an amino acid sequence at least about 95%, at least about 96%, at least about 97%, at least about 98%, at least about 99%, or about 100% identical to any of SEQ ID NO: 5, 10 or 13.

In some embodiments, the antigen binding fragment is selected from the group consisting of: a Fab fragment, a F(ab')2 fragment, an Fv fragment, or a single chain variable fragment (scFv). In some embodiment, the antigen binding domain comprises an scFv. In some embodiments, the VH and the VL of an scFv are connected by a linker. In some embodiments, the linker comprises between about 50 amino acids and about 2 amino acids. In some embodiments, the linker comprises an amino acid sequence at least 75%, at least 85%, at least 85%, at least 90%, at least 95%, at least 96%, at least 97%, at least 98%, at least 99%, or 100% identical to SEQ ID NO: 15-18.

In some embodiments, the polynucleotide encodes a BCMA binding CAR that binds to BCMA with a $K_D$ of less than about $1\times10^{-6}$ M, less than about $1\times10^{-7}$ M, less than about $1\times10^{-8}$ M, or less than about $1\times10^{-9}$ M.

In some embodiments, the polynucleotide comprises a sequence encoding a transmembrane domain. The transmembrane domain of the present BCMA binding CAR is a transmembrane domain of CD28, CD35, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, or any combination thereof. In some embodiments, the transmembrane domain is a CD28 transmembrane domain.

In some embodiments, the polynucleotide comprises a sequence encoding a hinge region. The hinge region of the present BCMA binding CAR is a CD28 hinge domain. As a non-limiting example, the hinge region comprises an amino acid sequence at least about 80%, at least about 85%, at least about 90%, at least about 95%, at least about 96%, at least about 97%, at least about 98‰, at least about 99‰, or about 100% identical to SEQ ID NO: 36.

In some embodiments, the polynucleotide comprises a sequence encoding a costimulatory region. In some embodiments the costimulatory region is a signalling region of CD28, OX-40, 4-1BB/CD137, CD2, CD7, CD27, CD30, CD40, programmed death-1 (PD-1), inducible T cell costimulator (ICOS), CD8 gamma, CD3 delta, CD3 epsilon, CD247, CD276 (B7-H3), LIGHT (tumor necrosis factor superfamily member 14; TNFSF1.4), NKG2C, Ig alpha (CD79a), Fc gamma receptor, MHC class I molecule, TNF receptor proteins, Immunoglobulin-like proteins, cytokine receptors, integrins, signalling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKD80 (KLRF1), NKD44, NKD30, NKD46, CD 19, CD4, CD8alpha, CD8beta, 11.2 beta, IL2R gamma, IL7R alpha, ITGA4, VLA1, CD49a, ITGA4, IA4, CD49D, ITGA6, VLA-6, CD49f, ITGAD, ITGAE, CD103, ITGAL, LFA-1, ITGAM, ITGAX, ITGB1, CD29, ITGB2, CD18, LFA-1, ITGB7, NKG2D, TNFR2, TRANCE RANKL, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), CD69, SLAMF6 (NTB-A, Ly108), BLAME (SLAMF8), SELPLG (CD 162), LTBR, LAT, GADS, SLP-76, PAG/Cbp, CD 19a, a ligand that specifically binds with CD83, or any combination thereof. In some embodiments, the costimulatory region comprises an amino acid sequence at least about 80%, at least about 85%, at least about 90%, at least about 95%, at least about 96%, at least about 97%, at least about 98%, at least about 99%, or about 100% identical to SEQ ID NO: 28.

In some embodiments, the polynucleotide comprises a sequence encoding an activation domain. As a non-limiting example, the activation domain is a CD35 domain. In some embodiments, the activation domain comprises an amino acid sequence at least about 80%, at least about 85%, at least about 90%, at least about 95%, at least about 96%, at least about 7, at least about 98%, at least about 99%, or about 100% identical to SEQ ID NO: 30.

In some embodiments, the polynucleotide further comprises a sequence encoding a suicide gene. In some embodiments, the polynucleotide comprises a suicide gene selected from Rituximab, iCaspase 9, Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk). In some embodiments, wherein the suicide gene is iCaspase9.

In some embodiments, the polynucleotide further comprises a sequence encoding a cytokine. In some embodiments, the cytokine is selected from IL-7, IL-12, IL-15, IL-18, or IL-21. In some embodiments, the cytokine is IL-15. In some embodiments, the amino acid sequence of IL-15 comprises SEQ ID NO: 23.

In some embodiments, the BCMA binding CAR as described herein comprises an amino acid sequence at least about 80%, at least about 85%, at least about 90%, at least about 95%, at least about 96%, at least about 97%, at least about 98%, at least about 99%, or about 100% identical to SEQ ID NOs: 19-21.

In some embodiments, the present disclosure comprises a vector comprising the polynucleotide of any of the previous embodiments.

In some embodiments the vector is a retroviral vector, a DNA vector, a plasmid, a RNA vector, an adenoviral vector, an adenovirus associated vector, a lentiviral vector, or any combination thereof.

In some embodiments, the present disclosure provides a cell expressing a BCMA binding CAR as described herein. In some embodiments, the CAR expressing cell comprises a polynucleotide that encodes a BCMA binding CAR as described herein. In other embodiments, the CAR expressing cell comprises the vector as described herein.

In some embodiments, the cell is an immune cell. In some embodiments, the immune cell is an NK-cell, a T-cell or a tumor-infiltrating lymphocyte (TIL), iNKT cells, B cells, macrophages, dendritic cells, or a mixture thereof. In some embodiments, the present disclosure is directed to a population of immune cells comprising the immune cell of any one of the above embodiments.

In some embodiments, the present disclosure is directed to a composition comprising the polynucleotide of any of the above embodiments, the vector of any of the above embodiments, the CAR of any of the above embodiments, or the cell of any of the above embodiments.

As a non-limiting example, the present disclosure is directed to, an NK-cell comprises a polynucleotide encoding a CAR comprising: (a) an antigen binding molecule specifically binding to BCMA comprising a heavy chain variable region (VH) at least about 95%, at least about 96%, at least about 97%, at least about 98%, at least about 99%, or about 100% identical to SEQ ID NO: 1 or 9, and a light chain variable region (VL) at least about 95%, at least about 96%, at least about 97%, at least about 98%, at least about 99%, or about 100% identical to any of SEQ ID NO: 5, 10 or 13, (b) a CD28 hinge region, (c) a transmembrane domain, and (d) one or more intracellular cell signalling domains, In some aspects, the present disclosure encompasses a polynucleotide encoding a BCMA binding CAR, comprising: (a) a CD28 hinge, (b) a transmembrane domain, (c) a costimulatory domain, and (d) IL-15 cytokine.

In one aspect, the present disclosure encompasses an immune cell having a polynucleotide encoding a chimeric antigen receptor (CAR) wherein the CAR comprises: (a) an antigen binding domain; (b) a CD28 hinge; and (c) a CD28 transmembrane domain. In some embodiments, the immune cell comprises a CAR binding to BCMA expressed on tumor cells.

In yet another aspect of the present invention, provided include methods of use of the anti-BCMA antibodies, antigen-binding fragments thereof, BCMA binding CARs, vectors, cells and compositions as described herein.

In some embodiments, the present disclosure provides a method of treating cancer in an individual using an anti-BCMA antibody, an antigen binding fragment thereof, a BCMA binding CAR, a polynucleotide, a vector and/or a cell expressing the BCMA binding CAR; the method comprises the step of administering to the individual a therapeutically effective amount of any one of the antibodies, CARs, polynucleotides, vectors, cells and compositions discussed in the present disclosure.

In some embodiments, the present method further comprises the step of providing to the individual an effective amount of an additional therapy.

In some embodiments, the additional therapy comprises surgery, radiation, gene therapy, immunotherapy, or hormone therapy.

In some embodiments, the cells harboring the polynucleotide or the cells harboring the vector are administered to the individual by infusion, injection, intravenously, intraarterially, intraperitoneally, intratracheally, intratumorally, intramuscularly, endoscopically, intralesionally, intracranially, percutaneously, subcutaneously, regionally, by perfusion, in a tumor microenvironment, or a combination thereof.

In some embodiments, the cancer is an immune cell malignancy e.g., leukemia, lymphoma, or myeloma. In some embodiments, the cancer is selected from multiple myeloma, lymphoma, and/or leukemia.

BRIEF DESCRIPTION OF DRAWINGS

It should be noted that the various components shown in these and other figures are merely for illustration purposes and should not be read into the claims unless explicitly recited therein.

FIG. 1 is a representation of the construct of an exemplary BCMA-CAR with IL-15 cytokine (e.g., soluble IL-15) and hinge region from CD28.

FIG. 2 is a graph of in vitro cytotoxicity assay of NK cells transduced with BCMA CAR with IgG hinge and CD28 hinge, as compared to non-transduced (NT) cells.

FIG. 3 is a pictorial depiction of tumor progression in co-dosed NK cells expressing BCMA-CAR with IgG hinge or CD28 hinge domain.

FIG. 4 is a pictorial depiction of tumor progression with different co-dosed NK cells expressing BCMA-CARs (1M or 3M) with CD28 hinge domain.

FIG. 5 is a pictorial depiction of different co-dosed NK cells expressing BCMA-CARs (1M) with CD28 hinge domain.

FIG. 6 is a pictorial depiction of NK cells expressing BCMA-CAR administered at 1M or 3M concentration, one day following MM1S tumor cell inoculation ("1-day delayed dosing"); non-transduced NK cells as control (NT-NK).

FIG. 7 is a Kaplan Meier survival curve of mice administered NK cells comprising BCMA CAR administered at 1 million or 3 million dosage, one day following MM1s tumor cell inoculation ("1-day delayed dosing")

FIG. 8 is a slide depiction of histopathological analysis of mice lungs, collected following in vivo treatment with 10 million NK cells comprising BCMA-CAR.

FIG. 9A is a graph showing IL-15 secretion in plasma in mice at 1-day delayed dosage. FIG. 9B is a graph showing IL-15 secretion in plasma in mice at 9-day delayed dosage. FIG. 9C is a graph showing proliferation of CAR-NK cells in blood in mice at 9-day delayed dosage. FIG. 9D is a graph showing proliferation of CAR-NK cells in blood in mice at 1-day delayed dosage.

FIG. 10A is a graph showing tumor cell line killing following treatment at different effector:target (E:T) ratios with BCMA-CART cells comprising CD28 hinge or IgG hinge as compared to C11D5.3VLVH-Fc. FIG. 10B is a graph showing % caspase+ MM1s target cell, as a marker of apoptosis, following treatment at different E:T ratios with BCMA-CART cells comprising CD28 hinge or IgG hinge. FIG. 10C is a graph showing % mitochondrial damage of BCMA expressing MM1s tumor cells following treatment at different E:T ratios with BCMA-CART cells comprising CD28 hinge or IgG hinge.

FIG. 11A-B are graphical representations of in vitro cytotoxicity with BCMA28-1 and BCMA28-2 CAR-containing NK cells respectively, in the presence or absence of 800 ng/ml soluble BCMA. FIG. 11C is a graphical representation of in vitro cytotoxicity with C11D5.3Fc positive control, in the presence or absence of 800 ng/mL soluble BCMA FIG. 12 are graphs showing weight fluctuations in mice treated with BCMA CAR NK, at 10M dose, dosed 9 days post-tumor cell inoculation ("9-day delayed dose") (FIG. 12A) and dosed 1 day post-tumor cell inoculation ("1-day delayed dose") (FIG. 12B).

FIG. 13 shows the representative images of the survival of mice inoculated with luciferase-expressing MM tumor cells, who then received either one (10 Mx1) or two doses (10M×2) of BCMA28-2 expressing CAR-NK cells.

FIG. 14 shows in vitro killing activity of BCMA28-2 CAR construct containing NK cells, generated in 4 independent cord blood unit (CBU) donors, against multiple tumor cell lines. FIG. 14A shows in vitro killing activity of BCMA28-2 construct containing CAR-NK cells in MM1s (BCMA$^{low}$) cells across 4 independent CBU donors versus equivalent untransduced (UTD) NK cells. FIG. 14B shows in vitro killing activity of BCMA28-2 construct containing CAR-NK cells in JJN3 (BCMA KO) cells across 4 independent donors versus equivalent untransduced (UTD) NK cells. FIG. 14C shows in vitro killing activity of BCMA28-2 construct containing CAR-NK cells in RPMI-8226

(BCMA$^{high}$) cells across 4 CBU independent donors versus equivalent untransduced (UTD) NK cells. FIG. 14D shows in vitro killing activity of BCMA28-2 construct containing CAR-NK cells in JIN parental (BCMA$^{med}$) cells across 4 CBU independent donors versus equivalent untransduced (UTD) NK cells.

FIGS. 15A and 15B show the repeat-killing anti-tumor activity of BCMA28-2 expressing CAR NK cells in MM1S tumor model in vitro following multiple rounds of tumor cell addition.

FIG. 16 shows in vivo efficacy of BCMA28-2 constructs against RPMI-8226 tumor.

DETAIL DESCRIPTION

Definitions

In keeping with long-standing patent law convention, the words "a" and "an" when used in the present specification in concert with the word comprising, including the claims, denote one or more than one (i.e., to at least one) of the grammatical object of the article. By way of example, "an element" means one element or more than one element. Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

Affinity: As used herein, the term "affinity" refers to the characteristics of a binding interaction between a binding moiety (e.g., an antigen binding moiety (e.g., variable domain described herein) and/or Fc receptor binding moiety (e.g., FcRn binding moiety described herein)) and a target (e.g., an antigen (e.g., BCMA) and/or FcR (e.g., FcRn)) and that indicates the strength of the binding interaction. In some embodiments, the measure of affinity is expressed as a dissociation constant ($K_D$). In some embodiments, a binding moiety has a high affinity for a target (e.g., a $K_D$ of less than about $10^{-7}$ M, less than about $10^{-8}$ M, or less than about $10^{-9}$ M, less than about $10^{-10}$, less than about $10^{-10}$, less than about $10^{-11}$, less than about $10^{-12}$). In some embodiments, a binding moiety has a low affinity for a target (e.g., a $K_D$ of higher than about $10^{-7}$ M, higher than about $10^{-6}$ M, higher than about $10^{-5}$ M, or higher than about $10^{-4}$ M). In some embodiments, a binding moiety has high affinity for a target at a first pH, has low affinity for the target at a second pH, and has an intermediate affinity for the target at a pH level between the first pH and the second pH.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

Antigen-binding fragment or antibody fragment thereof refers to a portion of an intact antibody. An antigen-binding fragment or antibody fragment thereof refers to a portion of an intact antibody that binds to an antigen (e.g., BCMA). An antigen-binding fragment can contain the antigenic determining variable regions of an intact antibody. Examples of antibody fragments include, but are not limited to Fab, Fab', F(ab')$_2$, and Fv fragments, linear antibodies, antibody mimetics, scFvs, and single chain antibodies.

Binding Moiety: As used herein, a "binding moiety" is any molecule or part of a molecule capable of specifically binding a target, e.g., a target of interest (e.g., an antigen (e.g., BCMA) and/or FcR (e.g., FcRn)). Binding moieties include, e.g., antibodies, antigen binding fragments thereof, Fc regions or Fc fragments thereof, antibody mimetics, peptides, and aptamers.

BCMA: As used herein, the term "BCMA" refers to B-cell maturation antigen. The human BCMA protein consists of 184 amino-acids: 1-54: extracellular domain; 55-77: transmembrane domain; 78-184: cytoplasmic domain. The amino-acid sequence of BCMA comprises:

(SEQ ID NO: 22)
MLQMAGQCSQNEYFDSLLHACIPCQLRCSSNTPPLTCQRYCNASVTNSV

KGTNAILWTCLGLSLIISLAVFVLMFLLRKISSEPLKDEFKNTGSGLLG

MANIDLEKSRTGDEIILPRGLEYTVEECTCEDCIKSKPKVDSDHCFPLP

AMEEGATILVTTKTNDYCKSLPAALSATEIEKSISAR, extracellular domain sequence is underlined.)

BCMA lacks signalling peptide and resembles other receptors such as BAFF receptor, transmembrane activator, cyclophilin ligand interactor and calcium modulator (TACI). These receptors play major role in B cell maturation and differentiation into plasma cells. Their ligands include BAFF and APRIL which expression are increased in MM patients. BCMA is a cell surface receptor, also known as CD269 and tumor necrosis factor receptor superfamily member 17 (TNFRSF17) that is encoded by TNFRSF17 gene. This receptor is expressed mainly in mature B lymphocytes and in most cases of multiple myeloma (MM).

Complementarity Determining Region (CDR): A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1 156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

Chimeric antigen receptor (CAR): A chimeric molecule that includes an antigen-binding portion (such as a BCMA antibody) and a signalling domain, such as a signalling domain from a T cell receptor (e.g. CD32). Typically, CARs are comprised of an antigen-binding moiety, a transmembrane domain and an endodomain. The endodomain typically includes a signalling chain having an immunoreceptor tyrosine-based activation motif (IT AM), such as CD32 or FceRIy. In some instances, the endodomain further includes the intracellular portion of at least one additional co-stimulatory domain, such as CD28 and/or CD137.

Constant region: As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

Engineered: As used herein, the term "engineered" as used herein refers to an entity that is generated by the hand of man, including a cell, nucleic acid, polypeptide, vector, and so forth. In at least some cases, an engineered entity is synthetic and comprises elements that are not naturally present or configured in the manner in which it is utilized in the disclosure.

Epitope: As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al, (1994) Acta Crystallogr D Biol Crystallogr 50 (Pt 4): 339-350; McPherson A (1990) Eur J Biochem 189:1-23; Chayen N E (1997) Structure 5:1269-1274; McPherson A (1976) J Biol Chem 251:6300-6303). Antibody: antigen crystals may be studied using well known X-ray diffraction techniques and may be refined using computer software known in the art, e.g., Refmac and Phenix. Mutagenesis mapping studies may be accomplished using any method known to one of skill in the art. See, e.g., Champe M et al, (1995) J Biol Chem 270:1388-1394 and Cunningham B C & Wells J A (1989) Science 244:1081-1085 for a description of mutagenesis techniques, including alanine scanning mutagenesis techniques.

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

Isolated: The term "isolated" as used herein refers to molecules or biologicals or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, such as that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides that are isolated from other cellular proteins and is meant to encompass both purified and recombinant polypeptides. The term "isolated" is also used herein to refer to cells or tissues that are isolated from other cells or tissues and is meant to encompass both cultured and engineered cells and tissues.

$K_a$: As used herein, "$K_a$" refers to an association rate of a particular binding moiety and a target to form a binding moiety/target complex.

$K_d$: As used herein, "$K_d$" refers to a dissociation rate of a particular binding moiety/target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Natural killer cells: Natural killer cells, or NK cells, are a type of cytotoxic lymphocyte critical to the innate immune system. The role NK cells play is analogous to that of cytotoxic T cells in the vertebrate adaptive immune response. NK cells provide rapid responses to virus-infected cells, acting at around 3 days after infection, and respond to tumor formation.

Percent identity: As used herein, "percent identity," and the similar phrases between the two sequences is a function of the number of identical positions shared by the sequences (i.e., $$\% \text{ identity} = \frac{\text{number of identical positions}}{\text{total number of positions}} \times 100,$$

taking into account the number of gaps, and the length of each gap, which need to be introduced for optimal alignment of the two sequences. Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-2 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Prevent: As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

Sample: The term "sample," as used herein, generally refers to a biological sample. The sample may be taken from tissue or cells from an individual. In some examples, the sample may comprise, or be derived from, a tissue biopsy, blood (e.g., whole blood), blood plasma, extracellular fluid, dried blood spots, cultured cells, discarded tissue. The sample may have been isolated from the source prior to collection. Non-limiting examples include blood, cerebral spinal fluid, pleural fluid, amniotic fluid, lymph fluid, saliva, urine, stool, tears, sweat, or mucosal excretions, and other bodily fluids isolated from the primary source prior to collection. In some examples, the sample is isolated from its primary source (cells, tissue, bodily fluids such as blood, environmental samples, etc.) during sample preparation. The sample may or may not be purified or otherwise enriched from its primary source. In some cases the primary source is homogenized prior to further processing. The sample may be filtered or centrifuged to remove buffy coat, lipids, or particulate matter. The sample may also be purified or enriched for nucleic acids, or may be treated with RNases. The sample may contain tissues or cells that are intact, fragmented, or partially degraded.

Single-chain variable fragment (scFv): As used herein, the term "single-chain variable fragment" or "scFv" refers to a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the VH with the C-terminus of the VL, or the C-terminus of the VH with the N-terminus of the VL. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80 (6): 1910-1917 (2008) and WO 2014/087010, the contents of which are hereby incorporated by reference in their entireties.

Subject: The term "subject," as used herein, generally refers to an individual having a biological sample that is undergoing processing or analysis and, in specific cases, has or is suspected of having cancer. The subject can be any organism or animal subject that is an object of a method or material, including mammals, e.g., humans, laboratory animals (e.g., primates (such as an ape, monkey, orangutan, or chimpanzee), rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as benign or malignant neoplasia, or cancer. The subject may be undergoing or have undergone treatment. The subject may be asymptomatic. The subject may be healthy individuals but that are desirous of prevention of cancer. The term "individual" may be used interchangeably, in at least some cases. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants and includes in utero individuals. It is not intended that the term connote a need for medical treatment, therefore, an individual may voluntarily or involuntarily be part of experimentation whether clinical or in support of basic science studies.

Target: As used herein, a "target" is any molecule specifically bound by a binding moiety of an antibody or an antigen-binding fragment thereof. In some embodiments, a target is an antigen described herein (e.g., BCMA). In some embodiments, a target is an FcR (e.g., FcRn). The terms "first target" and "second target" are used herein to refer to molecules of two distinct molecular species, rather than two molecules of the same molecular species. For example, in some embodiments, a first target is a serum protein and a second target is FcRn.

Therapeutically effective amount: As used herein, the term "therapeutically effective amount" refers to an amount of a therapeutic molecule (e.g., an anti-BCMA antibody described herein) which confers a therapeutic effect on a treated subject, at a reasonable benefit/risk ratio applicable to any medical treatment. Therapeutic effect may be objective (i.e., measurable by some test or marker) or subjective (i.e., subject gives an indication of or feels an effect). In particular, the "therapeutically effective amount" refers to an amount of a therapeutic molecule or composition effective to treat, ameliorate, or prevent a particular disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount can be administered in a dosing regimen that may comprise multiple unit doses. For any particular therapeutic molecule, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific therapeutic molecule employed; the duration of the treatment; and like factors as is well known in the medical arts.

Treatment: As used herein, the term "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof. As non-limiting examples, the treatment may refer to any administration of a therapeutic molecule (e.g., an anti-BCMA antibodies and BCMA binding CARs described herein) that partially or completely alleviates, ameliorates, relieves, inhibits, delays onset of, reduces severity of and/or reduces incidence of one or more symptoms or features of a particular disease, disorder, and/or condition, e.g., BCMA positive cancers. In some cases, a treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Tumor antigen: As used herein, a "tumor antigen" means a biological molecule having antigenicity, the expression of which causes cancer.

Any method in the context of a therapeutic, diagnostic, or physiologic purpose or effect may also be described in "use" claim language such as "Use of" any compound, composition, or agent discussed herein for achieving or implementing a described therapeutic, diagnostic, or physiologic purpose or effect.

I. Antibodies

The present disclosure is based, in part, on the discovery of engineered antibodies and antigen binding fragments thereof that exhibit binding to BCMA (e.g., human BCMA). BCMA is a protein with a single transmembrane domain, a cytoplasmic C-terminus, and extracellular N-terminus. BCMA is preferentially expressed in by mature B lymphocytes, and its overexpression and activation are associated with enhanced expression of genes critical for survival, growth, adhesion, osteoclast activation, angiogenesis, metastasis, and immunosuppression. There is evidence for BCMA expression in various hematologic malignancies, suggesting that BCMA may play an important role as a biomarker or therapeutic target in these diseases.

Anti-BCMA antibodies described herein are designed to bind to BCMA. In certain embodiments, the presently disclosed anti-BCMA antibodies and fragments thereof bind to human BCMA. In certain embodiments, the human BCMA comprises or consists of the amino acid sequence with a Uniprot Reference No: Q02223 (SEQ ID NO: 22), or a fragment thereof. SEQ ID NO: 22 is provided below:

```
                                      (SEQ ID NO: 22)
MLQMAGQCSQNEYFDSLLHACIPCQLRCSSNTPPLTCQRYCNASVTNSV

KGTNAILWTCLGLSLIISLAVFVLMFLLRKINSEPLKDEFKNTGSGLLG

MANIDLEKSRTGDEIILPRGLEYTVEECTCEDCIKSKPKVDSDHCFPLP

AMEEGATILVTTKTNDYCKSLPAALSATEIEKSISAR
```

In certain embodiments, the anti-BCMA antibodies and antigen binding fragments thereof described herein, bind to the extracellular domain of BCMA. In certain embodiments, the anti-BCMA antibodies and antigen binding fragments thereof bind to the extracellular domain of human BCMA. In certain embodiments, the extracellular domain of human BCMA comprises or consists of amino acids 1 to 54 of SEQ ID NO: 22.

In certain embodiments, the BCMA protein comprises or consists of an amino acid sequence that is at least about 80%, at least about 85%, at least about 90%, at least about 95%, at least about 96%, at least about 97%, at least about 98%, at least about 99%, or at least about 100% identical to the amino acid sequence set forth in SEQ ID NO: 22 or a fragment thereof.

An anti-BCMA antibody described herein can be an immunoglobulin, heavy chain antibody, light chain antibody, LRR-based antibody, or other protein scaffold with antibody-like properties, as well as other immunological binding moiety known in the art, including, e.g., a Fab, Fab', Fab'2, Fab$_2$, Fab$_3$, F(ab')$_2$, Fd, Fv, Feb, scFv, SMIP, antibody, diabody, triabody, tetrabody, minibody, maxibody, tandab, DVD, BiTe, TandAb, or the like, or any combination thereof. The subunit structures and three-dimensional configurations of different classes of antibodies are known in the art.

An antibody can be an immunoglobulin molecule of four polypeptide chains, e.g., two heavy (H) chains and two light (L) chains. A heavy chain can include a heavy chain variable domain and a heavy chain constant domain. A heavy chain constant domain can include CH1, hinge, CH2, CH3, and in some instances CH4 regions. A suitable heavy chain constant region may be derived from any immunoglobulin (e.g., IgA, IgG, or IgE). In some embodiments, a suitable heavy chain constant region may be derived from IgG1, IgG2, or IgG4. In particular embodiments, a suitable heavy chain constant region is derived from IgG1. A light chain can include a light chain variable domain and a light chain constant domain. A light chain constant domain can include either a kappa light chain or a lambda light chain. A heavy chain variable domain of a heavy chain and a light chain variable domain of a light chain can typically be further subdivided into regions of variability, termed complementarity determining regions (CDRs), interspersed with regions that are more conserved, termed framework regions (FR). Such heavy chain and light chain variable domains can each include three CDRs and four framework regions, arranged from amino-terminus to carboxyl-terminus in the following order: FR1, CDR1, FR2, CDR2, FR3, CDR3, FR4, one or more of which can be engineered as described herein. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al. *Nature* 342:878-883 (1989). As used herein, CDRs are referred to for each of the heavy (HCDR1, HCDR2, HCDR3) and light (LCDR1, LCDR2, LCDR3) chains.

Embodiments of the invention include antibodies comprising the CDRs found in the vH and vL domains described herein that are identified using conventional numbering systems, such as the IMGT, Kabat and Chothia numbering systems. Such numbering systems are well-known in the art.

Heavy Chain Variable Region

In some embodiments, the anti-BCMA antibodies or fragments thereof described herein comprise a common heavy chain variable region. In some embodiments, the anti-BCMA antibody comprises heavy chain variable region (VH) complementarity determining region (CDR) sequences:

```
vHCDR1:
                                         (SEQ ID NO: 2)
SYAIH vHCDR2:
                                         (SEQ ID NO: 3)
VTWHDGSNKYYAESVMG vHCDR3:
                                         (SEQ ID NO: 4)
AKFGEPQYFQH
```

In certain embodiments, the CDRs are identified according to the Kabat numbering system.

In some embodiments, the heavy chain variable region (VH) comprises an amino acid sequence of QITLRESGGDVVQPGRSLRLSCAASGFTFSSYAIHWVRQAPGKGLEWVAVTWHDGSNK YYAESVMGRFTISRDNSKNTLYLHMNSLRAEDTGVYYCARAKFGEPQYFQHWGQGTL VTVSS (SEQ ID NO: 1).

In some embodiments, the anti-BCMA antibody comprises a heavy chain amino acid sequence having at least 70%, 75%, 80%, 85%, 90%, 91%, 92%, 93%, 94%, 95%, 96%, 97%, 98%, or 99% sequence identity to:

```
                                        (SEQ ID NO: 54)
QITLRESGGDVVQPGRSLRLSCAASGFTFSSYAIHWVRQAPGKGLEWVA

VTWHDGSNKYYAESVMGRFTISRDNSKNTLYLHMNSLRAEDTGVYYCAR

AKFGEPQYFQHWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPG.
```

In some embodiments, the anti-BCMA antibody comprises a heavy chain amino acid sequence having at least 70%, 75%, 80%, 85%, 90%, 91%, 92%, 93%, 94%, 95%, 96%, 97%, 98%, or 99% sequence identity to SEQ ID NO: 54 while also including one or more of the vH CDR1, vHCDR2, and/or vHCDR3 sequences described herein.

In some embodiments, the engineered antibodies comprise a heavy chain variable region having an amino acid sequence identical to SEQ ID NO: 1. In certain embodiments, the VH comprises an amino acid sequence that is at least about 70%, 75%, 80% (e.g., at least about 85%, at least about 90%, or at least about 95%) identical or homologous to the amino acid sequence set forth in SEQ ID NO: 1. For example, the VH comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 1. In some embodiments, the anti-BCMA antibody comprises no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NO: 1.

In some embodiments, the anti-BCMA variable heavy chain region is encoded by a polynucleotide that comprises the nucleic acid sequence of:

(SEQ ID NO: 55)
cagatcactttaagggagagcggaggcgatgtggtgcagcccggtcgtt ctttaagactgagctgtgccgccagcggcttcaccttcagcagctacgc catccactgggtgagacaagctcccggtaaaggtttagagtgggtggct gtgacttggcacgacggctccaacaagtactatgccgagagcgtgatgg gtcgtttcaccatctctcgtgacaacagcaagaacactttatatttaca catgaactctttaagggccgaggacaccggcgtgtactactgcgccaga gccaagttcggcgagccccagtacttccagcactggggccaaggtacac tggtgaccgtgtccagc In some embodiments, the anti-BCMA antibody heavy chain is encoded by a polynucleotide comprising a nucleic acid sequence having at least 70%, 75%, 80%, 85%, 90%, 91%, 92%, 93%, 94%, 95%, 96%, 97%, 98%, or 99% sequence identity to SEQ ID NO: 56:

(SEQ ID NO: 56)
cagatcactttaagggagagcggaggcgatgtggtgcagcccggtcgtt ctttaagactgagctgtgccgccagcggcttcaccttcagcagctacgc catccactgggtgagacaagctcccggtaaaggtttagagtgggtggct gtgacttggcacgacggctccaacaagtactatgccgagagcgtgatgg gtcgtttcaccatctctcgtgacaacagcaagaacactttatatttaca catgaactctttaagggccgaggacaccggcgtgtactactgcgccaga gccaagttcggcgagccccagtacttccagcactggggccaaggtacac tggtgaccgtgtccagcgctagcaccaagggcccatcggtcttcccct ggcaccctcctccaagagcacctctgggggcacagcggccctgggctgc gaccctgaggtcaagttcaactggtacgtggacggcgtggaggtgcata actggtcaaggactacttccccgaaccggtgacggtgtcgtggaactca ggcgccctgaccagcggcgtgcacaccttcccggctgtcctacagtcct caggactctactccctcagcagcgtggtgaccgtgccctccagcagctt gggcacccagacctacatctgcaacgtgaatcacaagcccagcaacacc aaggtggacaagagagttgagcccaaatcttgtgacaaaactcacacat gcccaccgtgcccagcacctgaactcctgggggggaccgtcagtcttcct cttcccccaaaacccaaggacaccctcatgatctcccggacccctgag gtcacatgcgtggtggtggacgtgagccacgaatgccaagacaaagccg cgggaggagcagtacaacagcacgtaccgtgtggtcagcgtcctcaccg tcctgcaccaggactggctgaatggcaaggagtacaagtgcaaggtctc caacaaagccctcccagccccatcgagaaaaccatctccaaagccaaa gggcagccccgagaaccacaggtgtataccctgccccatcccgggagg agatgaccaagaaccaggtcagcctgacctgcctggtcaaaggcttcta tcccagcgacatcgccgtggagtgggagagcaatgggcagccggagaac aactacaagaccacgcctcccgtgctggactccgacggctccttcttcc tctatagcaagctcaccgtggacaagagcaggtggcagcaggggaacgt cttctcatgctccgtgatgcatgaggctctgcacaaccactacacgcag aagagcctctccctgtccccgggt In some embodiments, the engineered antibodies comprise a heavy chain that is encoded by a polynucleotide having a nucleic acid sequence identical to SEQ ID NO: 56. In some embodiments, the anti-BCMA antibody comprises a nucleic acid sequence that encodes an antibody comprising no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NO: 54.

In some embodiments, the anti-BCMA antibody is encoded by a polynucleotide that comprises a nucleic acid sequence encoding a heavy chain amino acid sequence having at least 70%, 75%, 80%, 85%, 90%, 91%, 92%, 93%, 94%, 95%, 96%, 97%, 98%, or 99% sequence identity to SEQ ID NO: 9, while also including one or more of the vHCDR1, vHCDR2, and/or vHCDR3 sequences described herein.

In some embodiments, the anti-BCMA antibodies or fragments thereof described herein comprise a common heavy chain variable region. In some embodiments, the anti-BCMA antibody comprises heavy chain variable region (VH) complementarity determining region (CDR) sequences:

vHCDR1:
(SEQ ID NO: 2)
SYAIH vHCDR2:
(SEQ ID NO: 3)
VTWHDGSNKYYAESVMG vHCDR3:
(SEQ ID NO: 4)
AKFGEPQYFQH

In certain embodiments, the CDRs are identified according to the Kabat numbering system.

In some embodiments, the variable region of the heavy chain comprises an amino acid sequence of EVOLVESGGDVVQPGRSLRLSCAASGFTFSSYAIHWVRQAPGKGLEWVAVTWHDGSN KYYAESVMGRFTISRDNSKNTLYLHMNSLRAEDTGVYYCARAKFGEPQYFQHWGQGT TVTVSS (SEQ ID NO: 9).

In some embodiments, the anti-BCMA antibody comprises a heavy chain comprising an amino acid sequence having at least 70%, 75%, 85%, 90%, 91%, 92%, 93%, 94%, 95%, 96%, 97%, 98%, or 99% sequence identity to:

(SEQ ID NO: 57)
EVQLVESGGDVVQPGRSLRLSCAASGFTFSSYAIHWVRQAPGKGLEWVA

VTWHDGSNKYYAESVMGRFTISRDNSKNTLYLHMNSLRAEDTGVYYCAR

AKFGEPQYFQHWGQGTTVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPG.

In some embodiments, the anti-BCMA antibody comprises a heavy chain amino acid sequence having at least 70%, 75%, 80%, 85%, 90%, 91%, 92%, 93%, 94%, 95%, 96%, 97%, 98%, or 99% sequence identity to SEQ ID NO: 57 while also including one or more of the vHCDR1, vHCDR2, and/or vHCDR3 sequences described herein.

In some embodiments, the engineered antibodies comprise a heavy chain amino acid sequence identical to SEQ ID NO: 57. In certain embodiments, the VH comprises an amino acid sequence that is at least about 70% (e.g., at least about 75%, at least about 80%, at least about 85%, at least about 90%, or at least about 95%) identical or homologous to the amino acid sequence set forth in SEQ ID NO: 9. For example, the VH comprises an amino acid sequence that is about 70%, 75%, 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 9. In some embodiments, the anti-BCMA antibody comprises no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NO: 9.

In some embodiments, the anti-BCMA variable heavy chain is encoded by a polynucleotide that comprises the nucleic acid sequence of:

(SEQ ID NO: 58)
gaggtgcagttagtggagagcggaggcgatgtggtgcagcccggtcgtt ctttaagactgagctgtgccgccagcggcttcaccttcagcagtacgc catccactgggtgagacaagctcccggtaaaggtttagagtgggtggct gtgacttggcacgacggctccaacaagtactatgccgagagcgtgatgg gtcgtttcaccatctctcgtgacaacagcaagaacactttatatttaca catgaactctttaagggccgaggacaccggcgtgtactactgcgccaga gccaagttcggcgagcccagtacttccagcactggggccaaggtacaa ccgtgaccgtgtccagc In some embodiments, the polynucleotide encoding the anti-BCMA antibody comprises a heavy chain nucleic acid sequence having at least 70%, 75%, 80%, 85%, 90%, 91%, 92%, 93%, 94%, 95%, 96%, 97%, 98%, or 99% sequence identity to:

(SEQ ID NO: 59)
gaggtgcagttagtggagagcggaggcgatgtggtgcagcccggtcgtt ctttaagactgagctgtgccgccagcggcttcaccttcagcagtacgc catccactgggtgagacaagctcccggtaaaggtttagagtggggctg tgacttggcacgacggctccaacaagtactatgccgagagcgtgatggg tcgtttcaccatctctcgtgacaacagcaagaacactttatatttacac atgaactctttaagggccgaggacaccggcgtgtactactgcgccagag ccaagttcggcgagcccagtacttccagcactggggccaaggtacaac cgtgaccgtgtccagcgctagcaccaagggcccatcggtcttccccctg gcacctcctccaagagcacctctgggggcacagcggccctgggctgcc tggtcaaggactacttccccgaaccggtgacggtgtcgtggaactcagg cgccctgaccagcggcgtgcacaccttcccggctgtcctacagtcctca ggactctactcctcagcagcgtggtgaccgtgccctccagcagcttgg gcacccagacctacatctgcaacgtgaatcacaagcccagcaacaccaa ggtggacaagagagttgagcccaaatcttgtgacaaaactcacacatgc ccaccgtgcccagcacctgaactcctgggggaccgtcagtcttcctct tccccccaaaacccaaggacaccctcatgatctcccggacccctgaggt cacatgcgtggtggtggacgtgagccacgaagaccctgaggtcaagttc aactggtacgtggacggcgtggaggtgcataatgccaagacaaagccgc gggaggagcagtacaacagcacgtaccgtgtggtcagcgtcctcaccgt cctgcaccaggactggctgaatggcaaggagtacaagtgcaaggtctcc aacaaagccctcccagcccccatcgagaaaaccatctccaaagccaaag ggcagccccgagaaccacaggtgtataccctgcccccatcccgggagga gatgaccaagaaccaggtcagcctgacctgcctggtcaaaggcttctat cccagcgacatcgccgtggagtgggagagcaatgggcagccggagaaca actacaagaccacgcctcccgtgctggactccgacggctccttcttcct ctatagcaagctcaccgtggacaagagcaggtggcagcaggggaacgtc ttctcatgctccgtgatgcatgaggctctgcacaaccactacacgcaga agagcctctccctgtccccgggt In some embodiments, the engineered antibodies comprise a heavy chain nucleic acid sequence identical to SEQ ID NO: 59. In some embodiments, the anti-BCMA antibody comprises a nucleic acid sequence that encodes an antibody comprising no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NO: 9.

In some embodiments, the anti-BCMA antibody is encoded by a polynucleotide that comprises a nucleic acid sequence encoding a heavy chain amino acid sequence having at least 70%, 75%, 80%, 85%, 90%, 91%, 92%, 93%, 94%, 95%, 96%, 97%, 98%, or 99% sequence identity to SEQ ID NO: 59, while also including one or more of the vHCDR1, vHCDR2, and/or vHCDR3 sequences described herein.

TABLE 1

Anti-BCMA heavy chain variable CDRs and VH

| Ab # | VH | SEQ ID NO: | HCDR1 | SEQ ID NO: | HCDR2 | SEQ ID NO: | HCDR3 | SEQ ID NO: |
|---|---|---|---|---|---|---|---|---|
| 1 | QITLRESGGDVVQPGRSLR LSCAASGFTFSSYAIHWVR QAPGKGLEWVAVTWHDG SNKYYAESVMGRFTISRDN SKNTLYLHMNSLRAEDTG VYYCARAKFGEPQYFQHW GQGTLVTVSS | 1 | SYAIH | 2 | VTWHDGSNKYYAE SVMG | 3 | AKFGEPQYFQH | 4 |

NUCLEIC ACID SEQUENCE

| 1 | cagatcactttaagggagagcggaggcg atgtggtgcagcccggtcgttctttaagac tgagctgtgccgccagcggcttcaccttc agcagctacgccatccactgggtgagac aagctcccggtaaaggtttagagtgggtg gctgtgacttggcacgacggctccaacaa gtactatgccgagagcgtgatgggtcgttt caccatctctcgtgacaacagcaagaaca ctttatatttacacatgaactcttttaagggcc gaggacaccggcgtgtactactgcgcca gagccaagttcggcgagccccaotacttc cagcactggggccaaggtacactggtga ccgtgtccagc | 55 | agctacgc catccac | 60 | gtgacttggc acgacggctcca acaagtacta tgccgagagcgt gatgggt | 61 | gccaagttcggcgagcc ccagtacttccagcac | 62 |

| 2 | QITLRESGGDVVQPGRSLR LSCAASGFTFSSYAIHWVR QAPGKGLEWVAVTWHDG SNKYYAESVMGRFTISRDN SKNTLYLHMNSLRAEDTG VYYCARAKFGEPQYFQHW GQGTLVTVSS | 1 | SYAIH | 2 | VTWHDGSNKYYAE SVMG | 3 | AKFGEPQYFQH | 4 |

NUCLEIC ACID SEQUENCE

| 2 | cagatcactttaagggagagcggaggcg atgtggtgcagcccggtcgttctttaagac tgagctgtgccgccagcggcttcaccttc agcagctacgccatccactgggtgagac aagctcccggtaaaggtttagagtgggtg gctgtgacttggcacgacggctccaacaa gtactatgccgagagcgtgatgggtcgttt caccatctctcgtgacaacagcaagaaca ctttatatttacacatgaactcttttaagggcc gaggacaccggcgtgtactactgcgcca gagccaagttcggcgagccccagtacttc cagcactggggccaaggtacactggtga ccgtgtccagc | 55 | agctacgc catccac | 60 | gtgacttggca cgacggctcca acaagtacta tgccgagagcgt gatgggt | 61 | gccaagttcggcgagcc ccagtacttccagcac | 62 |

| 3 | EVOLVESGGDVVQPGRSL RLSCAASGFTFSSYAIHWV RQAPGKGLEWVAVTWHD GSNKYYAESVMGRFTISRD NSKNTLYLHMNSLRAEDT GVYYCARAKFGEPQYFQH WGQGTTVTVSS | 9 | SYAIH | 2 | VTWHDGSNKYYAE SVMG | 3 | AKFGEPQYFQH | 4 |

NUCLEIC ACID SEQUENCE

| 3 | gaggtgcagttagtggagagcggaggc gatgtggtgcagcccggtcgttctttaaga ctgagctgtgccgccagcggcttcaccttt cagcagctacgccatccactgggtgaga caagctcccggtaaaggtttagagtgggt ggctgtgacttggcacgacggctccaac aagtactatgccgagagcgtgatgggtcg | 58 | Agctacgc catccac | 60 | gtgacttggca cgacggctcca acaagtacta tgccgagagcgt gatgggt | 61 | gccaagttcggcgagcc ccagtacttccagcac | 62 |

TABLE 1-continued

Anti-BCMA heavy chain variable CDRs and VH

| Ab # | VH | SEQ ID NO: | HCDR1 | SEQ ID NO: | HCDR2 | SEQ ID NO: | HCDR3 | SEQ ID NO: |
|---|---|---|---|---|---|---|---|---|
| | tttcaccatctctcgtgacaacagcaagaa cactttatatttacacatgaactctttaaggg ccgaggacaccggcgtgtactactgcgc cagagccaagttcgocgagcccagtac ttccagcactggggccaaggtacaaccgt gaccgtgtccagc | | | | | | | |

As will be understood by those of skill in the art, any such heavy chain CDR sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

In various engineered antibodies described herein, a heavy chain constant domain can be of any class (or subclass). In various engineered antibodies described herein, a heavy chain constant domain can include the amino acid sequence of any of one or more of IgG, IgM, IgA, IgD, or IgE, including subclasses such as IgG1, IgG2, IgG3, IgG4, IgA1, and IgA2. In various embodiments, a constant domain of engineered antibodies described herein can include a mixture of two or more classes (or subclasses) of immunoglobulin heavy chain constant domain. For example, an anti-BCMA antibody can include a first portion of a constant domain that has a sequence of an immunoglobulin constant domain selected from an IgG, IgM, IgA, IgD, or IgE class constant domain and a second portion of a constant domain that has a sequence of an immunoglobulin constant domain different from the first and selected from an IgG, IgM, IgA, IgD, or IgE class constant domain. In some instances, a constant domain of an anti-BCMA antibody described herein can include a mixture of two or more subclasses of a particular class of constant domain, e.g., a first portion of a constant domain that has a sequence of an immunoglobulin constant domain selected from an IgG1, IgG2, IgG3, or IgG4 subclass constant domain and a second portion of a constant domain that has a sequence of an immunoglobulin constant domain different from the first and selected from an IgG1, IgG2, IgG3, or IgG4 subclass constant domain. In some particular embodiments, a constant domain includes all or a portion of an IgG2 constant domain and all or a portion of an IgG4 constant domain.

In some instances, an anti-BCMA antibody includes an antibody constant region, Fc region or Fc fragment that exhibits altered binding (as compared to a reference constant region) to one or more Fc receptors (e.g., FcγRI, FcγRIIA, FcγRIIB, FcγRIIIA, FcγRIIIB, FcγRIV, or FcRn receptor). In some embodiments, an anti-BCMA antibody includes an antibody constant region, Fc region or Fc fragment that exhibits decreased binding (as compared to a reference constant region) to one or more Fcγ receptor (e.g., FcγRI, FcγRIIA, FcγRIIB, FcγRIIIA, FcγRIIIB, or FcγRIV). In some embodiments, anti-BCMA antibody includes an antibody constant region, Fc region or Fc fragment that exhibits increased binding to the FcRn receptor (as compared to a reference constant region) at serum pH and/or at intracellular pH.

For example, an anti-BCMA antibody can include a constant region, Fc region or Fc fragment of an IgG antibody engineered to include an amino acid addition, deletion, or substitution, of one or more of amino acid residues 251-256, 285-290, 308-314, 385-389, and 428-436 (Kabat numbering (Kabat et al., (1991) Sequences of Proteins of Immunological Interest, NIH)). Without wishing to be bound by theory, it is believed that one or more of these constant region, Fc region, or Fc fragment amino acids mediate interaction with an Fc receptor, e.g., FcRn. In some embodiments, one or more of these disclosed amino acids is substituted with histidine, arginine, lysine, aspartic acid, glutamic acid, serine, threonine, asparagine, or glutamine. In some embodiments, a non-histidine residue is substituted with a histidine residue. In some embodiments, a histidine residue is substituted with a non-histidine residue.

In some embodiments, an anti-BCMA antibody includes a constant region, Fc region or Fc fragment of an IgG antibody having amino acid modifications at one or more of positions 308, 309, 311, 312, and 314. In some embodiments, the substitutions at one or more of positions 308, 309, 311, 312 and 314 with threonine, proline, serine, aspartic acid and leucine respectively. In some embodiments, residues at one or more of positions 308, 309, and 311 are substituted with isoleucine, proline, and glutamic acid, respectively. In yet other embodiments, residues at one or more of positions 308, 309, 311, 312, and 314, are substituted with threonine, proline, serine, aspartic acid, and leucine, respectively.

In some embodiments, an anti-BCMA antibody includes a constant region, Fc region or Fc fragment of an IgG antibody having amino acid modifications at one or more of positions 251, 252, 254, 255, and 256, more specifically, having substitutions at one or more of these positions. In some embodiments, residue 251 is substituted with leucine or arginine, residue 252 is substituted with leucine, tyrosine, phenylalanine, serine, tryptophan or threonine, residue 254 is substituted with threonine or serine, residue 255 is substituted with leucine, glycine, isoleucine or arginine, and/or residue 256 is substituted with serine, phenylalanine, arginine, glutamine, glutamic acid, aspartic acid, alanine, asparagine or threonine. In some embodiments, residue 251 is substituted with leucine, residue 252 is substituted with tyrosine or leucine, residue 254 is substituted with threonine or serine, and/or residue 255 is substituted with arginine. In yet other embodiments, residue 252 is substituted with phenylalanine and/or residue 256 is substituted with aspartic acid. In some embodiments, residue 251 is substituted with leucine, residue 252 is substituted with tyrosine, residue 254 is substituted with threonine or serine, and/or residue 255 is substituted with arginine.

In some embodiments, an anti-BCMA antibody includes a constant region, Fc region or Fc fragment of an IgG antibody having amino acid modifications at one or more of positions 428, 433, 434, 435, and 436, more specifically, having substitutions at one or more of these positions. In some embodiments, residue 428 is substituted with methionine, threonine, leucine, phenylalanine, or serine, residue 433 is substituted with lysine, arginine, serine, isoleucine, proline, glutamine, or histidine, residue 434 is substituted with phenylalanine, tyrosine, or histidine, residue 435 is substituted with tyrosine, and/or residue 436 is substituted with histidine, asparagine, arginine, threonine, lysine, methionine, or threonine. In some embodiments, residues at one or more positions 433, 434, 435, and 436 are substituted with lysine, phenylalanine, tyrosine, and histidine, respectively. In some embodiments, residue 428 is substituted with methionine and/or residue 434 is substituted with tyrosine.

In some embodiments, an anti-BCMA antibody includes a constant region, Fc region or Fc fragment of an IgG antibody having amino acid modifications at one or more of positions 385, 386, 387, and 389, more specifically, having substitutions at one or more of these positions. In some embodiments, residue 385 is substituted with arginine, aspartic acid, serine, threonine, histidine, lysine, or alanine, residue 386 is substituted with threonine, proline, aspartic acid, serine, lysine, arginine, isoleucine, or methionine, residue 387 is substituted with arginine, histidine, serine, threonine, alanine, or proline and/or residue 389 is substituted with proline or serine. In some embodiments, residues at one or more of positions 385, 386, 387, and 389 are substituted with arginine, threonine, arginine, and proline, respectively. In some embodiments, residues at one or more of positions 385, 386, and 389 are substituted with aspartic acid, proline, and serine, respectively.

In some embodiments, an anti-BCMA antibody includes a constant region, Fc region or Fc fragment of an IgG antibody having one or more of the following substitutions: leucine at residue 251, tyrosine or leucine at residue 252, threonine or serine at residue 254, arginine at residue 255, threonine at residue 308, proline at residue 309, serine at residue 311, aspartic acid at residue 312, leucine at residue 314, arginine at residue 385, threonine at residue 386, arginine at residue 387, proline at residue 389, methionine at residue 428, lysine at residue 433, phenylalanine or tyrosine at residue 434, tyrosine at position 435, and/or tyrosine at position 436. Additional amino acid substitutions that can be included in a constant region, Fc region or Fc fragment include those described in, e.g., U.S. Pat. Nos. 6,277,375; 8,012,476; and 8,163,881.

In some embodiments, an anti-BCMA antibody described herein includes a heavy chain constant domain that includes the Ala-Ala mutation described in, e.g., PCT Publication nos. WO 94/28027 and WO 98/47531; and Xu et al. (2000) Cell Immunol 200:16-26. Thus, in some embodiments, an anti-BCMA antibody with one or more mutations within the heavy chain constant region including the Ala-Ala mutation has reduced or no effector function. According to these embodiments, the constant region of an anti-BCMA antibody described herein can comprise a substitution to an alanine at position 234 and/or a mutation to an alanine at position 235 (EU numbering).

As will be understood by those of skill in the art, any such heavy chain constant domain sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

Light Chain Variable Region

Also provided are BCMA antibodies or fragment thereof comprising various specified sequences in one or more light chain variable regions, including in the light chain complementary determining regions LCDR1-3. In various embodiments, molecules with specified light chain variable regions are provided with heavy chain sequences as discussed above. In certain embodiments, the CDRs are identified according to the Kabat numbering system.

Thus in some aspects, the present invention provide an anti-BCMA antibody or antigen binding fragment thereof comprising a light chain variable region with complementarity determining region (CDR) sequences of RASQGISSYLA (SEQ ID NO: 11) (LCDR1), AASTLQS (SEQ ID NO: 7) (LCDR2), and QQLNSYPWT (SEQ ID NO: 14) (LCDR3).

In some embodiments, the present invention provide an anti-BCMA antibody or antigen binding fragment thereof comprising a light chain variable region with complementarity determining region (CDR) sequences of RASQGINNYLA (SEQ ID NO: 6) (LCDR1), AASTLQS (SEQ ID NO: 7) (LCDR2), and QQLKSYPFT (SEQ ID NO: 8) (LCDR3).

In some embodiments, the present invention provide an anti-BCMA antibody or antigen binding fragment thereof comprising a light chain variable region with complementarity determining region (CDR) sequences of RASQGISSYLA (SEQ ID NO: 11) (LCDR1), AASTLQS (SEQ ID NO: 7) (LCDR2), and QQLNSYPFT (SEQ ID NO: 12) (LCDR3).

In some embodiments, the present invention provide an anti-BCMA antibody or antigen binding fragment thereof comprising a light chain variable region (VL) comprising an amino acid sequence of SEQ ID NO: 5, 10 or 13.

In some examples, the present invention provides a BCMA antibody or fragment thereof comprising a heavy chain variable complementarity determining region (CDR) sequences of SYAIH (SEQ ID NO: 2) (HCDR1), VTWHDGSNKYYAESVMG (SEQ ID NO: 3) (HCDR2) and AKFGEPQYFQH (SEQ ID NO: 4) (HCDR3) and a light chain variable region with complementarity determining region (CDR) sequences of RASQGISSYLA (SEQ ID NO: 11) (LCDR1), AASTLQS (SEQ ID NO: 7) (LCDR2), and QQLNSYPWT (SEQ ID NO: 14) (LCDR3).

In some embodiments, the BCMA antibody or fragment thereof comprises a heavy chain variable complementarity determining region (CDR) sequences of SYAIH (SEQ ID NO: 2) (HCDR1), VTWHDGSNKYYAESVMG (SEQ ID NO: 3) (HCDR2) and AKFGEPQYFQH (SEQ ID NO: 4) (HCDR3) and a light chain variable region with complementarity determining region (CDR) sequences of RASQGINNYLA (SEQ ID NO: 6) (LCDR1), AASTLQS (SEQ ID NO: 7) (LCDR2), and QQLKSYPFT (SEQ ID NO: 8) (LCDR3).

In some embodiments, the BCMA antibody or fragment thereof comprises a heavy chain variable complementarity determining region (CDR) sequences of SYAIH (SEQ ID NO: 2) (HCDR1), VTWHDGSNKYYAESVMG (SEQ ID NO: 3) (HCDR2) and AKFGEPQYFQH (SEQ ID NO: 4) (HCDR3) and a light chain variable region with complementarity determining region (CDR) sequences of RASQGISSYLA (SEQ ID NO: 11) (LCDR1), AASTLQS (SEQ ID NO: 7) (LCDR2), and QQLNSYPFT (SEQ ID NO: 12) (LCDR3).

In some embodiments, the BCMA antibody or fragment thereof comprises an immunoglobulin light chain variable (VL) region comprising an amino acid sequence that is at least 70%, 75%, 80%, 85%, 90%, 95%, 99% identical to SEQ ID NO: 5; and an immunoglobulin heavy chain variable (VH) region comprising an amino acid sequence that is at least 70%, 75%, 80%, 85%, 90%, 95%, 99% identical to SEQ ID NO: 1.

In some embodiments, the BCMA antibody or fragment thereof comprises an immunoglobulin light chain variable (VL) region comprising a nucleic acid sequence that is at least 70%, 75%, 80%, 85%, 90%, 95%, 99% identical to SEQ ID NO: 10; and an immunoglobulin heavy chain variable (VH) region comprising a nucleic acid sequence that is at least 70%, 75%, 80%, 85%, 90%, 95%, 99% identical to SEQ ID NO: 9.

In some embodiments, the BCMA antibody or fragment thereof comprises an immunoglobulin light chain variable (VL) region comprising an amino acid sequence that is at least 70%, 75%, 80%, 85%, 90%, 95%, 99% identical to SEQ ID NO: 13; and an immunoglobulin heavy chain variable (VH) region comprising an amino acid sequence that is at least 70%, 75%, 80%, 85%, 90%, 95%, 99% identical to SEQ ID NO: 1.

In some embodiments, the anti-BCMA antibody or fragment thereof comprises a light chain variable region (VL) and/or LCDRs with an amino acid sequences shown in Table 2.

TABLE 2

Anti-BCMA light chain variable CDRs and VL.

| Ab # | VL | SEQ ID NO | LCDR1 | SEQ ID NO: | LCDR2 | SEQ ID NO: | LCDR3 | SEQ ID NO: |
|---|---|---|---|---|---|---|---|---|
| 1 | DIVMTQSPSFLSASVGDRVTITCRASQGISSYLAWYQQKPGKAPKLLIYAASTLQSGVPSRFSGSGSGTEFTLTISSLQPEDFATYYCQQLNSYPWTFGQGTKVDIK | 13 | RASQGISSYLA | 11 | AASTLQS | 7 | QQLNSYPWT | 14 |

NUCLEIC ACID SEQUENCE

| 1 | gacatcgtgatgacccagagccccagctttctgagcgccagcgtgggcgatcgtgtgaccatcacttgtcgtgccagccaaggtatcagcagctatttagcttggtaccagcagaagcccggcaaggcccccaagctgctgatctacgccgccagcactttacagagcggcgtgccttctcgttttttctggcagcggctctggcaccgagttcactttaaccatcagctctttacagcccgaggacttcgccacctattactgccagcagctgaactcctacccttggaccttcggccaaggtaccaaggtggacatcaag | 63 | cgtgccagccaaggtatcagcagctat | 64 | gccgccagcactttacagagc | 65 | cagcagctgaactcctacccttggacc | 66 |

| 2 | DIVMTQSPSFLSASVGDRVTITCRASQGINNYLAWYQQKPGIAPKLLIYAASTLQSGVPSRFGGSGSGTEFTLTISSLQPEDFATYYCQQLKSYPFTFGPGTKVEIK | 5 | RASQGINNYLA | 6 | AASTLQS | 7 | QQLKSYPFT | 8 |

NUCLEIC ACID SEQUENCE

| 2 | gacatcgtgatgacccagagccctagcttttttaagcgccagcgtgggcgacagagtgaccatcacttgtcgtgccagccaaggtatcaacaactatttagcttggtaccagcagaagcccggtatcgcccccaagctgctgatctacgccgccagcacactgcagagcggcgtgcctagcagatttggtggcagcggctctggcacagagttcactttaaccatcagctctttacagcccgaggacttcgccacctactactgccagcagctgaagagctaccccttcaccttcggccccggcaccaaggtggagatcaag | 67 | cgtgccagccaaggtatcaacaactattagct | 68 | gccgccagcacactgcagagc | 69 | cagcagctgaagagctaccccttcacc | 70 |

| 3 | DIVMTQSPSFLSASVGDRVTITCRASQGISSYLAWYQQKPGKAPKLLIYAASTLQSGVPSRFSGSGSGTEFTLTISSLQPEDFATYYCQQLNSYPFTFGPGTKVDIK | 10 | RASQGISSYLA | 11 | AASTLQS | 7 | QQLNSYPFT | 12 |

TABLE 2-continued

Anti-BCMA light chain variable CDRs and VL.

| Ab # | VL | SEQ ID NO | LCDR1 | SEQ ID NO: | LCDR2 | SEQ ID NO: | LCDR3 | SEQ ID NO: |
|---|---|---|---|---|---|---|---|---|
| | | | | NUCLEIC ACID SEQUENCE | | | | |
| 3 | gacatcgtgatgacccagagccctagcttttaagcg ccagcgtgggcgacagagtgaccatcacttgtcgtg ccagccaaggtatcagcagctatttagcttggtacca gcagaagcccggcaaggcccccaagctgctgatct acgccgccagcactttacagagcggagtgcctagc agattcagcggcagcggctccggcaccgagttcac tttaaccatcagctctttacagcccgaggacttcgcca cctactactgccagcagctgaacagctacccttcac cttcggccccggcaccaaggtggacatcaag | 71 | cgtgcc agccaa ggtatc agcagc tatttagc | 64 | gccgccagc actttacaga gc | 65 | cagcagctgaac agctacccttca cc | 72 |

In some embodiments, the anti-BCMA antibody comprises a variable light chain amino acid sequence having at least 70%, 75%, 80%, 85%, 90%, 91%, 92%, 93%, 94%, 95%, 96%, 97%, 98%, or 99% sequence identity to SEQ ID NO: 5, 10 or 13.

In some embodiments, the anti-BCMA antibody comprises a variable light chain amino acid sequence having at least 70%, 75%, 80%, 85%, 90%, 95%, 98%, or 99% sequence identity to SEQ ID NO: 5, 10 or 13 while also including one or more of the vLCDR1, vLCDR2, and/or vLCDR3 sequences described herein.

In some embodiments, the anti-BCMA antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 73, 74 or 75.

In some embodiments, the anti-BCMA antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 73:

(SEQ ID NO: 73)
DIVMTQSPSFLSASVGDRVTITCRASQGISSYLAWYQQKPGKAPKLLIY

AASTLQSGVPSRFSGSGSGTEFTLTISSLQPEDFATYYCQQLNSYPWTF

GQGTKVDIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, the anti-BCMA antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 74:

(SEQ ID NO: 74)
DIVMTQSPSFLSASVGDRVTITCRASQGINNYLAWYQQKPGIAPKLLIY

AASTLQSGVPSRFGGSGSGTEFTLTISSLQPEDFATYYCQQLKSYPFTF

GPGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, the anti-BCMA antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 75:

(SEQ ID NO: 75)
DIVMTQSPSFLSASVGDRVTITCRASQGISSYLAWYQQKPGKAPKLLIY

AASTLQSGVPSRFSGSGSGTEFTLTISSLQPEDFATYYCQQLNSYPFTF

GPGTKVDIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

In some embodiments, the anti-BCMA antibody comprises a light chain amino acid sequence having at least 70%, 75%, 80%, 85%, 90%, 91%, 92%, 93%, 94%, 95%, 96%, 97%, 98%, or 99% sequence identity to SEQ ID NO: 73, 74 or 75 while also including one or more of the vL CDR1, vLCDR2, and/or vLCDR3 sequences described herein.

In some embodiments, the anti-BCMA antibody or fragment thereof comprises a variable light chain (VL) amino acid sequence identical to SEQ ID NOs: 5, 10 and 13. In some embodiments, the anti-BCMA antibody comprises no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NOs: 5, 10 and 13.

In some embodiments, the anti-BCMA antibody comprises a light chain nucleic acid sequence having at least 70%, 75%, 80%, 85%, 90%, 91%, 92%, 93%, 94%, 95%, 96%, 97%, 98%, or 99% sequence identity to SEQ ID NOs: 76-78. In some embodiments, the engineered antibodies comprise a light chain nucleic acid sequence identical to SEQ ID NO: 76-78.

In some embodiments, the anti-BCMA antibody comprises a light chain nucleic acid sequence having at least 70%, 75%, 80%, 85%, 90%, 91%, 92%, 93%, 94%, 95%, 96%, 97%, 98%, or 99% sequence identity to SEQ ID NO: 76:

(SEQ ID NO: 76)
gacatcgtgatgacccagagccccagctttctgagcgccagcgtgggcg atcgtgtgaccatcacttgtcgtgccagccaaggtatcagcagctattt agcttggtaccagcagaagcccggcaaggcccccaagctgctgatctac gccgccagcactttacagagcggcgtgccttctcgttttctggcagcg gctctggcaccgagttcactttaaccatcagctctttacagcccgagga cttcgccacctattactgccagcagctgaactcctacccttggaccttc ggccaaggtaccaaggtggacatcaagcgtacggtggctgcaccatctg tcttcatcttcccgccatctgatgagcagttgaaatctggaactgcctc tgttgtgtgcctgctgaataacttctatcccagagaggccaaagtacag tggaaggtggataacgccctccaatcgggtaactcccaggagagtgtca cagagcaggacagcaaggacagcacctacagcctcagcagcaccctgac gctgagcaaagcagactacgagaaacacaaagtctacgcctgcgaagtc acccatcagggcctgagctcgcccgtcacaaagagcttcaacaggggag agtgt In some embodiments, the anti-BCMA antibody comprises a light chain nucleic acid sequence having at least 70%, 75%, 80%, 85%, 90%, 91%, 92%, 93%, 94%, 95%, 96%, 97%, 98%, or 99% sequence identity to SEQ ID NO: 77, (SEQ ID NO: 77)
gacatcgtgatgacccagagccctagcttttaagcgccagcgtgggcg acagagtgaccatcacttgtcgtgccagccaaggtatcaacaactattt agcttggtaccagcagaagcccggtatcgcccccaagctgctgatctac gccgccagcacactgcagagcggcgtgcctagcagatttggtggcagcg gctctggcacagagttcactttaaccatcagctctttacagcccgagga cttcgccacctactactgccagcagctgaagagctacccccttcaccttc ggccccggcaccaaggtggagatcaagcgtacggtggctgcaccatctg tcttcatcttcccgccatctgatgagcagttgaaatctggaactgcctc tgttgtgtgcctgctgaataacttctatcccagagaggccaaagtacag tggaaggtggataacgccctccaatcgggtaactcccaggagagtgtca cagagcaggacagcaaggacagcacctacagcctcagcagcaccctgac gctgagcaaagcagactacgagaaacacaaagtctacgcctgcgaagtc acccatcagggcctgagctcgcccgtcacaaagagcttcaacaggggag agtgt In some embodiments, the anti-BCMA antibody comprises a light chain nucleic acid sequence having at least 70%, 75%, 80%, 85%, 90%, 91%, 92%, 93%, 94%, 95%, 96%, 97%, 98%, or 99% sequence identity to SEQ ID NO: 78:

(SEQ ID NO: 78)
gacatcgtgatgacccagagccctagcttttaagcgccagcgtgggcg acagagtgaccatcacttgtcgtgccagccaaggtatcagcagctattt agcttggtaccagcagaagcccggcaaggcccccaagctgctgatctac gccgccagcactttacagagcggagtgcctagcagattcagcggcagcg gctccggcaccgagttcactttaaccatcagctctttacagcccgagga cttcgccacctactactgccagcagctgaacagctacccccttcaccttc ggccccggcaccaaggtggacatcaagcgtacggtggctgcaccatctg tcttcatcttcccgccatctgatgagcagttgaaatctggaactgcctc tgttgtgtgcctgctgaataacttctatcccagagaggccaaagtacag tggaaggtggataacgccctccaatcgggtaactcccaggagagtgtca cagagcaggacagcaaggacagcacctacagcctcagcagcaccctgac gctgagcaaagcagactacgagaaacacaaagtctacgcctgcgaagtc acccatcagggcctgagctcgcccgtcacaaagagcttcaacaggggag agtgt In some embodiments, the anti-BCMA antibody comprises a nucleic acid sequence that encodes an antibody comprising no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to SEQ ID NOs: 5, 10 and 13.

In some embodiments, the light chain of the anti-BCMA antibody or antigen binding fragment thereof comprises: three LCDRs, wherein,
LCDR1 comprises RASQGIX$_1$X$_2$YLA (SEQ ID NO: 79), LCDR2 comprises AASTLQS (SEQ ID NO: 7), and/or LCDR3 comprises QQLX$_3$SYPX$_4$T (SEQ ID NO: 80); wherein, X$_1$ is selected from S or N;
X$_2$ is selected from S or N;
X$_3$ is a charged amino acid selected from N or K; and/or
X$_4$ is a hydrophobic amino acid selected from F or W.

As will be understood by those of skill in the art, any such light chain CDR sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

In some embodiments, an anti-BCMA antibody described herein includes a light chain that includes any light chain constant domain sequence, e.g., a constant sequence of a light chain known to those of skill in the art. As those of skill in the art will be aware, a light chain constant domain may be a kappa light chain constant domain or a lambda light chain constant domain. In certain embodiments, the constant domain of a light chain as disclosed herein is a kappa light chain constant domain. In various embodiments, an anti-BCMA antibody described herein includes a light chain constant domain.

Exemplary Antibodies

Engineered antibodies can include various heavy chains and light chains described herein. In some embodiments, an anti-BCMA antibody can include two heavy chains and light chains. In various embodiments, the present disclosure encompasses an antibody including at least one heavy chain and/or light chain as disclosed herein, at least one heavy chain and/or light chain framework domain as disclosed herein, at least one heavy chain and/or light chain CDR domain as disclosed herein, and/or any heavy chain and/or light chain constant domain as disclosed herein.

In some embodiments, the engineered antibodies comprise an immunoglobulin VH amino acid sequence identical to SEQ ID NO: 1 and an immunoglobulin VL amino acid sequence identical to SEQ ID NO: 13. In some embodiments, the BCMA antibody or fragment thereof comprises an immunoglobulin VL region comprising an amino acid sequence that is at least 90% identical to SEQ ID NO: 13; and an immunoglobulin VH region comprising an amino acid sequence that is at least 90% identical to SEQ ID NO: 1. In some embodiments, the anti-BCMA antibody comprises a VH and/or a VL amino acid sequence having at least 70%, 75%, 80%, 85%, 90%, 91%, 92%, 93%, 94%, 95%, 96%, 97%, 98%, or 99% sequence identity to SEQ ID NO: 1 and/or SEQ ID NO: 13, while also including one or more of the vH CDR1, vHCDR2, vHCDR3, vLCDR1, vLCDR2 and/or vLCDR3 sequences described herein.

In some embodiments, the anti-BCMA antibodies or fragments thereof described herein comprise a common heavy chain variable region. In some embodiments, the anti-BCMA antibody comprises vHCDR and vLCDR sequences:

```
vHCDR1:
                                              (SEQ ID NO: 2)
SYAIH vHCDR2:
                                              (SEQ ID NO: 3)
VTWHDGSNKYYAESVMG vHCDR3:
                                              (SEQ ID NO: 4)
AKFGEPQYFQH vLCDR1:
                                              (SEQ ID NO: 11)
RASQGISSYLA vLCDR2:
                                              (SEQ ID NO: 7)
AASTLQS

VLCDR3:
                                              (SEQ ID NO: 14)
QQLNSYPWT
```

In certain embodiments, the CDRs are identified according to the Kabat numbering system.

In some embodiments, the engineered antibodies comprise an immunoglobulin VH amino acid sequence identical to SEQ ID NO: 1 and an immunoglobulin VL amino acid sequence identical to SEQ ID NO: 5. In some embodiments, the BCMA antibody or fragment thereof comprises an immunoglobulin VL region comprising an amino acid sequence that is at least 90% identical to SEQ ID NO: 5; and an immunoglobulin VH region comprising an amino acid sequence that is at least 90% identical to SEQ ID NO: 1. In some embodiments, the anti-BCMA antibody comprises a VH and/or a VL amino acid sequence having at least 70%, 75%, 80%, 85%, 90%, 91%, 92%, 93%, 94%, 95%, 96%, 97%, 98%, or 99% sequence identity to SEQ ID NO: 5 and/or SEQ ID NO: 1, while also including one or more of the vH CDR1, vHCDR2, vHCDR3, vLCDR1, vLCDR2 and/or vLCDR3 sequences described herein.

In some embodiments, the anti-BCMA antibodies or fragments thereof described herein comprise a common heavy chain variable region. In some embodiments, the anti-BCMA antibody comprises vHCDR and vLCDR sequences:

```
vHCDR1:
                                              (SEQ ID NO: 2)
SYAIH vHCDR2:
                                              (SEQ ID NO: 3)
VTWHDGSNKYYAESVMG vHCDR3:
                                              (SEQ ID NO: 4)
AKFGEPQYFQH vLCDR1:
                                              (SEQ ID NO: 6)
RASQGINNYLA vLCDR2:
                                              (SEQ ID NO: 7)
AASTLQS

VLCDR3:
                                              (SEQ ID NO: 8)
QQLKSYPFT
```

In certain embodiments, the CDRs are identified according to the Kabat numbering system.

In some embodiments, the engineered antibodies comprise an immunoglobulin VH amino acid sequence identical to SEQ ID NO: 9 and an immunoglobulin VL amino acid sequence identical to SEQ ID NO: 10. In some embodiments, the BCMA antibody or fragment thereof comprises an immunoglobulin VL region comprising an amino acid sequence that is at least 90% identical to SEQ ID NO: 10; and an immunoglobulin VH region comprising an amino acid sequence that is at least 90% identical to SEQ ID NO: 9. In some embodiments, the anti-BCMA antibody comprises a VH and/or a VL amino acid sequence having at least 70%, 75%, 80%, 85%, 90%, 91%, 92%, 93%, 94%, 95%, 96%, 97%, 98%, or 99% sequence identity to SEQ ID NO: 9 and/or SEQ ID NO: 10, while also including one or more of the vH CDR1, vHCDR2, vHCDR3, vLCDR1, vLCDR2 and/or vLCDR3 sequences described herein.

In some embodiments, the anti-BCMA antibodies or fragments thereof described herein comprise a common heavy chain variable region. In some embodiments, the anti-BCMA antibody comprises vHCDR and vLCDR sequences:

```
vHCDR1:
                                              (SEQ ID NO: 2)
SYAIH vHCDR2:
                                              (SEQ ID NO: 3)
VTWHDGSNKYYAESVMG vHCDR3:
                                              (SEQ ID NO: 4)
AKFGEPQYFQH vLCDR1:
                                              (SEQ ID NO: 11)
RASQGISSYLA vLCDR2:
                                              (SEQ ID NO: 7)
AASTLQS vLCDR3:
                                              (SEQ ID NO: 12)
QQLNSYPFT
```

In certain embodiments, the CDRs are identified according to the Kabat numbering system.

Exemplary Single Chain Variable Fragments

In some embodiments, the disclosure provides a single-chain variable fragment. In some embodiments, the scFv is a human scFv. A "single-chain variable fragment" or "scFv" refers to a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80 (6): 1910-1917 (2008) and WO 2014/087010, the contents of which are hereby incorporated by reference in their entireties. In certain embodiments, the linker is a G4S linker.

Alternatively or additionally, the scFv may be derived from Fab's (instead of from an antibody, e.g., obtained from Fab libraries). In certain embodiments, the anti-BCMA antibody or fragment thereof is a Fab. In certain embodiments, the Fab is cross-linked. In certain embodiments, the anti-BCMA antibody or fragment thereof is a F(ab)$_2$. Any of the foregoing molecules may be comprised in a fusion protein with a heterologous sequence to form an anti-BCMA antigen antibody or an antigen-binding fragment thereof.

In certain embodiments, the anti-BCMA antibody or fragment thereof binds to BCMA (e.g., human BCMA) with a dissociation constant ($K_d$) of at least about $1\times10^{-12}$ M, at least about $1\times10^{-7}$ M, at least about $1\times10^{-8}$ M, at least about $1\times10^{-9}$ M, or at least about $1\times10^{-10}$ M. In certain embodiments, the anti-BCMA antibody or fragment thereof binds to BCMA (e.g., human BCMA) with a dissociation constant ($K_D$) of at least about $2\times10^{-8}$ M. In certain embodiments, the anti-BCMA antibody or fragment thereof binds to BCMA (e.g., human BCMA) with a dissociation constant ($K_D$) of between about $2\times10^{-8}$ M and about $8\times10^{-9}$ M.

In some embodiments, the anti-BCMA antibody or fragment thereof binds to BCMA (e.g., human BCMA) with a dissociation constant ($K_D$) between about 1 nM and 50 nM, about 5 nM and 30 nM, about 5 nM and 25 nM, or about 8 nM and 20 nM. In some embodiments, the anti-BCMA antibody or fragment thereof binds to BCMA (e.g., human BCMA) with a dissociation constant ($K_D$) of at least about 50 nM, at least about 40 nM, at least about 35 nM, at least about 30 nM, at least about 25 nM, at least about 20 nM, at least about 19 nM, at least about 18 nM, at least about 17 nM, at least about 16 nM, at least about 15 nM, at least about 14 nM, at least about 13 nM, at least about 12 nM, at least about 11 nM, at least about 10 nM, at least about 9 nM, at least about 8 nM, at least about 7 nM, at least about 6 nM, at least about 5 nM.

In some embodiments, the anti-BCMA scFv comprises a variable heavy chain comprising SEQ ID Nos: 1-4. In some embodiments, the anti-BCMA scFv comprises a variable heavy chain comprising one or more CDR sequences provided in Table 1. In some embodiments, the anti-BCMA scFv comprises a variable light chain comprising one or more light chain sequences provided in Table 2.

In some embodiments, the anti-BCMA scFv comprises a linker comprises or consists of the amino acid sequence set forth in SEQ ID NO: 15, which is provided below: GGGGSGGGGSGGGGS (SEQ ID NO: 15). In some embodiments, the anti-BCMA scFv comprises a linker comprises or consists of the nucleic acid sequence set forth in SEQ ID NO: 81, which is provided below:

(SEQ ID NO: 81)
ggaggggcggtagcggaggggaggatctgggggtggggctcc

In some embodiments, the linker comprises or consists of the amino acid sequence set forth below:

(SEQ ID NO: 16)
GGGGSGGGSGGGSGGGGS

In some embodiments, the anti-BCMA scFv comprises a linker comprises or consists of the nucleic acid sequence set forth in SEQ ID NO: 82, which is provided below:

(SEQ ID NO: 82)
gggggggggggagcggaggggggggagtggtgggggtcaggagggg
gaggaagt

In some embodiments, the linker comprises or consists of the amino acid sequence set below:

(SEQ ID NO: 17)
GGGGSGGGGSGGGGSGGGSGGGGS

In some embodiments, the anti-BCMA scFv comprises a linker comprises or consists of the nucleic acid sequence set forth in SEQ ID NO: 83, which is provided below:

(SEQ ID NO: 83)
gggggaggggatcaggaggcggtgggagcggggaggtggatccggtgg
agggtcaggaggtggagggtcc.

In some embodiments, the linker comprises or consists of the amino acid sequence set below:

(SEQ ID NO: 18)
GGGGSGGGSGGGGSGGGGSGGGSGGGGS

In some embodiments, the anti-BCMA scFv comprises a linker comprises or consists of the nucleic acid sequence set forth in SEQ ID NO: 84 which is provided below:

(SEQ ID NO: 84)
ggtggtggcggcagcggcggcggcggtagcggtggcggcggttctggagg
aggaggcagcggtggaggaagcggaggtggaggctcc.

In some embodiments, the anti-BCMA antibody or fragment thereof comprises a conservative sequence modification (e.g., anti-BCMA antibody or fragment thereof described herein). In some embodiments, the conservative sequence modification is an amino acid modification that does not significantly affect or alter the binding characteristics of the presently disclosed anti-BCMA antibody or fragment thereof (e.g., the antibody or fragment thereof) comprising the amino acid sequence. Conservative modifications can include amino acid substitutions, additions and deletions. Modifications can be introduced into the anti-BCMA antibodies or fragments thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, and neutrally charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function. In certain embodiments, no more than one, no more than two, no more than three, no more than four, no more than five residues within a specified sequence or a CDR region are altered.

In some embodiments, the anti-BCMA scFv comprises an amino acid sequence:

(SEQ ID NO: 85)
EVQLVESGGDVVQPGRSLRLSCAASGFTFSSYAIHWVRQAPGKGLEWVAV

TWHDGSNKYYAESVMGRFTISRDNSKNTLYLHMNSLRAEDTGVYYCARAK

FGEPQYFQHWGQGTTVTVSSGGGGSGGGGSGGGGSDIVMTQSPSFLSASV

GDRVTITCRASQGISSYLAWYQQKPGKAPKLLIYAASTLQSGVPSRFSGS

GSGTEFTLTISSLQPEDFATYYCQQLNSYPFTFGPGTKVDIK

In some embodiments, the anti-BCMA scFv comprises an amino acid sequence:

(SEQ ID NO: 86)
QITLRESGGDVVQPGRSLRLSCAASGFTFSSYAIHWVRQAPGKGLEWVAV

TWHDGSNKYYAESVMGRFTISRDNSKNTLYLHMNSLRAEDTGVYYCARAK

FGEPQYFQHWGQGTLVTVSSGGGGSGGGGSGGGGSDIVMTQSPSFLSASV

GDRVTITCRASQGINNYLAWYQQKPGIAPKLLIYAASTLQSGVPSRFGGS

GSGTEFTLTISSLQPEDFATYYCQQLKSYPFTFGPGTKVEIK

In some embodiments, the anti-BCMA scFv comprises an amino acid sequence:

(SEQ ID NO: 87)
QITLRESGGDVVQPGRSLRLSCAASGFTFSSYAIHWVRQAPGKGLEWVAV

TWHDGSNKYYAESVMGRFTISRDNSKNTLYLHMNSLRAEDTGVYYCARAK

FGEPQYFQHWGQGTLVTVSSGGGGSGGGGSGGGGSDIVMTQSPSFLSASV

GDRVTITCRASQGISSYLAWYQQKPGKAPKLLIYAASTLQSGVPSRFSGS

GSGTEFTLTISSLQPEDFATYYCQQLNSYPWTFGQGTKVDIK

In some embodiments, the anti-BCMA scFv comprises an amino acid sequence having at least 70%, 75%, 80%, 85%, 90%, 91%, 92%, 93%, 94%, 95%, 96%, 97%, 98%, or 99% sequence identity to any of SEQ ID NOs: 51-53. In some embodiments, the anti-BCMA scFv comprises an amino acid sequence having at least 70%, 75%, 80%, 85%, 90%, 91%, 92%, 93%, 94%, 95%, 96%, 97%, 98%, or 99% sequence identity to any of SEQ ID NOs: 51-53, while comprising the respective variable regions. In some embodiments, the anti-BCMA scFv comprises an amino acid sequence having at least 70%, 75%, 80%, 85%, 90%, 91%, 92%, 93%, 94%, 95%, 96%, 97%, 98%, or 99% sequence identity to any of SEQ ID NOs: 51-53, while comprising the respective CDR regions.

Nucleotide Sequences

The present disclosure includes nucleotide sequences encoding one or more heavy chains, heavy chain variable domains, heavy chain framework regions, heavy chain CDRs, heavy chain constant domains, light chains, light chain variable domains, light chain framework regions, light chain CDRs, light chain constant domains, or other immunoglobulin-like sequences, or antibodies disclosed herein. In some embodiments, the nucleotide sequences are codon-optimized for mammalian expression. In various embodiments, such nucleotide sequences may be present in a vector. In various embodiments such nucleotides may be present in the genome of a cell, e.g., a cell of a subject in need of treatment or a cell for production of an antibody, e.g. a mammalian cell for production of a an antibody.

Engineered Antibodies and Fusion Proteins

In some embodiments, the disclosure provides fusion proteins comprising (i) one or more antigen-binding regions described herein (e.g., antigen-binding region of immunoglobulin, heavy chain antibody, light chain antibody, LRR-based antibody, or other protein scaffold with antibody-like properties, as well as other antigen binding moiety known in the art, including, e.g., a Fab, Fab', Fab'2, $Fab_2$, $Fab_3$, $F(ab')_2$, Fd, Fv, Feb, scFv, SMIP, antibody, diabody, triabody, tetrabody, minibody, maxibody, tandab, DVD, BiTe, TandAb, or the like), e.g., one or more variable domains described herein, or portion thereof (e.g., one or more CDRs described herein), and (ii) one or more additional polypeptides. For example, albumin is an abundant serum protein that is protected from degradation by pH-dependent recycling mediated by interaction with FcRn. In some embodiments, one or more variable domains or engineered antibodies as described herein, or portion thereof (e.g., one or more CDRs described herein) is fused to albumin, a portion thereof (such as a portion of albumin that binds to an FcRn), and/or an engineered variant of albumin that binds to FcRn with improved affinity. In other instances, one or more variable domains or engineered antibodies as described herein, or portion thereof (e.g., one or more CDRs described herein) is fused to a polypeptide that binds to albumin to form a fusion protein-albumin complex, which can in turn bind to an FcRn. In some embodiments, the polypeptide that binds to albumin is a single chain variable fragment (scFv). The albumin or portion thereof can include a mutation of one or more amino acids that can modify its binding to an FcRn. Such mutations are known in the art (see, e.g., Andersen et al., Nature Communications 3:610 doi: 10.1038/nocmms1607 (2012)). In other instances, one or more variable domains or engineered antibodies described herein, or portion thereof (e.g., one or more CDRs described herein) is fused to transferrin. Transferrin is recycled by binding to a transferrin receptor (see, e.g., Widera et al., *Adv. Drug Deliv. Rev.* 55:1439-66 (2003)).

Chimeric Antigenic Receptor (CAR)

In some examples, the BCMA antibodies can also be used in combination with antigen-specific, such as tumor antigen-specific CARs (also known as chimeric antigen receptors, artificial T cell receptors) or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signalling functions (Cartellieri et al., *Biomed Biotechnol* 2010:956304, 2010). In many instances, the binding moiety is an antigen binding fragment of a monoclonal antibody, such as a scFv, or is a single-domain antibody. Several different endodomains have been used to generate CARs. For example, the endodomain can consist of a signalling chain having an ITAM, such as CD3ζ or FcRIγ. In some instances, the endodomain further includes the intracellular portion of at least one additional co-stimulatory domain, such as CD28 and/or CD137.

BCMA antibodies and fragments thereof according to the present disclosure are engineered to include one or more binding moieties that specifically bind one or more targets of interest. An extracellular antigen binding region, such as a scFv, or Fab, can be a part of a CAR that determines antigen specificity. The extracellular antigen binding region can bind to any complementary target, such as BCMA. In certain aspects of any embodiment disclosed herein, the extracellular antigen binding region, such as scFv, can comprise a light chain CDR specific for an antigen. The light chain CDR can be a complementarity determining region of an antigen binding unit, such as scFv light chain of a CAR. BCMA antibodies and fragments thereof encompass nucleic acids (e.g., RNA and DNA), proteins (e.g., antibodies), and combination thereof.

CTLs expressing CARs can be used to target a specific cell type, such as a tumor cell. Thus, a tumor-antigen specific monoclonal antibody can be used to engineer CTLs that express a CAR containing an antigen-binding fragment of an antigen-specific antibody, thereby targeting the engineered CTLs to tumor antigen-expressing tumor cells. Engineered T cells have previously been used for adoptive therapy for some types of cancer (see, for example, Park et al., *Mol Ther* 15 (4): 825-833, 2007). The use of T cells expressing CARs is more universal than standard CTL-based immunotherapy because CTLs expressing CARs are HLA unrestricted and can therefore be used for any patient having a tumor that expresses the target antigen.

Antibody or Fragment Thereof as Binding Moieties

In some embodiments, an antibody or fragment thereof described herein is an anti-BCMA antibody. In some instances, one or more binding moieties described herein are or include antibodies, antigen-binding fragments thereof, and/or Fc regions (or Fc fragments) thereof. The basic structure of an IgG antibody consists of two identical light polypeptide chains and two identical heavy polypeptide chains linked together by disulfide bonds. The first domain located at the amino terminus of each chain is variable in amino acid sequence, providing antibody binding specificities found in each individual antibody. These are known as variable heavy (VH) and variable light (VL) regions. The other domains of each chain are relatively invariant in amino acid sequence and are known as constant heavy (CH) and constant light (CL) regions. For an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to as "antibody mimetics"), and antigen-binding fragments of any of the above. In certain embodiments, antibodies described herein refer to polyclonal antibody populations.

The term "Fc fragment", as used herein, refers to one or more fragments of an Fc region that retains an Fc function and/or activity described herein, such as binding to an Fc receptor. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) *Nature* 341:544-546), and an isolated complementarity determining region (CDR). These antibody fragments can be obtained using conventional techniques known to those with skill in the art, and fragments can be screened for utility in the same manner as are intact antibodies.

In some aspects the present invention provides antibodies or fragments thereof that bind to human BCMA comprising human heavy and/or light constant regions, wherein the human heavy constant region comprises an isotypic variant comprising the Fc region of human IgG1, human IgG2, human IgG3, or human IgG4.

In a further aspect the present invention provides a humanized antibody or fragment thereof that binds to human BCMA, wherein the antibody comprises a variant human IgG Fc region which comprises amino acid substitution S324N replacing serine at amino acid position 324 of the parent antibody with asparagine, whereas the antibody comprising the variant human IgG Fc region exhibits improved complement dependent cytotoxicity (CDC) compared to the parent antibody.

Antibodies or fragments can be produced by any method known in the art for synthesizing antibodies (see, e.g., Harlow et al., *Antibodies: A Laboratory Manual*, (Cold Spring Harbor Laboratory Press, 2nd ed. 1988); Brinkman et al., 1995, *J. Immunol. Methods* 182:41-50; WO 92/22324; WO 98/46645). Chimeric antibodies can be produced using methods described in, e.g., Morrison, 1985, *Science* 229: 1202, and humanized antibodies by methods described in, e.g., U.S. Pat. No. 6,180,370.

Additional compositions and methods described herein are bispecific antibodies and multivalent antibodies, as described in, e.g., Segal et al., *J. Immunol. Methods* 248:1-6 (2001); and Tutt et al., J. Immunol. 147:60 (1991).

Engineered Antigen Binding Regions

In some embodiments, a binding moiety is or includes an antibody (e.g., an IgG antibody, e.g., an IgG1, IgG2, or IgG3 antibody), or an antigen binding fragment, engineered to bind to one or more target (i.e., antigen) i.e., with differential affinities. For example, an antibody can be engineered by modifying (e.g., by adding, deleting, or substituting) an amino acid within one or more antibody CDRs and/or at a position involved in antibody CDR structure. Exemplary, non-limiting sites of an antibody that can be modified include the following (amino acid positions are indicated based on the Kabat numbering (Kabat et al., (1991) Sequences of Proteins of Immunological Interest, NIH)).

In some embodiments, one or more of these disclosed amino acids can be substituted with histidine, arginine, lysine, aspartic acid, glutamic acid, serine, threonine, asparagine, or glutamine. Without wishing to be bound by theory, it is believed that substituting an amino acid at one or more of these positions with a histidine can result in an antibody having pH-dependent antigen-binding properties. In some embodiments, a non-histidine residue is substituted with a histidine residue. In some embodiments, a histidine residue is substituted with a non-histidine residue. Additional engineered antigen binding regions include those described in, e.g., U.S. Publ. No. 20110229489.

Engineered Constant Regions

In some instances, a binding moiety is or includes an antibody constant region, Fc region or Fc fragment that binds one or more Fc receptors (e.g., FcγRI, FcγRIIA, FcγRIIB, FcγRIIIA, FcγRIIIB, FcγRIV, or FcRn receptor).

In some instances, a binding moiety can be or include a constant region, Fc region or Fc fragment of an IgG antibody engineered to include an amino acid addition, deletion, or substitution, of one or more of amino acid residues described herein (e.g., 251-256, 285-290, 308-314, 385-389, and 428-436 (Kabat numbering (Kabat et al., (1991) Sequences of Proteins of Immunological Interest, NIH))).

Generating and Producing BCMA Antibodies and Fragments Thereof

In some embodiments, a BCMA antibody described herein is generated by immunizing a humanized mouse, with human BCMA. In some embodiments, an antibody or fragment thereof described herein is further engineered to include one or more binding moieties. For example, a sequence of a reference polypeptide (e.g., a therapeutic antibody or therapeutic fusion protein) can be obtained, and one or more amino acid residues can be added, deleted, or substituted. In some embodiments, one or more amino acid residues are substituted with glycine, alanine, serine, cysteine, phenylalanine, tryptophan, tyrosine, proline, histidine, methionine, leucine, isoleucine, arginine, valine, lysine, aspartic acid, glutamic acid, threonine, asparagine, or glutamine. In some embodiments, antibodies comprising one or more amino acids are substitutions enhance the binding of the antibody to BCMA.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756, 2001; Lonberg, N. and D. Huszar *Int. Rev. Immunol* 13:65, 1995; and Pollock, et al., *J Immunol Methods* 231:147, 1999. Methods for making derivatives of antibodies, e.g., humanized, single chain, etc. are known in the art.

Measuring Interactions of Binding Moieties and Targets

The binding properties of an antibody or fragment thereof described herein (e.g., an anti-BCMA antibody described herein) to a target (e.g., BCMA and/or FcRn) can be measured by methods known in the art, e.g., one of the following methods: BIACORE analysis, Enzyme Linked Immunosorbent Assay (ELISA), x-ray crystallography, sequence analysis and scanning mutagenesis. The binding interaction of an antibody and BCMA and/or FcRn can be analyzed using surface Plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden). Additionally, a KinExA® (Kinetic Exclusion Assay) assay, available from Sapidyne Instruments (Boise, Id.) can also be used.

Information from SPR can be used to provide an accurate and quantitative measure of the equilibrium dissociation constant ($K_D$), and kinetic parameters, including $K_{on}$ and $K_{off}$, for the binding of a binding moiety to a target (e.g., an anti-BCMA antibody to BCMA and/or FcRn). Such data can be used to compare different molecules. Information from SPR can also be used to develop structure-activity relationships (SAR). For example, the kinetic and equilibrium binding parameters of particular binding moieties to targets at various pH levels can be evaluated. Variant amino acids at given positions can be identified that correlate with particular binding parameters, e.g., high affinity, low affinity, and slow $K_{off}$, at particular pH levels.

II. CAR Embodiments

In addition, the present disclosure concerns methods and compositions in which BCMA CAR constructs are better suited for use in NK cells because they have one or more components that are more relevant to NK cells, as opposed to biology that would be suited to other immune cells, including T cells.

In some embodiments, the present invention is directed to a chimeric antigen receptor (CAR) fusion protein comprising from N-terminus to C-terminus: (i) a single-chain variable fragment (scFv) against BCMA (i.e., "BCMA Binder"), (ii) hinge region; (iii) a transmembrane domain, and (iv) one or more intracellular signalling domains, such as at least one costimulatory domain and an activating domain.

In particular embodiments, the disclosure concerns the reprogramming of NK cells (for example, cord blood (CB)-derived NK cells) to target cancer cells expressing BCMA. The disclosure provides a number of novel CAR constructs incorporating different BCMA scFvs fused to a hinge region, particularly a CD28 or IgG1 hinge region, a transmembrane domain, and a signalling domain comprising cytoplasmic portions of CD247 (also known as CD3ζ) and CD28. In alternative embodiments, other costimulatory domain(s) besides CD28 are utilized.

BCMA Binders

A suitable BCMA Binder according to the present invention may be a scFv that specifically binds to BCMA. Typically, scFv can be in a form of VH-linker-VL or VL-linker-VH.

A particular linker that links the VH and VL chains may be utilized. One example of a linker amino acid sequence is as follows: GGGGSGGGGSGGGGS (SEQ ID NO: 15) or, GGGGSGGGGSGGGGSGGGGS (SEQ ID NO: 16) or, GGGGSGGGGSGGGGSGGGGSGGGGS (SEQ ID NO: 17) or, GGGGSGGGGSGGGGSGGGGSGGGGS (SEQ ID NO: 18) or, GGTGGTGGTGGTTCTGGTGGTGGTGGTTCTGGCG-
GCGGCGGCTCCGGTGGTGGTGGA TCC (SEQ ID NO: 24). In some embodiments, the linker comprises an amino acid sequence at least 75%, at least 85%, at least 85%, at least 90%, at least 95%, at least 96%, at least 97%, at least 98%, at least 99%, or 100% identical to SEQ ID NO: 15-18 and 24.

In some embodiments, the linker comprises an amino acid sequence of GGGGSGGGGSGGGSGGGGS (SEQ ID NO: 16).

In some embodiments, the BCMA Binder region of BCMA-CAR comprises a variable heavy chain region (VH) and a variable light chain region (VL). In some embodiments, a BCMA Binder contains three heavy chain complementarity determining regions (HCDRs), i.e., HCDR1, HCDR2 and HCDR3, and three light chain complementarity determining regions (LCDRs), i.e., LCDR1, LCDR2 and LCDR3, in the VH and VL regions respectively.

In some embodiments, the HCDR1 comprises amino acid sequence of SYAIH (SEQ ID NO: 2), the HCDR2 comprises amino acid sequence of VTWHDGSNKYYAESVMG (SEQ ID NO: 3), and the HCDR3 comprises amino acid sequence of AKFGEPQYFQH (SEQ ID NO: 4).

In some embodiments, the LCDR1 comprises amino acid sequence of RASQGINNYLA (SEQ ID NO: 6), the LCDR2 comprises amino acid sequence of AASTLQS (SEQ ID NO: 7), and the LCDR3 comprises amino acid sequence of QQLKSYPFT (SEQ ID NO: 8).

In some embodiments, the LCDR1 comprises amino acid sequence of RASQGISSYLA (SEQ ID NO: 11), the LCDR2 comprises amino acid sequence of AASTLQS (SEQ ID NO: 7), and the LCDR3 comprises amino acid sequence of QQLNSYPFT (SEQ ID NO: 12).

In some embodiments, the LCDR1 comprises amino acid sequence of RASQGISSYLA (SEQ ID NO: 11), the LCDR2 comprises amino acid sequence of AASTLQS (SEQ ID NO: 7), and the LCDR3 comprises amino acid sequence of QQLNSYPWT (SEQ ID NO: 14).

In some embodiments, a heavy chain variable region (VH) of the BCMA Binder comprises amino acid sequence:

(SEQ ID NO: 1)
QITLRESGGDVVQPGRSLRLSCAASGFTFSSYAIHWVRQAPGKGLEWVAV

TWHDGSNKYYAESVMGRFTISRDNSKNTLYLHMNSLRAEDTGVYYCARAK

FGEPQYFQHWGQGTLVTVSS.

It is envisioned that any amino acid substitution at any position other than the CDR sequences can be changed to another amino acid, for example a conservative amino acid substitution (as defined herein). In some embodiments, the VH comprises a sequence that is 70% identical to SEQ ID NO: 1. In some embodiments, the VH comprises a sequence that is 75% identical to SEQ ID NO: 1. In some embodiments, the VH comprises a sequence that is 80% identical to SEQ ID NO: 1. In some embodiments, the VH comprises a sequence that is 85% identical to SEQ ID NO: 1. In some embodiments, the VH comprises a sequence that is 90% identical to SEQ ID NO: 1. In some embodiments, the VH comprises a sequence that is 95% identical to SEQ ID NO: 1. In some embodiments, the VH comprises a sequence that is 99% identical to SEQ ID NO: 1.

In some embodiments, the heavy chain variable region (VH) of the BCMA Binder comprises amino acid sequence:

(SEQ ID NO: 9)
EVQLVESGGDVVQPGRSLRLSCAASGFTFSSYAIHWVRQAPGKGLEWVAV

TWHDGSNKYYAESVMGRFTISRDNSKNTLYLHMNSLRAEDTGVYYCARAK

FGEPQYFQHWGQGTTVTVSS.

It is envisioned that any amino acid substitution at any position other than the CDR sequences can be changed to another amino acid, for example a conservative amino acid substitution (as defined herein). In some embodiments, the VH comprises a sequence that is 70% identical to SEQ ID NO: 9. In some embodiments, the VH comprises a sequence that is 75% identical to SEQ ID NO: 9. In some embodiments, the VH comprises a sequence that is 80% identical to SEQ ID NO: 9. In some embodiments, the VH comprises a sequence that is 85% identical to SEQ ID NO: 9. In some embodiments, the VH comprises a sequence that is 90% identical to SEQ ID NO: 9. In some embodiments, the VH comprises a sequence that is 95% identical to SEQ ID NO: 9. In some embodiments, the VH comprises a sequence that is 99% identical to SEQ ID NO: 9.

In some embodiments, the BCMA-Binder comprises a light chain variable region (VL). In some embodiments, the VL comprises amino acid sequence:

(SEQ ID NO: 5)
DIVMTQSPSFLSASVGDRVTITCRASQGINNYLAWYQQKPGIAPKLLIYA

ASTLQSGVPSRFGGSGSGTEFTLTISSLQPEDFATYYCQQLKSYPFTFGP

GTKVEIK.

It is envisioned that any amino acid substitution at any position other than the CDR sequences can be changed to another amino acid, for example a conservative amino acid substitution (as defined herein). In some embodiments, the VL comprises a sequence that is 70% identical to SEQ ID NO: 5. In some embodiments, the VL comprises a sequence that is 75% identical to SEQ ID NO: 5. In some embodiments, the VL comprises a sequence that is 80% identical to SEQ ID NO: 5. In some embodiments, the VL comprises a sequence that is 85% identical to SEQ ID NO: 5. In some embodiments, the VL comprises a sequence that is 90% identical to SEQ ID NO: 5. In some embodiments, the VL comprises a sequence that is 95% identical to SEQ ID NO: 5. In some embodiments, the VL comprises a sequence that is 99% identical to SEQ ID NO: 5.

In some embodiments, the BCMA-binding region of the CAR comprises a light chain variable region (VL). In some embodiments, the VL comprises amino acid sequence:

(SEQ ID NO: 10)
DIVMTQSPSFLSASVGDRVTITCRASQGISSYLAWYQQKPGKAPKLLIYA

ASTLQSGVPSRFSGSGSGTEFTLTISSLQPEDFATYYCQQLNSYPFTFGP

GTKVDIK.

It is envisioned that any amino acid substitution at any position other than the CDR sequences can be changed to another amino acid, for example a conservative amino acid substitution (as defined herein). In some embodiments, the VL comprises a sequence that is 70% identical to SEQ ID NO: 10. In some embodiments, the VL comprises a sequence that is 75% identical to SEQ ID NO: 10. In some embodiments, the VL comprises a sequence that is 80% identical to SEQ ID NO: 10. In some embodiments, the VL comprises a sequence that is 85% identical to SEQ ID NO:

10. In some embodiments, the VL comprises a sequence that is 90% identical to SEQ ID NO: 10. In some embodiments, the VL comprises a sequence that is 95% identical to SEQ ID NO: 10. In some embodiments, the VL comprises a sequence that is 99% identical to SEQ ID NO: 10.

In some embodiments, the BCMA-binding region of the CAR comprises a light chain variable region (VL). In some embodiments, the VL comprises amino acid sequence:

(SEQ ID NO: 13)
DIVMTQSPSFLSASVGDRVTITCRASQGISSYLAWYQQKPGKAPKLLIYA

ASTLQSGVPSRFSGSGSGTEFTLTISSLQPEDFATYYCQQLNSYPWTFGQ

GTKVDIK.

It is envisioned that any amino acid substitution at any position other than the CDR sequences can be changed to another amino acid, for example a conservative amino acid substitution (as defined herein). In some embodiments, the VL comprises a sequence that is 70% identical to SEQ ID NO: 13. In some embodiments, the VL comprises a sequence that is 75% identical to SEQ ID NO: 13. In some embodiments, the VL comprises a sequence that is 80% identical to SEQ ID NO: 13. In some embodiments, the VL comprises a sequence that is 85% identical to SEQ ID NO: 13. In some embodiments, the VL comprises a sequence that is 90% identical to SEQ ID NO: 13. In some embodiments, the VL comprises a sequence that is 95% identical to SEQ ID NO: 13. In some embodiments, the VL comprises a sequence that is 99% identical to SEQ ID NO: 13.

In some embodiments, the BCMA-binder in the chimeric antigen receptor comprises a VH of SEQ ID NO: 1 and a VL of SEQ ID NO: 5.

In some embodiments, the BCMA-binder in the chimeric antigen receptor comprises a VH at least 70% identical to SEQ ID NO: 1 and a VL at least 70% identical to SEQ ID NO: 5.

In some embodiments, the BCMA-binder in the chimeric antigen receptor comprises a VH at least 75% identical to SEQ ID NO: 1 and a VL at least 75% identical to SEQ ID NO: 5.

In some embodiments, the BCMA-binder in the chimeric antigen receptor comprises a VH at least 80% identical to SEQ ID NO: 1 and a VL at least 80% identical to SEQ ID NO: 5.

In some embodiments, the BCMA-binder in the chimeric antigen receptor comprises a VH at least 90% identical to SEQ ID NO: 1 and a VL at least 90% identical to SEQ ID NO: 5.

In some embodiments, the BCMA-binder in the chimeric antigen receptor comprises a VH at least 95% identical to SEQ ID NO: 1 and a VL at least 95% identical to SEQ ID NO: 5.

In some embodiments, the BCMA-binder in the chimeric antigen receptor comprises a VH at least 97% identical to SEQ ID NO: 1 and a VL at least 97% identical to SEQ ID NO: 5.

In some embodiments, the BCMA-binder in the chimeric antigen receptor comprises a VH at least 70% identical to SEQ ID NO: 9 and a VL at least 70% identical to SEQ ID NO: 10.

In some embodiments, the BCMA-binder in the chimeric antigen receptor comprises a VH at least 75% identical to SEQ ID NO: 9 and a VL at least 75% identical to SEQ ID NO: 10.

In some embodiments, the BCMA-binder in the chimeric antigen receptor comprises a VH at least 80% identical to SEQ ID NO: 9 and a VL at least 80% identical to SEQ ID NO: 10.

In some embodiments, the BCMA-binder in the chimeric antigen receptor comprises a VH at least 90% identical to SEQ ID NO: 9 and a VL at least 90% identical to SEQ ID NO: 10.

In some embodiments, the BCMA-binder in the chimeric antigen receptor comprises a VH at least 95% identical to SEQ ID NO: 9 and a VL at least 95% identical to SEQ ID NO: 10.

In some embodiments, the BCMA-binder in the chimeric antigen receptor comprises a VH at least 97% identical to SEQ ID NO: 9 and a VL at least 97% identical to SEQ ID NO: 10.

In some embodiments, the BCMA-binder in the chimeric antigen receptor comprises a VH of SEQ ID NO: 1 and a VL of SEQ ID NO: 13.

In some embodiments, the BCMA-binder in the chimeric antigen receptor comprises a VH at least 70% identical to SEQ ID NO: 1 and a VL at least 70% identical to SEQ ID NO: 13.

In some embodiments, the BCMA-binder in the chimeric antigen receptor comprises a VH at least 75% identical to SEQ ID NO: 1 and a VL at least 75% identical to SEQ ID NO: 13.

In some embodiments, the BCMA-binder in the chimeric antigen receptor comprises a VH at least 80% identical to SEQ ID NO: 1 and a VL at least 80% identical to SEQ ID NO: 13.

In some embodiments, the BCMA-binder in the chimeric antigen receptor comprises a VH at least 90% identical to SEQ ID NO: 1 and a VL at least 90% identical to SEQ ID NO: 13.

In some embodiments, the BCMA-binder in the chimeric antigen receptor comprises a VH at least 95% identical to SEQ ID NO: 1 and a VL at least 95% identical to SEQ ID NO: 13.

In some embodiments, the BCMA-binder in the chimeric antigen receptor comprises a VH at least 97% identical to SEQ ID NO: 1 and a VL at least 97% identical to SEQ ID NO: 13.

In some embodiments, embodiment, specific embodiment, molecules that specifically bind to an antigen bind with a dissociation constant ($K_d$) of about $1\times10$ 7M. In some embodiments, the antigen binding molecule specifically binds an antigen with "high affinity" when the $K_d$ is about $1\times10^{-9}$ M to about $5\times10$ 9 M. In some embodiments, the antigen binding molecule specifically binds an antigen with "very high affinity" when the $K_d$ is $1\times10^{-10}$ M to about 5×10-10 M. In one embodiment, the antigen binding molecule has a $K_d$ of $10^{-9}$ M. In one embodiment, the off-rate is less than about $1\times10^{-5}$. In other embodiments, the antigen binding molecule binds human BCMA with a $K_d$ of between about $1\times10^{-7}$ M and about $1\times10^{-13}$ M. In yet another embodiment, the antigen binding molecule binds human BCMA with a $K_d$ of about $1\times10^{-10}$ M to about $5\times10^{-10}$ M.

In another specific embodiment, molecules that specifically bind to an antigen do not cross react with other proteins under similar binding conditions. In another specific embodiment, molecules that specifically bind to an antigen do not cross react with other non-BCMA proteins. In a specific embodiment, provided herein is an antibody or fragment thereof that binds to BCMA with higher affinity than to another unrelated antigen. In certain embodiments, provided herein is an antibody or fragment thereof that binds to BCMA (e.g., human BCMA) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-BCMA antibody or antigen-binding fragment thereof described herein to an unrelated, non-BCMA protein is less than 10%, 15%, or 20% of the binding of the antibody to BCMA protein as measured by, e.g., a radioimmunoassay.

In a specific embodiment, provided herein is an antibody or fragment thereof that binds to human BCMA with higher affinity than to another species of BCMA. In certain embodiments, provided herein is an antibody or fragment thereof that binds to human BCMA with a 5%, 10%, 15%, 20%, 25%, 30%, 35%, 40%, 45%, 50%, 55%, 60%, 65%, 70% or higher affinity than to another species of BCMA as measured by, e.g., a radioimmunoassay, surface plasmon resonance, or kinetic exclusion assay. In a specific embodiment, an antibody or fragment thereof described herein, which binds to human BCMA, will bind to another species of BCMA protein with less than 10%, 15%, or 20% of the binding of the antibody or fragment thereof to the human BCMA protein as measured by, e.g., a radioimmunoassay, surface plasmon resonance, or kinetic exclusion assay.

Hinge Region

In particular embodiments, the CAR polypeptide comprises an extracellular spacer domain (that may also be referred to as a hinge) that links the antigen binding domain and the transmembrane domain. The hinge domain is a spacer that provides separation of the scFv from the cell membrane and an intracellular signalling module that mediates NK cell activation or T-cell activation. Extracellular spacer domains may include, but are not limited to, a hinge from a human protein. For example, in one embodiment, the hinge can be a human Ig (immunoglobulin) hinge, e.g., an IgG4 hinge, or a CD8a hinge, artificial spacers made of polypeptides such as Gly3, or CH1, CH2, and/or CH3 domains of IgGs (such as human IgG1 or IgG4).

In specific cases, the extracellular spacer domain may comprise (i) a hinge, CH2 and CH3 regions of IgG4, (ii) a hinge region of IgG4, (iii) a hinge and CH2 of IgG4, (iv) a hinge region of CD8-alpha, (v) a hinge region of CD28, (vi) a hinge, CH2 and CH3 regions of IgG1, (vii) a hinge region of IgG1.

According to the present invention, a particularly useful hinge is derived from CD28. In certain embodiments, the CAR polypeptide comprises a particular CD28 hinge amino acid sequence or is encoded by a particular CD28 hinge nucleic acid sequence. Examples are as follows:

An exemplary suitable CD28 hinge contains the following amino acid sequence:

```
                                        (SEQ ID NO: 36)
RAAAIEVMYPPPYLDNEKSNGTIIHVKGKHLCPSPLFPGPSKPKDPK
```

An exemplary suitable CD28 hinge is encoded by the following nucleic acid sequence:

```
                                        (SEQ ID NO: 35)
cgggcggccgcaattgaagttatgtatcctcctccttacctagacaatga gaagagcaatggaaccattatccatgtgaaagggaaacacctttgtccaa gtcccctatttcccggaccttctaagcccaaagatcccaaa
```

An exemplary suitable IgG hinge contains the following amino acid sequence:

```
                                        (SEQ ID NO: 37)
RTVTVSSQDPAEPKSPDKTHTCPPCPAPELLGGPSVFLFPPKPKDTLMIS

RTPEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLPPS

RDELTKNQVSLTCLVKGFYPSDIAVEWESNGQPENNYKTTPPVLDSDGSF

FLYSKLTVDKSRWQQGNVFSCSVMHEALHNHYTQKSLSLSPGKKDPK
```

An exemplary suitable IgG hinge contains the following nucleic acid sequence:

```
                                        (SEQ ID NO: 38)
cgtacggtcactgtctcttcacaggatcccgccgagcccaaatctcctga caaaactcacacatgcccaccgtgcccagcacctgaactctgggggac cgtcagtcttcctcttccccccaaaacccaaggacaccctcatgatctcc cggacccctgaggtcacatgcgtggtggtggacgtgagccacgaagaccc tgaggtcaagttcaactggtacgtggacggcgtggaggtgcataatgcca agacaaagccgcgggaggagcagtacaacagcacgtaccgtgtggtcagc gtcctcaccgtcctgcaccaggactggctgaatggcaaggagtacaagtg caaggtctccaacaaagccctcccagcccccatcgagaaaaccatctcca aagccaaagggcagccccgagaaccacaggtgtacaccctgccccatcc cgggatgagctgaccaagaaccaggtcagcctgacctgcctggtcaaagg cttctatcccagcgacatcgccgtggagtgggagagcaatgggcaaccgg agaacaactacaagaccacgcctcccgtgctggactccgacggctccttc ttcctctacagcaagctcaccgtggacaagagcaggtggcagcagggaa cgtcttctcatgctccgtgatgcatgaggctctgcacaaccactacacgc agaagagcctctccctgtctccgggtaaaaaagatcccaaa
```

Transmembrane Domain

The transmembrane connects the intracellular signalling domain to the hinge region of a CAR. In some embodiments, the CAR comprises a transmembrane domain. In some embodiments, a suitable transmembrane domain according to the present invention is a transmembrane domain of CD28, 4-1BB/CD137, CD8 (e.g., CD8 alpha), CD4, CD19, CD3 epsilon, CD45, CD5, CD9, CD16, CD22, CD33, CD37, CD64, CD80, CD86, CD134, CD137, CTLA4, PD-1 or CD154. Exemplary transmembrane domains are disclosed in WO2020227446 incorporated herein in its entirety.

In some embodiments, the transmembrane is a CD28 transmembrane domain. In some embodiments, the transmembrane domain is a CD28 transmembrane domain comprising amino acid sequence of:

(SEQ ID NO: 26)
FWVLVVVGGVLACYSLLVTVAFIIFWV

In some embodiments, the transmembrane is encoded by nucleic acid sequence:

(SEQ ID NO: 27)
ttttgggtgctggtggtggttggtggagtcctggcttgctatagcttgct agtaacagtggcctttattattttctgggtg

Costimulatory Domain

The CAR may comprise one or more costimulatory domains. Costimulatory signals are required to achieve robust chimeric antigen receptor (CAR) comprising cell expansion, function, persistence and antitumor activity. In some embodiments, a costimulatory region according to the present invention is a signalling region of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1 (CD11a/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), Fc gamma receptor, MHC class I molecule, TNF receptor proteins, Immunoglobulin-like proteins, cytokine receptors, integrins, signalling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKD80 (KLRF1), NKD44, NKD30, NKD46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In some embodiments, the costimulatory domain comprises:

(SEQ ID NO: 28)
RSKRSRLLHSDYMNMTPRRPGPTRKHYQPYAPPRDFAAYRS

In some embodiments, the costimulatory domain is encoded by:

(SEQ ID NO: 29)
aggagtaagaggagcaggctcctgcacagtgactacatgaacatgactcc ccgccgccccgggcccaccccgcaagcattaccagccctatgccccaccac gcgacttcgcagcctatcgctca

Activation Domain

According to the invention, a CAR construct may also include an activation domain. In particular embodiments, the CAR polypeptide comprises an immune cell activation moiety. The activation moiety acts in conjunction with the costimulatory moiety to activate downstream signalling cascades that lead to NK cell activation, proliferation, acquisition of effector functions and secretion of inflammatory cytokines and chemokines. In some embodiments, the activation moiety is CD3ξ.

One example of a CD3 amino acid sequence is as follows:

(SEQ ID NO: 30)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

One example of a CD3ζ nucleic acid sequence is as follows:

(SEQ ID NO: 31)
cgcgtgaagttcagcaggagcgcagacgcccccgcgtaccagcagggcca gaaccagctctataacgagctcaatctaggacgaagagaggagtacgatg ttttggacaaaagacgtggccgggaccctgagatggggggaaagccgaga aggaagaaccctcaggaaggcctgtacaatgaactgcagaaagataagat ggcggaggcctacagtgagattgggatgaaaggcgagcgccggaggggca aggggcacgatggcctttaccagggtctcagtacagccaccaaggacacc tacgacgcccttcacatgcaggccctgccccctcgc

Signal Peptide

In particular embodiments, the CAR polypeptide comprises a signal peptide. The signal peptide is part of the ectodomain of the CAR polypeptide. In some embodiments, the ectodomain is the part of a CAR protein that is outside the cytoplasm and exposed to the extracellular space. The function of a signal peptide is to transfer the recognized protein signal to the cellular endoplasmic reticulum. In some embodiments, the signal peptide can be selected from a heavy chain signal peptide, IL-15 signal peptide, a CD8a signal peptide, a GMCSF-R signal peptide.

One example of a signal peptide amino acid sequence is as follows:

(SEQ ID NO: 51)
MEFGLSWLFLVAILKGVQC

One example of a signal peptide nucleic acid sequence is as follows:

(SEQ ID NO: 52)
atggaattcggattgtcatggttgttcctcgtcgcaattctcaagggcgt gcagtgc.

One example of a signal peptide amino acid sequence is as follows:

(SEQ ID NO: 32)
MRISKPHLRSISIQCYLCLLLNSHFLTEA

One example of a signal peptide nucleic acid sequence is as follows:

(SEQ ID NO: 33)
Atgcgcattagcaagccccacctgcggagcatcagcatccagtgctacct gtgcctgctgctgaacagccacttcctgaccgaggcc.

In some embodiments, the CAR comprises a cleavage site. One example of a cleavage site is:

(SEQ ID NO: 39)
GPQCTNYALLKLAGDVESNPGP.

In some embodiments, the cleavage site is encoded by:

(SEQ ID NO: 40)
ggaccgcagtgtactaattatgctctcttgaaattggctggagatgttga gagcaatcccgggccc.

Cytokines

In some embodiments, the expression of cytokines in CAR expressing cells improves their antitumor efficacy. In one embodiment, cytokine is expressed as part of the CAR. In another embodiment, the cytokine is expressed in a separate expression system. In some embodiments, cytokines can be selected from IL-15, IL-12, IL-2, IL-18, IL-21, or a combination thereof. In one embodiment, the cytokine is selected from growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-3, IL-4, IL-5, IL-6, IL-7, IL-8, IL-9, IL-10, IL-11, IL-15, a tumor necrosis factor such as TNFα or TNF-beta; and other polypeptide factors including LIF and kit ligand (KL).

In one embodiment, the cytokine is IL-15. In one embodiment, the cytokine IL-15 region comprises amino acid sequence as follows:

(SEQ ID NO: 23)
GIHVFILGCFSAGLPKTEANWVNVISDLKKIEDLIQSMHIDATLYTESDV

HPSCKVTAMKCFLLELQVISLESGDASIHDTVENLIILANNSLSSNGNVT

ESGCKECEELEEKNIKEFLQSFVHIVQMFINTS.

One example of a IL-15 nucleic acid sequence is as follows:

(SEQ ID NO: 34)
ggcatccacgtgttcatcctgggctgcttcagcgccggactgcccaagac cgaggccaactgggtgaacgtgatcagcgacctgaagaagatcgaggacc tgatccagagcatgcacatcgacgccaccctgtacaccgagagcgacgtg cacccagctgcaaggtgaccgccatgaagtgctttctgctggaactgca ggtgatcagcctggaaagcggcgacgccagcatccacgacaccgtggaga acctgatcatcctggccaacaacagcctgagcagcaacggcaacgtgacc gagagcggctgcaaagagtgcgaggaactggaagagaagaacatcaaaga gtttctgcagagcttcgtgcacatcgtgcagatgttcatcaacaccagc In some embodiments, the IL-15 polypeptide encompassed by the present disclosure may comprise SEQ ID NO: 23 or a sequence that is at least 70, 75, 80, 85, 90, 95, 96, 97, 98, 99, or more % identical to SEQ ID NO: 23.

Suicide Gene

In particular embodiments, a suicide gene is utilized in conjunction with cell therapy of any kind to control its use and allow for termination of the cell therapy at a desired event and/or time. The suicide gene is employed in transduced cells for the purpose of eliciting death for the transduced cells when needed. The antigen-targeting cells of the present disclosure that have been modified to harbor a vector encompassed by the disclosure may comprise one or more suicide genes. In some embodiments, the term "suicide gene" as used herein is defined as a gene which, upon administration of a prodrug or other agent, effects transition of a gene product to a compound which kills its host cell. In other embodiments, a suicide gene encodes a gene product that is, when desired, targeted by an agent (such as an antibody) that targets the suicide gene product. A "suicide gene product" describes a protein or polypeptide encoded by a suicide gene.

Examples of suicide gene/prodrug combinations which may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside. The E. coli purine nucleoside phosphorylase, a so-called suicide gene that converts the prodrug 6-methylpurine deoxyriboside to toxic purine 6-methylpurine, may be used. Other examples of suicide genes used with prodrug therapy are the E. coli cytosine deaminase gene and the HSV thymidine kinase gene.

Exemplary suicide genes also include CD20, CD52, EGFRv3, or inducible caspase 9. In one embodiment, a truncated version of EGFR variant III (EGFRv3) may be used as a suicide antigen that can be ablated by Cetuximab. Further suicide genes known in the art that may be used in the present disclosure include Purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-α,γ-lyase (MET), and Thymidine phosphorylase (TP).

In some embodiments, an inducible caspase 9 (iC9) is used as an exemplary suicide gene. An example iC9 is described in, for example, Yagyu S, et al. Mol Ther. 2015 September; 23 (9): 1475-85, incorporated by reference herein in its entirety. In some embodiments, the iCaspase9 comprises amino acid sequence:

(SEQ ID NO: 25)
MSTESMIRDVELAEEALPKKTGGPQGSRRCLFLSLFSFLIVAGATTLFC

LLHFGVIGPQREEFPRDLSLISPLAQAVRSSSRTPSDKPVAHVVANPQA

EGQLQWLNRRANALLANGVELRDNQLVVPSEGLYLIYSQVLFKGQGCPS

THVLLTHTISRIAVSYQTKVNLLSAIKSPCQRETPEGAEAKPWYEPIYL

GGVFQLEKGDRLSAEINRPDYLDFAESGQVYFGIIAL.

In some embodiments, the present disclosure concerns methods and compositions that provide for a cell therapy to be terminated using uncleavable mutants of the 26 kd TNFα. The TNFα mutants are uncleavable that leaves them membrane bound and nonsecretable. Cells expressing the uncleavable TNFα mutants can be targeted for selective deletion including, for example, using FDA-approved TNFα antibodies currently in the clinic, such as etanercept, infliximab, or adalilumab. The mutated TNFα polypeptide may be co expressed with one or more therapeutic transgenes, such as a gene encoding a CAR. In addition, the TNF-α mutant expressing cells have superior activity against the tumor target, mediated by the biological activity of the membrane-bound TNFα protein.

In specific embodiments, the suicide gene is a tumor necrosis factor (TNF) a mutant that is uncleavable by standard enzymes that cleave TNF in nature, such as TNFα-converting enzyme (also referred to as TACE). As such, the TNFα mutant is membrane-bound and nonsecretable, in particular embodiments. The TNFα mutant used in the disclosure is targetable by one or more agents that bind the mutant, including at least an antibody, such that following binding of the agent(s) to the TNFα mutant on the surface of the cell, the cell dies. Embodiments of the disclosure allow the TNFα mutant to be utilized as a marker for cells that express it.

Cells expressing the uncleavable TNFα mutants can be targeted for selective deletion including, for example, using FDA-approved TNFα antibodies currently in the clinic, such as etanercept, infliximab or adalilumab. The mutated TNFα polypeptide may be co expressed with one or more therapeutic transgenes in the cell, such as a gene encoding a CAR, including BCMA-targeting CARs. In addition, the TNF-alpha mutant expressing cells have superior activity against the tumor target, mediated by the biological activity of the membrane-bound TNFα protein.

Wild-type TNFα has a 26 kD transmembrane form and a 17 kD secretory component. In some embodiments, TNFα mutants described in Perez el al. (1990) may be utilized in this disclosure. In specific embodiments, a TNFα mutant comprises deletion of the respective amino acid at position −3, −2, −1, 1, 2, 3, 4, 5, 6, 7, 8, 9, 10, 11, 12, 13, or a combination thereof. Specific combinations include deletions at positions −3 through and including 13; −3 through and including 12; −3 through and including 11; −3 through and including 10; −3 through and including 9; −3 through and including 8; −3 through and including 7; −3 through and including 6; −3 through and including 5; −3 through and including 4; −3 through and including 3; −3 through and including 2; −3 through and including 1; −3 through and including −1; −3 through and including −2; −2 through and including 13; −2 through and including 12; −2 through and including 11; −2 through and including 10; −2 through and including 9; −2 through and including 8; −2 through and including 7; −2 through and including 6; −2 through and including 5; −2 through and including 4; −2 through and including 3; −2 through and including 2; −2 through and including 1; −2 through and including −1; −1 through and including 13; −1 through and including 12; −1 through and including 11; −1 through and including 10; −1 through and including 9; −1 through and including 8; −1 through and including 7; −1 through and including 6; −1 through and including 5; −1 through and including 4; −1 through and including 3; −1 through and including 2; −1 through and including 1; 1 through and including 13; 1 through and including 12; 1 through and including 11; 1 through and including 10; 1 through and including 9; 1 through and including 8; 1 through and including 7; 1 through and including 6; 1 through and including 5; 1 through and including 4; 1 through and including 3; 1 through and including 2; and so forth. In specific embodiments, examples of TNF-alpha mutants of the disclosure include at least the following with respect to the 17 kD TNF: (1) deletion of Val1 and deletion of Pro112; (2) deletion of Val13; (3) deletion of Val1 and deletion of Val13; (4) deletion of Val1 through and including Pro12 and deletion of Val13 (delete 13aa); (5) deletion of Ala-3 through to and including Val 13 (delete 16 aa).

The TNFα mutants may be generated by any suitable method, but in specific embodiments they are generated by site-directed mutagenesis. In some cases, the TNFα mutants may have mutations other than those that render the protein uncleavable. In specific cases, the TNFα mutants may have 1, 2, 3, or more mutations other than the deletions at Val, Pro12, and/or Val13 or the region there between. The mutations other than those that render the mutants nonsecretable may be one or more of an amino acid substitution, deletion, addition, inversion, and so forth. In cases wherein the additional mutation is an amino acid substitution, the substitution may or may not be to a conservative amino acid, for example. In some cases, 1, 2, 3, 4, 5, or more additional amino acids may be present on the N-terminal and/or C-terminal ends of the protein. In some cases, a TNFα mutant has (1) one or more mutations that render the mutant nonsecretable; (2) one or more mutations that prevents outside- in signalling for the mutant; and/or (3) one or more mutations that interfere with binding of the mutant to TNF Receptor 1 and/or TNF Receptor 2.

In particular embodiments, the TNFα mutant polypeptide comprises a deletion with respect to SEQ ID NO: 25 of the following: amino acid residue 1 and amino acid residue 12; amino acid residue 1 and amino acid residue 13; amino acid residues 1-12; amino acid residues 1-13; or amino acid residues-1 to 13.

Exemplary TNFα mutant polypeptide sequences, mutants and variants are disclosed in WO2020106619 and WO2021055349 which are incorporated herein by reference in their entirety.

Exemplary Full-Length BCMA-CAR Sequences

In some embodiments, the BCMA-CAR comprises an amino acid sequence comprising:

(SEQ ID NO: 19)
MEFGLSWLFLVAILKGVQCEVQLVESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTTVTVSSGGGGSGGG

GSGGGGSDIVMTQSPSFLSASVGDRVTITCRASQGISSYLAWYQQKPGK

APKLLIYAASTLQSGVPSRFSGSGSGTEFTLTISSLQPEDFATYYCQQL

NSYPFTFGPGTKVDIKRAAAIEVMYPPPYLDNEKSNGTIIHVKGKHLCP

SPLFPGPSKPKDPKFWVLVVVGGVLACYSLLVTVAFIIFWVRSKRSRLL

HSDYMNMTPRRPGPTRKHYQPYAPPRDFAAYRSRVKFSRSADAPAYQQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPR.

In some embodiments, the BCMA-CAR comprises an amino acid sequence at least 70% identical to SEQ ID NO: 19. In some embodiments, the BCMA-CAR comprises an amino acid sequence at least 75% identical to SEQ ID NO: 19. In some embodiments, the BCMA-CAR comprises an amino acid sequence at least 80% identical to SEQ ID NO: 19. In some embodiments, the BCMA-CAR comprises an amino acid sequence at least 85% identical to SEQ ID NO: 19. In some embodiments, the BCMA-CAR comprises an amino acid sequence at least 90% identical to SEQ ID NO: 19. In some embodiments, the BCMA-CAR comprises an amino acid sequence at least 95% identical to SEQ ID NO: 19. In some embodiments, the BCMA-CAR comprises an amino acid sequence at least 97% identical to SEQ ID NO: 19. In some embodiments, the BCMA-CAR comprises an amino acid sequence at least 99% identical to SEQ ID NO: 19.

In some embodiments, the BCMA-CAR comprises an nucleic acid sequence comprising:

(SEQ ID NO: 42)
atggaatttggactgtcatggcttttcttgtcgccatcctgaaagggg tacagtgtgaagtgcaactggtcgaatctgggggagacgttgtcc agcccgggaggtctttgcggttgtcatgcgcagcttcaggttttacttt ctcttcatacgccatccattgggttcggcaagcgcctggtaaggg actcgaatgggttgcagtgacctggcatgacggatcaaacaagtattat gcagaatcagtaatgggcaggtttaccatttcacgcgacaatag caaaaatacactttatttgcacatgaattcactcagagccgaagatacc ggcgtctattattgcgccagagcaaaatttggggagccacagta cttccaacattggggacaaggcactaccgtcaccgtgagttcaggcggg gggggatcaggcggaggaggttcaggcggcggcggcagt gacatagtgatgactcagagtccttcattttgagcgcaagtgttgggg ataggtcactataacgtgtagagcatctcaaggcatttcttcatat ttggcctggtatcaacagaaacctggaaaggccccaaagctccttattt acgctgcatcaaccctgcaatctggcgtcccaagccgattctct gggtctggaagcggcacagaatttaccctgactatatcatctctccaac ctgaagatttgccacctattattgtcagcaattgaattcatacccg ttcacattcggccctggaactaaagtcgacatcaagcgggcggccgcaa ttgaagttatgtatcctcctccttacctagacaatgagaagagc aatggaaccattatccatgtgaaagggaaacacctttgtccaagtcccc tatttcccggaccttctaagcccaaagatcccaaatttttgggtgct ggtggtggttggtggagtcctggcttgctatagcttgctagtaacagtg gcctttattattttctgggtgaggagtaagaggagcaggctcctg cacagtgactacatgaacatgactccccgccgcccgggcccacccgca agcattaccagccctatgccccaccacgcgacttcgcagc ctatcgctcacgcgtgaagttcagcaggagcgcagacgcccccgcgtac cagcagggccagaaccagctctataacgagctcaatctag gacgaagagaggagtacgatgtttggacaaaagacgtggccgggaccc tgagatgggggaaagccgagaaggaagaaccctcagg aaggcctgtacaatgaactgcagaaagataagatggcggaggcctacag tgagattgggatgaaaggcgagcgccggaggggcaagg ggcacgatggcctttaccagggtctcagtacagccaccaaggacaccta cgacgcccttcacatgcaggccctgcccctcgctga.

In some embodiments, the BCMA-CAR comprises a nucleic acid sequence at least 70% identical to SEQ ID NO: 42. In some embodiments, the BCMA-CAR comprises a nucleic acid sequence at least 75% identical to SEQ ID NO: 42. In some embodiments, the BCMA-CAR comprises a nucleic acid sequence at least 80% identical to SEQ ID NO: 42. In some embodiments, the BCMA-CAR comprises a nucleic acid sequence at least 85% identical to SEQ ID NO: 42. In some embodiments, the BCMA-CAR comprises a nucleic acid sequence at least 90% identical to SEQ ID NO: 42. In some embodiments, the BCMA-CAR comprises a nucleic acid sequence at least 95% identical to SEQ ID NO: 42. In some embodiments, the BCMA-CAR comprises a nucleic acid sequence at least 97% identical to SEQ ID NO: 42. In some embodiments, the BCMA-CAR comprises a nucleic acid sequence at least 99% identical to SEQ ID NO: 42.

In some embodiments, the BCMA-CAR is linked to IL-15, through a linker and a cleavage peptide, comprising SEQ ID NO: 45:

(SEQ ID NO: 45)
MEFGLSWLFLVAILKGVQCEVQLVESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTTVTVSSGGGGSGGG

GSGGGGSDIVMTQSPSFLSASVGDRVTITCRASQGISSYLAWYQQKPGK

APKLLIYAASTLQSGVPSRFSGSGSGTEFTLTISSLQPEDFATYYCQQL

NSYPFTFGPGTKVDIKRAAAIEVMYPPPYLDNEKSNGTIIHVKGKHLCP

SPLFPGPSKPKDPKFWVLVVVGGVLACYSLLVTVAFIIFWVRSKRSRLL

HSDYMNMTPRRPGPTRKHYQPYAPPRDFAAYRSRVKFSRSADAPAYQQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPRGP

QCTNYALLKLAGDVESNPGPMRISKPHLRSISIQCYLCLLLNSHFLTEA

GIHVFILGCFSAGLPKTEANWVNVISDLKKIEDLIQSMHIDATLYTESD

VHPSCKVTAMKCFLLELQVISLESGDASIHDTVENLIILANNSLSSNGN

VTESGCKECEELEEKNIKEFLQSFVHIVQMFINTS

BCMA-CAR linked to IL-15 represented by SEQ ID NO: 45 is sometimes referred as BCMA28-1 in this specification. Another BCMA-CAR linked to IL-15, in which CD28 hinge is replaced by IgG1 hinge, is sometimes referred as BCMAIg1 in this specification.

In some embodiments, the BCMA-CAR-IL15 comprises an amino acid sequence at least 70% identical to SEQ ID NO: 45. In some embodiments, the BCMA-CAR-IL15 comprises an amino acid sequence at least 75% identical to SEQ ID NO: 45. In some embodiments, the BCMA-CAR-IL15 comprises an amino acid sequence at least 80% identical to SEQ ID NO: 45. In some embodiments, the BCMA-CAR-IL15 comprises an amino acid sequence at least 85% identical to SEQ ID NO: 45. In some embodiments, the BCMA-CAR-IL15 comprises an amino acid sequence at least 90% identical to SEQ ID NO: 45. In some embodiments, the BCMA-CAR-IL15 comprises an amino acid sequence at least 95% identical to SEQ ID NO: 45. In some embodiments, the BCMA-CAR-IL15 comprises an amino acid sequence at least 97% identical to SEQ ID NO: 45. In some embodiments, the BCMA-CAR-IL15 comprises an amino acid sequence at least 99% identical to SEQ ID NO: 45.

In some embodiments, the BCMA-CAR-IL-15 comprises:

atggaatttggactgtcatggcttttcttgtcgccatcctgaaagggg
tacagtgtgaagtgcaactggtcgaatctgggggagacgttgtcc
agcccggagtctttgcggttgtcatgcgcagcttcaggttttactttt
ctcttcatacgccatccattgggttcggcaagcgcctggtaaggg
actcgaatgggttgcagtgacctggcatgacggatcaaacaagtattat
gcagaatcagtaatgggcaggtttaccatttcacgcgacaatag
caaaaatacactttatttgcacatgaattcactcagagccgaagatacc
ggcgtctattattgcgccagagcaaaatttggggagccacagta
cttccaacattggggacaaggcactaccgtcaccgtgagttcaggcggg
gggggatcaggcggaggaggttcaggcggcggcggcagt
gacatagtgatgactcagagtcctcattttgagcgcaagtgttgggg
atagggtcactataacgtgtagagcatctcaaggcatttcttcatat
ttggcctggtatcaacagaaacctggaaaggccccaaagctccttattt
acgctgcatcaaccctgcaatctggegtcccaagccgattctct
gggtctggaagcggcacagaattaccctgactatatcatctctccaac
ctgaagattttgccacctattattgtcagcaattgaattcatacccg
ttcacattcggccctggaactaaagtcgacatcaagcggggggccgcaat
tgaagttatgtatcctcctccttacctagacaatgagaagagc
aatgaaccattatccatgtgaaagggaaacacctttgtccaagtcccc
tatttcccggaccttctaagcccaaagatcccaaattttgggtgct
ggtggtggttggtggagtcctggcttgctatagcttgctagtaacagtg
gcctttattattttctgggtgaggagtaagaggagcaggctcctg
cacagtgactacatgaacatgactcccgccgccccgggccacccgca
agcattaccagcccatgcccaccacgcgacttcgcagc
ctatcgctcacgcgtgaagttcagcaggagcgcagacgccccgcgtac
cagcagggccagaaccagctctataacgagctcaatctag
gacgaagagaggagtacgatgttttggacaaaagacgtggccgggaccc
tgagatgggggaaagccgagaaggaagaaccctcagg aaggcctgtacaatgaactgcagaaagataagatggcggaggcctacag
tgagattgggatgaaaggcgagcgccggaggggcaagg
ggcacgatggcctttaccagggtctcagtacagccaccaaggacaccta
cgacgcccttcacatgcaggccctgcccctcgcggaccg
cagtgtactaattatgctctcttgaaattggctggagatgttgagagca
atcccgggcccatgcgcattagcaagccccacctgcggagcatc
agcatccagtgctacctgtgcctgctgctgaacagccacttcctgaccg
aggccggcatccacgtgttcatcctgggctgcttcagcgccgg
actgcccaagaccgaggccaactgggtgaacgtgatcagcgacctgaag
aagatcgaggacctgatccagagcatgcacatcgacgcc
accctgtacaccgagagcgacgtgcaccccagctgcaaggtgaccgcca
tgaagtgctttctgctggaactgcaggtgatcagcctggaa
agcggcgacgccagcatccacgacaccgtggagaacctgatcatcctgg
ccaacaacagcctgagcagcaacggcaacgtgaccgag
agcggctgcaaagagtgcgaggaactggaagagaagaacatcaaagagt
ttctgcagagcttcgtgcacatcgtgcagatgttcatcaac
accagctga.

In some embodiments, the BCMA-CAR-IL15 comprises a nucleic acid sequence at least 70% identical to SEQ ID NO: 46. In some embodiments, the BCMA-CAR-IL15 comprises a nucleic acid sequence at least 75% identical to SEQ ID NO: 46. In some embodiments, the BCMA-CAR comprises a nucleic acid sequence at least 80% identical to SEQ ID NO: 46. In some embodiments, the BCMA-CAR-IL15 comprises a nucleic acid sequence at least 85% identical to SEQ ID NO: 46. In some embodiments, the BCMA-CAR-IL15 comprises a nucleic acid sequence at least 90% identical to SEQ ID NO: 46. In some embodiments, the BCMA-CAR-IL15 comprises a nucleic acid sequence at least 95% identical to SEQ ID NO: 46. In some embodiments, the BCMA-CAR-IL15 comprises a nucleic acid sequence at least 97% identical to SEQ ID NO: 46. In some embodiments, the BCMA-CAR-IL15 comprises a nucleic acid sequence at least 99% identical to SEQ ID NO: 46.

In some embodiments, the BCMA-CAR comprises an amino acid sequence comprising:

(SEQ ID NO: 20)
MEFGLSWLFLVAILKGVQCQITLRESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTLVTVSSGGGGSGGG

GSGGGGSDIVMTQSPSFLSASVGDRVTITCRASQGINNYLAWYQQKPGI

APKLLIYAASTLQSGVPSRFGGSGSGTEFTLTISSLQPEDFATYYCQQL

KSYPFTFGPGTKVEIKRAAAIEVMYPPPYLDNEKSNGTIIHVKGKHLCP

SPLFPGPSKPKDPKFWVLVVVGGVLACYSLLVTVAFIIFWVRSKRSRLL

HSDYMNMTPRRPGPTRKHYQPYAPPRDFAAYRSRVKFSRSADAPAYQQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

In some embodiments, the BCMA-CAR comprises an amino acid sequence at least 70% identical to SEQ ID NO: 20. In some embodiments, the BCMA-CAR comprises an amino acid sequence at least 75% identical to SEQ ID NO: 20. In some embodiments, the BCMA-CAR comprises an amino acid sequence at least 80% identical to SEQ ID NO: 20. In some embodiments, the BCMA-CAR comprises an amino acid sequence at least 85% identical to SEQ ID NO: 20. In some embodiments, the BCMA-CAR comprises an amino acid sequence at least 90% identical to SEQ ID NO: 20. In some embodiments, the BCMA-CAR comprises an amino acid sequence at least 95% identical to SEQ ID NO: 20. In some embodiments, the BCMA-CAR comprises an amino acid sequence at least 97% identical to SEQ ID NO: 20. In some embodiments, the BCMA-CAR comprises an amino acid sequence at least 99% identical to SEQ ID NO: 20.

In some embodiments, the BCMA-CAR comprises an nucleic acid sequence comprising:

(SEQ ID NO: 43)
atggaattcgggctgtcctggcttttcttggtcgcaattcttaaggg cgtccaatgtcagataactctgcgcgagtcaggaggagacgtggtg caaccgggcagatctctcaggctttcatgtgccgccagtggcttcac atttagctcttatgcaatacattgggtcaggcaggctcctggcaag ggcttggaatgggtagcggttacctggcatgatggatctaacaaata ctacgccgagtctgttatggtcgattcacaatttctcgagacaatt caaaaaacacactctacctgcatatgaactcacttagagcagaggac actggtgtctattactgcgccagagcaaaattcggcgagccaca gtatttccagcactggggacaaggaaccctcgtaacagtatctagtg ggggcggagggtctggaggagggggagcgggggaggcgg ctctgatattgttatgacccaatcaccatcttttctgagcgctagtg tcggcgacagggttacaatcacatgccgagcaagccaaggaatcaa caattatctcgcatggtatcaacaaaaaccaggtatcgccccgaaac ttcttatttacgcagcatcaaccctgcaaagcggagttccttctaga tttggtggcagcggctccgggactgaattcactcttactatttcctc ccttcaacccgaagatttcgccacatattactgccagcagcttaagt catacccctt cacttttggcccaggaactaaagttgaaatcaaacgg gcggccgcaattgaagttatgtatcctcctccttacctagacaatga gaagagcaatggaaccattatccatgtgaaagggaaacacctttgtc caagtcccctatttcccggaccttctaagcccaaagatcccaaattt tgggtgctggtggtggttggtggagtcctggcttgctatagcttgct agtaacagtggcctttattattttctgggtgaggagtaagaggagca ggctcctgcacagtgactacatgaacatgactcccgccgccccggg cccaccgcaagcattaccagccctatgccccaccacgcgacttc gcagcctatcgctcacgcgtgaagttcagcaggagcgcagacgcccc cgcgtaccagcagggccagaaccagctctataacgagctca atctaggacgaagagaggagtacgatgttttggacaaaagacgtggc cgggaccctgagatggggggaaagccgagaaggaagaacc ct caggaaggcctgt acaatgaactgcagaaagat aagat ggcggag gcct acagtgagattgggatgaaaggcgagcgccggagggg caaggggcacgatggcctttaccagggtctcagtacagccaccaagg acacctacgacgcccttcacatgcaggccctgccccctcgctg a In some embodiments, the BCMA-CAR comprises a nucleic acid sequence at least 70% identical to SEQ ID NO: 43. In some embodiments, the BCMA-CAR comprises a nucleic acid sequence at least 75% identical to SEQ ID NO: 43. In some embodiments, the BCMA-CAR comprises a nucleic acid sequence at least 80% identical to SEQ ID NO: 43. In some embodiments, the BCMA-CAR comprises a nucleic acid sequence at least 85% identical to SEQ ID NO: 43. In some embodiments, the BCMA-CAR comprises a nucleic acid sequence at least 90% identical to SEQ ID NO: 43. In some embodiments, the BCMA-CAR comprises a nucleic acid sequence at least 95% identical to SEQ ID NO: 43. In some embodiments, the BCMA-CAR comprises a nucleic acid sequence at least 97% identical to SEQ ID NO: 43. In some embodiments, the BCMA-CAR comprises a nucleic acid sequence at least 99% identical to SEQ ID NO: 43.

In some embodiments, the BCMA-CAR is linked to IL-15, through a linker and a cleavage peptide, comprising SEQ ID NO: 47:

(SEQ ID NO: 47)
MEFGLSWLFLVAILKGVQCQITLRESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTLVTVSSGGGGSGGG

GSGGGGSDIVMTQSPSFLSASVGDRVTITCRASQGINNYLAWYQQKPGI

APKLLIYAASTLQSGVPSRFGGSGSGTEFTLTISSLQPEDFATYYCQQL

KSYPFTFGPGTKVEIKRAAAIEVMYPPPYLDNEKSNGTIIHVKGKHLCP

SPLFPGPSKPKDPKFWVLVVVGGVLACYSLLVTVAFIIFWVRSKRSRLL

HSDYMNMTPRRPGPTRKHYQPYAPPRDFAAYRSRVKFSRSADAPAYQQG

QNQLYNELNLGRREEYDVLDKRRGRDPEMGGKPRRKNPQEGLYNELQKD

KMAEAYSEIGMKGERRRGKGHDGLYQGLSTATKDTYDALHMQALPPRGP

QCTNYALLKLAGDVESNPGPMRISKPHLRSISIQCYLCLLLNSHFLTEA

GIHVFILGCFSAGLPKTEANWVNVISDLKKIEDLIQSMHIDATLYTESD

VHPSCKVTAMKCFLLELQVISLESGDASIHDTVENLIILANNSLSSNGN

VTESGCKECEELEEKNIKEFLQSFVHIVQMFINTS

BCMA-CAR linked to IL-15 represented by SEQ ID NO: 47 is sometimes referred as BCMA28-2 in this specification. Another BCMA-CAR linked to IL-15, in which CD28 hinge is replaced by IgG1 hinge, is sometimes referred as BCMAIg2 in this specification.

In some embodiments, the BCMA-CAR-IL15 comprises an amino acid sequence at least 70% identical to SEQ ID NO: 47. In some embodiments, the BCMA-CAR-IL15 comprises an amino acid sequence at least 75% identical to SEQ ID NO: 47. In some embodiments, the BCMA-CAR-IL15 comprises an amino acid sequence at least 80% identical to SEQ ID NO: 47. In some embodiments, the BCMA-CAR- IL15 comprises an amino acid sequence at least 85% identical to SEQ ID NO: 47. In some embodiments, the BCMA-CAR-IL15 comprises an amino acid sequence at least 90% identical to SEQ ID NO: 47. In some embodiments, the BCMA-CAR-IL15 comprises an amino acid sequence at least 95% identical to SEQ ID NO: 47. In some embodiments, the BCMA-CAR-IL15 comprises an amino acid sequence at least 97% identical to SEQ ID NO: 47. In some embodiments, the BCMA-CAR-IL15 comprises an amino acid sequence at least 99% identical to SEQ ID NO: 47.

In some embodiments, the BCMA-CAR-IL-15 comprises:

```
(SEQ ID NO: 48)
atggaattcgggctgtcctggcttttcttggtcgcaattcttaagggc gtccaatgtcagataactctgcgcgagtcaggaggagacgtggtg caaccgggcagatctctcaggctttcatgtgccgccagtggcttcaca tttagctcttatgcaatacattgggtcaggcaggctcctggcaag ggcttggaatgggtagcggttacctggcatgatggatctaacaaatac tacgccgagtctgttatgggtcgattcacaatttctcgagacaatt caaaaaacacactctacctgcatatgaactcacttagagcagaggacac tggtgtctattactgcgccagagcaaaattcggcgagccaca gtatttccagcactggggacaaggaaccctcgtaacagtatctagtgg gggcggagggtctggaggagggggggagcggggggaggcgg ctctgatattgttatgacccaatcaccatcttttctgagcgctagtgt cggcgacagggttacaatcacatgccgagcaagccaaggaatcaa caattatctcgcatggtatcaacaaaaaccaggtatcgccccgaaact tcttatttacgcagcatcaaccctgcaaagcggagttccttctaga tttggtggcagcggctccgggactgaattcactcttactatttcctcc cttcaacccgaagatttcgccacatattactgccagcagcttaagtca tacccottcacttttggccaggaactaaagttgaaatcaaacggggg ccgcaattgaagttatgtatcctcctccttacctagacaatgaga agagcaatggaaccattatccatgtgaaagggaaacacctttgtccaa gtcccctatttcccggaccttctaagcccaaagatcccaaattttg ggtgctggtggtggttggtggagtcctggcttgctatagcttgctagt aacagtggcctttattattttctgggtgaggagtaagaggagcagg ctcctgcacagtgactacatgaacatgactccccgccgcccgggccc acccgcaagcattaccagccctatgccccaccacgcgacttc gcagcctatcgctcacgcgtgaagttcagcaggagcgcagacgccccc gcgtaccagcagggccagaaccagctctataacgagctca atctaggacgaagagaggagtacgatgttttggacaaaagacgtggcc gggaccctgagatggggggaaagccgagaaggaagaacc ctcaggaaggcctgtacaatgaactgcagaaagataagatggcggagg cctacagtgagattgggatgaaaggcgagcgccggaggg caaggggcacgatggcctttaccagggtctcagtacagccaccaagga cacctacgacgcccttcacatgcaggccctgcccctcgcg
```

```
-continued
gaccgcagtgtactaattatgctctcttgaaattggctggagatgttg agagcaatcccgggcccatgcgcattagcaagccccacctgcgg agcatcagcatccagtgctacctgtgcctgctgctgaacagccacttc ctgaccgaggccggcatccacgtgttcatcctgggctgcttcag cgccggactgcccaagaccgaggccaactgggtgaacgtgatcagcga cctgaagaagatcgaggacctgatccagagcatgcacatc gacgccaccctgtacaccgagagcgacgtgcaccccagctgcaaggtg accgccatgaagtgctttctgctggaactgcaggtgatcagc ctggaaagcggcgacgccagcatccacgacaccgtggagaacctgatc atcctggccaacaacagcctgagcagcaacggcaacgtga ccgagagcggctgcaaagagtgcgaggaactggaagagaagaacatca aagagtttctgcagagcttcgtgcacatcgtgcagatgttca tcaacaccagctga
```

In some embodiments, the BCMA-CAR-IL15 comprises a nucleic acid sequence at least 70% identical to SEQ ID NO: 48. In some embodiments, the BCMA-CAR-IL15 comprises a nucleic acid sequence at least 75% identical to SEQ ID NO: 48. In some embodiments, the BCMA-CAR comprises a nucleic acid sequence at least 80% identical to SEQ ID NO: 48. In some embodiments, the BCMA-CAR-IL15 comprises a nucleic acid sequence at least 85% identical to SEQ ID NO: 48. In some embodiments, the BCMA-CAR-IL15 comprises a nucleic acid sequence at least 90% identical to SEQ ID NO: 48. In some embodiments, the BCMA-CAR-IL15 comprises a nucleic acid sequence at least 95% identical to SEQ ID NO: 48. In some embodiments, the BCMA-CAR-IL15 comprises a nucleic acid sequence at least 97% identical to SEQ ID NO: 48. In some embodiments, the BCMA-CAR-IL15 comprises a nucleic acid sequence at least 99% identical to SEQ ID NO: 48.

In some embodiments, the BCMA-CAR comprises an amino acid sequence comprising:

```
(SEQ ID NO: 21)
MEFGLSWLFLVAILKGVQCQITLRESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTLVTVSSGGGGSGGG

GSGGGGSDIVMTQSPSFLSASVGDRVTITCRASQGISSYLAWYQQKPGK

APKLLIYAASTLQSGVPSRFSGSGSGTEFTLTISSLQPEDFATYYCQQL

NSYPWTFGQGTKVDIKRTVTVSSQDPAEPKSPDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPGKKDPKFWVLVVVGGVLACYSLLVTVAFIIFWVRSKR

SRLLHSDYMNMTPRRPGPTRKHYQPYAPPRDFAAYRSRVKFSRSADAPA
```

YQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALP

PR

In some embodiments, the BCMA-CAR comprises an amino acid sequence at least 70% identical to SEQ ID NO: 21. In some embodiments, the BCMA-CAR comprises an amino acid sequence at least 75% identical to SEQ ID NO: 21. In some embodiments, the BCMA-CAR comprises an amino acid sequence at least 80% identical to SEQ ID NO: 21. In some embodiments, the BCMA-CAR comprises an amino acid sequence at least 85% identical to SEQ ID NO: 21. In some embodiments, the BCMA-CAR comprises an amino acid sequence at least 90% identical to SEQ ID NO: 21. In some embodiments, the BCMA-CAR comprises an amino acid sequence at least 95% identical to SEQ ID NO: 21. In some embodiments, the BCMA-CAR comprises an amino acid sequence at least 97% identical to SEQ ID NO: 21. In some embodiments, the BCMA-CAR comprises an amino acid sequence at least 99% identical to SEQ ID NO: 21.

In some embodiments, the BCMA-CAR comprises an nucleic acid sequence comprising:

(SEQ ID NO: 44)
atggaattcggattgtcatggttgttcctcgtcgcaattctcaagggc gtgcagtgccaaattactcttcgagagtccggcggagatgtggtac agccagggagaagcctgagactctcctgtgcagcaagcggatttacct tttcttcttacgctatccactgggttagacaggctcccggtaagg gactggaatgggtcgcagtaacatggcacgacggttcaaataagtact acgcagagtcagtcatgggaaggtttactatttcacgggacaat tctaagaacacactctacctgcatatgaactccctcagagctgaagac accggcgtatattattgtgctagagctaaattttggagaaccacagt attttcaacactggggccaaggcacacttgtaacggtttcaagcggtg gtgggggtctggcggaggaggtagtggaggtggaggctccg atatcgttatgacacaatcacccagcttcttgtcagcttctgttggtg atcgggtaacaattacttgtcgcgcatctcagggtatcagttcatatct ggcatggtatcagcaaaagcctggaaaagccctaaacttctgattta cgccgcgagcacactgcaaagtggagttccgtcaagattctctg gctctgggtccggtaccgaatttactttgactatcagctcactccaac ctgaggatttcgccacgtactattgccaacagcttaactcctatcctt ggacatttggtcagggcactaaagttgatattaaacgtacggtcactg tctcttcacaggatcccgccgagcccaaatctcctgacaaaactc acacatgccaccgtgcccagcacctgaactcctgggggggaccgtcag tcttcctcttccccccaaaacccaaggacaccctcatgatctc ccggacccctgaggtcacatgcgtggtggtggacgtgagccacgaaga ccctgaggtcaagttcaactggtacgtggacggcgtggagg tgcataatgccaagacaaagccgcggggaggagcagtacaacagcacgt accgtgtggtcagcgtcctcaccgtcctgcaccaggactgg ctgaatggcaaggagtacaagtgcaaggtctccaacaaagcccctccca gcccccatcgagaaaaccatctccaaagccaaagggcagcc ccgagaaccacaggtgtacaccctgcccccatcccgggatgagctgac caagaaccaggtcagcctgacctgcctggtcaaaggcttcta tcccagcgacatcgccgtggagtgggagagcaatgggcaaccggagaa caactacaagaccacgcctcccgtgctggactccgacggc tccttcttcctctacagcaagctcaccgtggacaagagcaggtggcag caggggaacgtcttctcatgctccgtgatgcatgaggctctgca caaccactacacgcagaagagcctctccctgtctccgggtaaaaaaga tcccaaattttgggtgctggtggtggttggtggagtcctggcttg ctatagcttgctagtaacagtggcctttattattttctgggtgaggag taagaggagcaggctcctgcacagtgactacatgaacatgactccc cgccgccccgggcccaccgcaagcattaccagccctatgccccacca cgcgacttcgcagcctatcgctcacgcgtgaagttcagcag gagcgcagacgcccccgcgtaccagcagggccagaaccagctctataa cgagctcaatctaggacgaagagaggagtacgatgttttgg acaaaagacgtggccgggaccctgagatgggggggaaagccgagaagga agaaccctcaggaaggcctgtacaatgaactgcagaaag ataagatggcggaggcctacagtgagattgggatgaaaggcgagcgcc ggagggggcaaggggcacgatggcctttaccagggtctcag tacagccaccaaggacacctacgacgcccttcacatgcaggccctgcc cctcgctgac In some embodiments, the BCMA-CAR comprises a nucleic acid sequence at least 70% identical to SEQ ID NO: 44. In some embodiments, the BCMA-CAR comprises a nucleic acid sequence at least 75% identical to SEQ ID NO: 44. In some embodiments, the BCMA-CAR comprises a nucleic acid sequence at least 80% identical to SEQ ID NO: 44. In some embodiments, the BCMA-CAR comprises a nucleic acid sequence at least 85% identical to SEQ ID NO: 44. In some embodiments, the BCMA-CAR comprises a nucleic acid sequence at least 90% identical to SEQ ID NO: 44. In some embodiments, the BCMA-CAR comprises a nucleic acid sequence at least 95% identical to SEQ ID NO: 44. In some embodiments, the BCMA-CAR comprises a nucleic acid sequence at least 97% identical to SEQ ID NO: 44. In some embodiments, the BCMA-CAR comprises a nucleic acid sequence at least 99% identical to SEQ ID NO: 44.

In some embodiments, the BCMA-CAR is linked to IL-15, through a linker and a cleavage peptide, comprising SEQ ID NO: 49:

(SEQ ID NO: 49)
MEFGLSWLFLVAILKGVQCQITLRESGGDVVQPGRSLRLSCAASGFTFS

SYAIHWVRQAPGKGLEWVAVTWHDGSNKYYAESVMGRFTISRDNSKNTL

YLHMNSLRAEDTGVYYCARAKFGEPQYFQHWGQGTLVTVSSGGGGSGGG

GSGGGGSDIVMTQSPSFLSASVGDRVTITCRASQGISSYLAWYQQKPGK

APKLLIYAASTLQSGVPSRFSGSGSGTEFTLTISSLQPEDFATYYCQQL

NSYPWTFGQGTKVDIKRTVTVSSQDPAEPKSPDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPGKKDPKFWVLVVVGGVLACYSLLVTVAFIIFWVRSKR

SRLLHSDYMNMTPRRPGPTRKHYQPYAPPRDFAAYRSRVKFSRSADAPA

YQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALP

PRGPQCTNYALLKLAGDVESNPGPMRISKPHLRSISIQCYLCLLLNSHF

LTEAGIHVFILGCFSAGLPKTEANWVNVISDLKKIEDLIQSMHIDATLY

TESDVHPSCKVTAMKCFLLELQVISLESGDASIHDTVENLIILANNSLS

SNGNVTESGCKECEELEEKNIKEFLQSFVHIVQMFINTS

In some embodiments, the BCMA-CAR-IL15 comprises an amino acid sequence at least 70% identical to SEQ ID NO: 49. In some embodiments, the BCMA-CAR-IL15 comprises an amino acid sequence at least 75% identical to SEQ ID NO: 49. In some embodiments, the BCMA-CAR-IL15 comprises an amino acid sequence at least 80% identical to SEQ ID NO: 49. In some embodiments, the BCMA-CAR-IL15 comprises an amino acid sequence at least 85% identical to SEQ ID NO: 49. In some embodiments, the BCMA-CAR-IL15 comprises an amino acid sequence at least 90% identical to SEQ ID NO: 49. In some embodiments, the BCMA-CAR-IL15 comprises an amino acid sequence at least 95% identical to SEQ ID NO: 49. In some embodiments, the BCMA-CAR-IL15 comprises an amino acid sequence at least 97% identical to SEQ ID NO: 49. In some embodiments, the BCMA-CAR-IL15 comprises an amino acid sequence at least 99% identical to SEQ ID NO: 49.

In some embodiments, the BCMA-CAR-IL-15 comprises:

```
                                           (SEQ ID NO: 50)
atggaattcggattgtcatggttgttcctcgtcgcaattctcaagggcg tgcagtgccaaattactcttcgagagtccggcggagatgtggtac agccagggagaagcctgagactctcctgtgcagcaagcggatttacctt ttcttcttacgctatccactgggttagacaggctcccggtaagg gactggaatgggtcgcagtaacatggcacgacggttcaaataagtacta cgcagagtcagtcatgggaaggtttactatttcacgggacaat tctaagaacacactctacctgcatatgaactccctcagagctgaagaca ccggcgtatattattgtgctagagctaaatttggagaaccacagt attttcaacactggggccaaggcacacttgtaacggtttcaagcggtgg tgggggctggcggaggaggtagtggaggtggaggctccg atatcgttatgacacaatcacccagcttcttgtcagcttctgttggtga tcgggtaacaattacttgtcgcgcatctcagggtatcagttcatatct ggcatggtatcagcaaaagcctggaaaagcccctaaacttctgatttac
``` gccgcgagcacactgcaaagtggagttccgtcaagattctctg gctctgggtccggtaccgaatttactttgactatcagctcactccaacc tgaggatttcgccacgtactattgccaacagcttaactcctatcctt ggacatttggtcagggcactaaagttgatattaaacgtacggtcactgt ctcttcacaggatcccgccgagcccaaatctcctgacaaaactc acacatgcccaccgtgcccagcacctgaactcctggggggaccgtcagt cttcctcttccccccaaaacccaaggacaccctcatgatctc ccggaccctgaggtcacatgcgtggtggtggacgtgagccacgaagac cctgaggtcaagttcaactggtacgtggacggcgtggagg tgcataatgccaagacaaagccgcggaggagcagtacaacagcacgta ccgtgtggtcagcgtcctcaccgtcctgcaccaggactgg ctgaatggcaaggagtacaagtgcaaggtctccaacaaagcccctcccag cccccatcgagaaaaccatctccaaagccaaagggcagcc ccgagaaccacaggtgtacaccctgcccccatcccgggatgagctgacc aagaaccaggtcagcctgacctgcctggtcaaaggcttcta tcccagcgacatcgccgtggagtgggagagcaatgggcaaccggagaac aactacaagaccacgcctcccgtgctggactccgacggc tccttcttcctctacagcaagctcaccgtggacaagagcaggtggcagc aggggaacgtcttctcatgctccgtgatgcatgaggctctgca caaccactacacgcagaagagcctctccctgtctccgggtaaaaaagat cccaaattttgggtgctggtggtggttggtggagtcctggcttg ctatagcttgctagtaacagtggcctttattattttctgggtgaggagt aagaggagcaggctcctgcacagtgactacatgaacatgactccc cgccgccccgggcccacccgcaagcattaccagccctatgccccaccac gcgacttcgcagcctatcgctcacgcgtgaagttcagcag gagcgcagacgccccgcgtaccagcagggccagaaccagctctataac gagctcaatctaggacgaagagaggagtacgatgttttgg acaaaagacgtggccgggaccctgagatgggggaaagccgagaaggaa gaaccctcaggaaggcctgtacaatgaactgcagaaag ataagatggcggaggcctacagtgagattggatgaaaggcgagcgcg gaggggcaaggggcacgatggcctttaccagggtctcag tacagccaccaaggacacctacgacgcccttcacatgcaggccctgccc cctcgcggaccgcagtgtactaattatgctctcttgaaattgg ctggagatgttgagagcaatcccgggcccatgcgcattagcaagcccca cctgcggagcatcagcatccagtgctacctgtgcctgctgct gaacagccacttcctgaccgaggccggcatccacgtgttcatcctgggc tgcttcagcgccggactgcccaagaccgaggccaactgggt gaacgtgatcagcgacctgaagaagatcgaggacctgatccagagcatg cacatcgacgccacccctgtacaccgagagcgacgtgcac cccagctgcaaggtgaccgccatgaagtgctttctgctggaactgcagg

```
-continued
tgatcagcctggaaagcggcgacgccagcatccacgacac cgtggagaacctgatcatcctggccaacaacagcctgagcagcaacggc aacgtgaccgagagcggctgcaaagagtgcgaggaactg gaagagaagaacatcaaagagtttctgcagagcttcgtgcacatcgtgc agatgttcatcaacaccagctga
```

In some embodiments, the BCMA-CAR-IL15 comprises a nucleic acid sequence at least 70% identical to SEQ ID NO: 50. In some embodiments, the BCMA-CAR-IL15 comprises a nucleic acid sequence at least 75% identical to SEQ ID NO: 50. In some embodiments, the BCMA-CAR comprises a nucleic acid sequence at least 80% identical to SEQ ID NO: 50. In some embodiments, the BCMA-CAR-IL15 comprises a nucleic acid sequence at least 85% identical to SEQ ID NO: 50. In some embodiments, the BCMA-CAR-IL15 comprises a nucleic acid sequence at least 90% identical to SEQ ID NO: 50. In some embodiments, the BCMA-CAR-IL15 comprises a nucleic acid sequence at least 95% identical to SEQ ID NO: 50. In some embodiments, the BCMA-CAR-IL15 comprises a nucleic acid sequence at least 97% identical to SEQ ID NO: 50. In some embodiments, the BCMA-CAR-IL15 comprises a nucleic acid sequence at least 99% identical to SEQ ID NO: 50.

Embodiments of the disclosure encompass cells that express one or more CARs and one or more suicide genes as encompassed herein. The NK cell comprises a recombinant nucleic acid that encodes one or more CARs and one or more engineered nonsecretable, membrane bound TNF-alpha mutant polypeptides, in specific embodiments. In specific embodiments, in addition to expressing one or more CARs and TNF-alpha mutant polypeptides, the cell also comprises a nucleic acid that encodes one or more therapeutic gene products.

Vectors

In certain aspects, provided herein are vectors comprising a polynucleotide of the present invention. In some embodiments, the vector is selected from a DNA vector, an RNA vector, a plasmid, a lentiviral vector, an adenovirus vector, a AAV vector, or a retroviral vector. In some embodiments, the vector can be a viral vector. Examples of viral vectors include at least retroviral, lentiviral, adenoviral, or adeno-associated viral vectors. Examples of non-viral vectors include at least plasmids, transposons, lipids, nanoparticles, and so forth.

In cases wherein the immune cell is transduced with a vector encoding the genetically engineered receptor and also requires transduction of another gene or genes into the cell, such as a suicide gene and/or cytokine and/or an optional therapeutic gene product, the antigen-targeting receptor, suicide gene, cytokine, and optional therapeutic gene may or may not be comprised on or with the same vector. In some cases, the CAR, suicide gene, cytokine, and optional therapeutic gene are expressed from the same vector molecule, such as the same viral vector molecule. In such cases, the expression of the CAR, suicide gene, cytokine, and optional therapeutic gene may or may not be regulated by the same regulatory element(s). When the CAR, suicide gene, cytokine, and optional therapeutic gene are on the same vector, they may or may not be expressed as separate polypeptides. In cases wherein they are expressed as separate polypeptides, they may be separated on the vector by a 2A element or IRES element (or both kinds may be used on the same vector once or more than once), for example.

In some embodiments, the cytokines and suicide genes are expressed from the same polypeptide, where they are separated by a 2A element. In some embodiments, the 2A element can induce ribosomal skipping during translation of a protein in a cell.

In some embodiments, the 2A element comprises amino acid sequence of:

(SEQ ID NO: 53)
QCTNYALLKLAGDVESNPGP.

Cells

The present disclosure encompasses immune cells or stem cells of any kind that harbor at least one vector that encodes the genetically engineered receptor comprising a BCMA CAR comprising a CD28 hinge domain. In some cases, different vectors encode the CAR vs. encodes the suicide gene and/or cytokine. The immune cells, including NK cells, may be derived from cord blood (including pooled cord blood from multiple sources), peripheral blood, induced pluripotent stem cells (iPSCs), hematopoietic stem cells (HSCs), bone marrow, or a mixture thereof. The NK cells may be derived from a cell line such as, but not limited to, NK-92 cells, for example. The NK cell may be a cord blood mononuclear cell, such as a CD56+NK cell.

The present disclosure encompasses immune or other cells of any kind, including conventional T cells, gamma-delta T cells, NKT and invariant NK T cells, regulatory T cells, macrophages, B cells, dendritic cells, mesenchymal stromal cells (MSCs), or a mixture thereof.

NK cells are critical component of the innate immune response and important players in the first line of defense against malignant cells. Ability of NK cells to kill malignant cells without prior sensitization contributes to its rapid action unlike T cells, which require recognition of tumor antigens presented in the context of HLA molecules.

In some cases, the NK cells have been expanded in the presence of an effective amount of universal antigen presenting cells (UAPCs), including in any suitable ratio. The cells may be cultured with the UAPCs at a ratio of 10:1 to 1:10; 9:1 to 1:9; 8:1 to 1:8; 7:1 to 1:7; 6:1 to 1:6; 5:1 to 1:5; 4:1 to 1:4; 3:1 to 1:3; 2:1 to 1:2; or 1:1, including at a ratio of 1:2, for example. In some cases, the NK cells were expanded in the presence of IL-2, such as at a concentration of 10-500, 10-400, 10-300, 10-200, 10-100, 10-50, 100-500, 100-400, 100-300, 100-200, 200-500, 200-400, 200-300, 300-500, 300-400, or 400-500 U/mL.

Following genetic modification with the vector(s), the NK cells may be immediately infused or may be stored. In certain aspects, following genetic modification, the cells may be propagated for days, weeks, or months ex vivo as a bulk population within about 1, 2, 3, 4, 5 days or more following gene transfer into cells. In a further aspect, the transfectants are cloned and a clone demonstrating presence of a single integrated or episomally maintained expression cassette or plasmid, and expression of the CAR is expanded ex vivo.

Embodiments of the disclosure encompass cells that express one or more CARs and one or more suicide genes as encompassed herein. The NK cell comprises a recombinant nucleic acid that encodes one or more CARs and one or more engineered nonsecretable, membrane bound TNF-alpha mutant polypeptides, in specific embodiments. In specific embodiments, in addition to expressing one or more CARs and TNF-alpha mutant polypeptides, the cell also comprises a nucleic acid that encodes one or more therapeutic gene products.

The cells may be obtained from an individual directly or may be obtained from a depository or other storage facility. The cells as therapy may be autologous or allogeneic with respect to the individual to which the cells are provided as therapy.

The cells may be from an individual in need of therapy for a medical condition, and following their manipulation to express the CAR, optional suicide gene, optional cytokine(s), and optional therapeutic gene product(s) (using standard techniques for transduction and expansion for adoptive cell therapy, for example), they may be provided back to the individual from which they were originally sourced. In some cases, the cells are stored for later use for the individual or another individual.

The immune cells may be comprised in a population of cells, and that population may have a majority that are transduced with one or more receptors and/or one or more suicide genes and/or one or more cytokines. A cell population may comprise 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of immune cells that are transduced with one or more CARs and/or one or more suicide genes and/or one or more cytokines. The one or more CARs and/or one or more suicide genes and/or one or more cytokines may be separate polypeptides.

The immune cells may be produced with the one or more CARs and/or one or more suicide genes and/or one or more cytokines for the intent of being modular with respect to a specific purpose. For example, cells may be generated, including for commercial distribution, expressing a CAR and/or one or more suicide genes and/or one or more cytokines (or distributed with a nucleic acid that encodes the mutant for subsequent transduction), and a user may modify them to express one or more other genes of interest (including therapeutic genes) dependent upon their intended purpose(s). For instance, an individual interested in treating antigen-positive cells, including antigen-positive cancer or infectious agent-infected cells, may obtain or generate suicide gene-expressing cells (or heterologous cytokine-expressing cells) and modify them to express a receptor comprising an antigen-specific scFv, or vice versa.

In particular embodiments, NK cells are utilized, and the genome of the transduced NK cells expressing the one or more CARs and/or one or more suicide genes and/or one or more cytokines may be modified. The genome may be modified in any manner, but in specific embodiments the genome is modified by CRISPR gene editing, for example. The genome of the cells may be modified to enhance effectiveness of the cells for any purpose.

As non-limiting examples, NK cells may express a BCMA binding CAR comprising an amino acid sequence selected from the group consisting of SEQ ID NOs: 19-21, 45, 47 and 49. In some examples, NK cells may comprises a polynucleotide comprising a nucleic acid sequence selected from the group consisting of SEQ ID NOs: 42-44, 46, 48 and 50.

III. Methods of Treatment

In various embodiments, diseased or other cells expressing a desired target on their surface are targeted for the purpose of improving a medical condition in an individual that has the medical condition or for the purpose of reducing the risk or delaying the severity and/or onset of the medical condition in an individual. In specific cases, cancer cells expressing the endogenous antigen are targeted for the purpose of killing the cancer cells. In other cases, cells infected with an infectious agent are targeted for the purpose of killing the infected cells.

In some embodiments, an antibody or fragment thereof described herein (e.g., an anti-BCMA antibody as described herein) is used in a method of treating one or more BCMA-associated conditions. In some embodiments, an antibody or fragment thereof described herein (e.g. an anti-BCMA antibody as described herein) is for use as a medicament. BCMA-associated conditions can include, without limitation, conditions that are caused by, include, include symptoms resulting in whole or in part from, or are known to occur in conjunction with BCMA expression.

In accordance with present disclosure, antibodies, fragments thereof, and CARs and compositions described herein can be used for treating BCMA associated cancers. A cancer is a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. In some embodiments, the "cancer" or "cancer tissue" comprises a solid tumor. Examples of cancers that can be treated by the methods of the present invention include, but are not limited to, cancers of the immune system including lymphoma, leukemia, myeloma, and other leukocyte malignancies.

In some aspects, the present invention provides a method for treating a cancer comprising administering an agent that binds BCMA (e.g. an anti-BCMA antibody described herein or fragment thereof).

In various embodiments, administration of an antibody or fragment thereof described herein (e.g., an anti-BCMA antibody described herein or fragment thereof) results in a decrease in the prevalence, frequency, level, and/or amount of one or more symptoms or biomarkers of a BCMA-associated condition as described herein or otherwise known in the art, e.g., a decrease of at least 3%, 4%, 5%, 6%, 7%, 8%, 9%, 10%, 15%, 20%, 25%, 30%, 35%, 40%, 45%, 50%, 60%, 70%, 80%, 90%, 95%, 99%, or 100% of one or more symptoms or biomarkers as compared to a prior measurement in the subject or to a reference value.

In some embodiments, administration of an antibody or fragment thereof described herein (e.g., an anti-BCMA antibody described herein) to a subject having cancer results in a greater decrease or improvement in one or more symptoms or biomarkers of cancer than does a reference antibody e.g., an antibody that cross-competes for BCMA binding, under comparable conditions.

In some embodiments, an antibody or fragment thereof described herein (e.g., an anti-BCMA antibody described herein) can be administered at a decreased dose amount as compared to a reference protein, e.g., an antibody that cross-competes for BCMA binding, while achieving an equal, equally effective, comparably effective, or substantially effective outcome, where the anti-BCMA antibody is administered in an identical, equivalent, or substantially equivalent formulation and/or by an identical, equivalent, or substantially equivalent route of administration as the reference (e.g., an antibody that cross-competes for BCMA binding). In some embodiments, an anti-BCMA antibody described herein can be administered at an increased interval as compared to a reference antibody (e.g., an antibody that cross-competes for BCMA binding) while achieving an equal, equally effective, comparably effective, or substantially effective outcome, where the anti-BCMA antibody is administered in an identical, equivalent, or substantially equivalent formulation and/or by an identical, equivalent, or substantially equivalent route of administration as the reference. In some embodiments, an anti-BCMA antibody described herein can be administered in a decreased number of unit dosages, and/or for a decreased period of treatment, as compared to a reference antibody while achieving an equal, equally effective, comparably effective, or substantially effective outcome, where the anti-BCMA antibody is administered in an identical, equivalent, or substantially equivalent formulation and/or by an identical, equivalent, or substantially equivalent route of administration as the reference (e.g., an antibody that cross-competes for BCMA binding).

In accordance with some such embodiments, an administered dose of an anti-BCMA antibody described herein may be less likely to elicit an adverse response when administered to a subject, e.g., an adverse immune response, than would an effective dose of a reference antibody, e.g., e.g., an antibody that cross-competes for BCMA binding. Accordingly, in various embodiments, an anti-BCMA antibody as disclosed herein may be less likely than a reference antibody, per unit of activity administered to induce an adverse reaction or side effect. In various embodiments, an anti-BCMA antibody as disclosed herein may less likely than a reference antibody, per unit of activity administered, to induce an adverse reaction or side effect having a particular degree of severity. In various embodiments, an anti-BCMA antibody as disclosed herein may induce one or more adverse reactions or side effects to a lesser degree or in fewer patients than a reference antibody, per unit of activity administered. Examples of adverse reactions or side effects that may be associated with the administration of an antibody capable of binding BCMA, may include headache, nasopharyngitis, back pain, nausea, diarrhea, hypertension, upper respiratory infection, abdominal pain, vomiting, anemia, cough, peripheral edema, and/or urinary tract infection.

In some embodiments, upon administration to a subject (e.g., at a single dose), an antibody or fragment thereof described herein (e.g., an anti-BCMA antibody described herein) is measured at an increased level in plasma at a defined time following administration (e.g., 1, 2, 3, 4, 5, 6, 7, 8, 9, 10, 11, 12, 13, 14, or more days), relative to level of a control at the same defined time (e.g., an antibody that cross-competes for BCMA binding). For example, at a defined time following administration of a single dose, a level of an anti-BCMA antibody described herein is at least 10%, 20%, 30%, 40%, 50%, 60%, 70%, 80%, 90%, 100%, 150%, 200%, 300%, 400%, or 500% higher than a corresponding level of a reference antibody.

In some embodiments, an antibody or fragment thereof described herein (e.g., an anti-BCMA antibody described herein) is measured at an increased level in plasma at a defined time (e.g., 1, 2, 3, 4, 5, 6, 7, 8, 9, 10, 11, 12, 13, 14, or more days) following administration (e.g., of a single dose), relative to level of a control at the same defined time. For example, at a defined time following administration, a level of an anti-BCMA antibody described herein is at least 10%, 20%, 30%, 40%, 50%, 60%, 70%, 80%, 90%, 100%, 150%, 200%, 300%, 400%, or 500% higher than a corresponding level of a reference antibody.

In some embodiments, an anti-BCMA antibody described herein has increased half-life (e.g., relative to a control, e.g., a reference antibody, e.g., an antibody that cross-competes for BCMA binding), and thus the anti-BCMA antibody can be administered to a subject at increased inter-dose intervals. For example, an anti-BCMA antibody can be administered once every week, every two weeks, every three weeks, every four weeks, every 6 weeks, every 8 weeks, or longer duration.

In some embodiments, a therapeutically effective amount of an anti-BCMA antibody or fragment thereof described herein is about 90%, 80%, 70%, 60%, 50%, 40%, 30%, 20%, 10%, or 5% of an effective amount of a reference therapeutic protein, e.g., an antibody that cross-competes for BCMA binding. In some embodiments, a single dose of an anti-BCMA antibody described herein achieves a comparable therapeutic effect as two or more doses of a reference antibody.

In some embodiments, an anti-BCMA antibody or fragment thereof, described herein is administered at a dose that is about 90%, 80%, 70%, 60%, 50%, 40%, 30%, 20%, 10%, or 5% of the concentration of a target antigen (e.g., BCMA) in the subject.

In some embodiments, an anti-BCMA antibody or fragment thereof described herein can be physical introduced to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, including a topical, epidermal or mucosal route of administration, for example, intranasally, vaginally, rectally, sublingually or topically. Administering can also be performed, for example, once, a plurality of times, and/or over one or more extended periods.

In some embodiments, an anti-BCMA antibody or fragment thereof described herein can be used in a number of diagnostic and therapeutic applications. For example, detectably-labeled versions of engineered antibodies as described herein can be used in assays to detect the presence or amount of the BCMA in a sample (e.g., a biological sample). Engineered antibodies described herein can be used in in vitro assays for studying binding to BCMA. In some embodiments, an anti-BCMA antibody described herein can be used as a positive control in an assay designed to identify additional novel compounds that are otherwise are useful for treating a BCMA-associated disorder. For example, an anti-BCMA antibody described herein can be used as a positive control in an assay to identify additional compounds (e.g., small molecules, aptamers, or antibodies) that bind to BCMA.

The antibodies or antigen-binding fragments thereof described herein may be used in monitoring a subject, e.g., a subject having, suspected of having, at risk of developing, or under treatment for one or more BCMA-associated conditions. Monitoring may include determining the amount or activity of BCMA in a subject, e.g., in the serum of a subject. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration of an anti-BCMA antibody as described herein. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a BCMA-associated disorder described herein. In an embodiment of the present invention, a chimeric antigen receptor (CAR) comprising an BCMA binding domain is disclosed for the treatment of various hematological malignancies including multiple myeloma. The BCMA protein is expressed on a cancer cell. The BCMA antigen-binding portion of the CAR interacts with an epitope within the extracellular domain of the BCMA fragment thereof.

In particular embodiments, CAR constructs, nucleic acid sequences, vectors, immune cells and so forth as contemplated herein, and/or pharmaceutical compositions comprising the same, are used for the prevention, treatment or amelioration of a disease, such as a cancerous disease. In particular embodiments, the pharmaceutical composition of the present disclosure may be particularly useful in preventing, ameliorating and/or treating cancer, including cancers that express a particular antigen and that may or may not be solid tumors, for example.

The immune cells for which the receptor is utilized may be NK cells, T cells, gamma delta T cells, alpha beta T cells, or NKT or invariant NKT (iNKT), or invariant NKT cells engineered for cell therapy for mammals, in particular embodiments. In such cases where the cells are NK cells, the NK cell therapy may be of any kind and the NK cells may be of any kind. In specific embodiments, the cells are NK cells that have been engineered to express one or more CARs and/or one or more suicide genes and/or one or more cytokines. In specific embodiments, the cells are NK cells that are transduced with a CAR.

In particular embodiments, the present disclosure contemplates, in part, CAR-expressing cells, CAR constructs, CAR nucleic acid molecules and CAR vectors that can be administered either alone or in any combination using standard vectors and/or gene delivery systems, and in at least some aspects, together with a pharmaceutically acceptable carrier or excipient. In certain embodiments, subsequent to administration, the nucleic acid molecules or vectors may be stably integrated into the genome of the subject.

In specific embodiments, viral vectors may be used that are specific for certain cells or tissues and persist in NK cells. Suitable pharmaceutical carriers and excipients are well known in the art. The compositions prepared according to the disclosure can be used for the prevention or treatment or delaying the above identified diseases.

Furthermore, the disclosure relates to a method for the prevention, treatment or amelioration of a tumorous disease comprising the step of administering to a subject in the need thereof an effective amount of cells that express a CAR, a nucleic acid sequence, a vector, as contemplated herein and/or produced by a process as contemplated herein.

Possible indications for administration of the composition(s) of the exemplary CAR cells are cancerous diseases, including tumorous diseases, including B cell malignancies, multiple myeloma, breast cancer, glioblastoma, renal cancer, pancreatic cancer, or lung cancer, for example. Exemplary indications for administration of the composition(s) of antigen-targeting CAR cells are cancerous diseases, including any malignancies that express the antigen. The administration of the composition(s) of the disclosure is useful for all stages (I, II, III, or IV) and types of cancer, including for minimal residual disease, early cancer, advanced cancer, and/or metastatic cancer and/or refractory cancer, for example.

The disclosure further encompasses co-administration protocols with other compounds, e.g. bispecific antibody constructs, targeted toxins or other compounds, which act via immune cells. The clinical regimen for co-administration of the inventive compound(s) may encompass co-administration at the same time, before or after the administration of the other component. Particular combination therapies include chemotherapy, radiation, surgery, hormone therapy, or other types of immunotherapy.

In a particular aspect, the invention provides a method of inhibiting proliferation of or reducing a population of BCMA-expressing cancer cells, the method comprising contacting a population of BCMA-expressing cancer cells with the anti-BCMA CAR-expressing cells of the invention (e.g., BCMA CAR-expressing NK cells) that bind to the BCMA-expressing cells. In one aspect, the invention provides methods for inhibiting proliferation or reducing a population of BCMA-expressing cancer cells, comprising contacting a population of BMCA-expressing cancer cells with an anti-BCMA CAR-expressing cell of the invention (e.g., a BCMA CAR-expressing NK cell) that binds to the BCMA-expressing cell. In certain aspects, an anti-BCMA CAR-expressing cell (e.g., a BCMA CAR-expressing NK cell) of the invention reduces the number, amount, or percentage of cells and/or cancer cells in a subject or animal model of myeloid leukemia or another cancer associated with a BCMA-expressing cell by at least 25%, at least 30%, at least 40%, at least 50%, at least 65%, at least 75%, at least 85%, at least 95%, or at least 99% relative to a negative control. In one aspect, the subject is a human.

In some embodiments, cancers for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

As non-limiting examples, the present anti-BCMA antibodies, CARs, cells and compositions are used for treating B cell related disease. In some embodiments, the cancer is a B-cell related disease. In some embodiments, the B-cell related disease is selected from the group consisting of plasmacytoma, Hodgkin lymphoma, follicular lymphoma, small non-cutting nuclear cell lymphoma, endemic Burkitt lymphoma, sporadic Burkitt lymphoma, marginal zone lymphoma, extranodal mucosal lymphoma Tissue lymphoma, nodular monocytic B cell lymphoma, splenic lymphoma, mantle cell lymphoma, large cell lymphoma, diffuse mixed cell lymphoma, immunoblastic lymphoma, mediastinal primary B cell lymphoma, lung B cell angiocentric lymphoma, Small lymphocytic lymphoma, B cell of unknown malignancy, lymphoma-like granulomatosis, post-transplant lymphoproliferative disorder, immunoregulatory disease, rheumatoid arthritis, myasthenia gravis, idiopathic thrombocytopenia purpura, anti Phospholipid syndrome, Chagas disease, Graves disease, Wegener's granulomatosis, polyarteritis nodosa, Sjogren's syndrome, pemphigus vulgaris, scleroderma, Multiple sclerosis, antiphospholipid syndrome, ANCA-related vasculitis, Goodpasture disease, Kawasaki disease, autoimmune hemolytic anemia, rapidly progressive glomerulonephritis, heavy chain disease, and primary or immune cell amyloidosis.

Pharmaceutical Compositions

Pharmaceutical compositions of the present disclosure comprise an effective amount of compositions comprising NK cells dispersed in a pharmaceutically acceptable carrier. In some embodiments, the composition comprises a pharmaceutically acceptable carrier, diluent, solubilizer, emulsifier, preservative and/or adjuvant. In some embodiments, the composition comprises an excipient. The preparation of a pharmaceutical composition that comprises the compositions will be known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The pharmaceutical compositions may comprise different types of carriers depending on whether it is to be administered in solid, liquid or aerosol form, and whether it need to be sterile for such routes of administration as injection. The presently disclosed compositions can be administered intravenously, intradermally, transdermally, intrathecally, intraarterially, endoscopically, intraperitoneally, intranasally, intravaginally, intrarectally, topically, intramuscularly, percutaneously, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), regionally by perfusion, in a tumor microenvironment, or by other method or any combination of the forgoing as would be known to one of ordinary skill in the art (see, for example, Remington's Pharmaceutical Sciences, 18th Ed. Mack Printing Company, 1990, incorporated herein by reference).

Formulations and Administration

In various embodiments, antibodies or antigen-binding fragments thereof described herein (e.g., an anti-BCMA antibody described herein) can be incorporated into a pharmaceutical composition. Such a pharmaceutical composition can be useful, e.g., for the prevention and/or treatment of diseases, e.g., a BCMA-associated disorder. Pharmaceutical compositions can be formulated by methods known to those skilled in the art (such as described in *Remington's Pharmaceutical Sciences,* 17th edition, ed. Alfonso R. Gennaro, Mack Publishing Company, Easton, Pa. (1985)).

A suitable means of administration can be selected based on the age and condition of a subject. A single dose of the pharmaceutical composition containing an antibody or fragment thereof described herein (e.g., an anti-BCMA antibody described herein) can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

In various embodiments, a pharmaceutical composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present invention can include a pharmaceutically acceptable salt, e.g., an acid addition salt or a base addition salt.

In various embodiments, a composition including an antibody as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

As disclosed herein, a pharmaceutical composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

In various embodiments, a pharmaceutical composition of the present invention can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

A pharmaceutical composition can be administered parenterally in the form of an injectable formulation comprising a sterile solution or suspension in water or another pharmaceutically acceptable liquid. For example, the pharmaceutical composition can be formulated by suitably combining therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided. Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

In some embodiments, a composition can be cryoformulated for storage at a temperature below 0° C. (e.g., −20° C. or −80° C.). The cryopreserved cells were thawed and injected to the subject. As a media that used for cryoformulation, following cryopreservation media are exemplified;

| Cryopreservation Media | Composition |
| --- | --- |
| 1 | 50% PLASMA-LYTE-HEPES + 35% Dextran/Dextrose + 10% HSA + 5% DMSO |
| 2 | 40% PLASMA-LYTE A + 50% CS10 + 10% HSA |
| 3 | 50% MEM-HEPEs + 35% Dextran/Dextrose + 10% HSA + 5% DMSO |
| 4 | 40% MEM + 50% CS10 + 10% HSA |
| 5 | 38.6% PLASMA-LYTE A + 50% CS10 + 10% HSA + 0.8% AA + Vitamin (0.2% vial 1 and 0.4% vials 2) + 30 mM trehalose |
| 6 | 40% MEM + 50% CS10 + 10% HSA + 1.5 mM Glutathione |
| 7 | 40% PLASMA-LYTE A + 50% CS10 + 10% HSA + 1.5 mM Glutathione |
| 8 | 38.6% PLASMA-LYTE A + 50% CS10 + 10% HSA + 0.8% AA + 0.6% Vitamin + 1.5 mM Glutathione |
| 9 | 40% PLASMA-LYTE A + 50% CS10 + 10% HSA + 30 mM trehalose |

Each component used for cryoformulation can be obtained from any commercially available sources. As a non-limiting example, each component mentioned above can be obtained from following vendor:

| Components | Vendor |
| --- | --- |
| PLASMA-LYTE A | Baxter |
| MEM | Thermo Fisher |
| 25% HAS | Shire |
| Glutathione | Sigma Aldrich |
| Amino acid solution | Baxter |
| DMSO | Origen Biomedical |
| Vitamin solution | Baxter |
| CryoStor® CS10 | BioLife Solutions |
| Trehalose | J. T. Baker |

In some embodiments, the composition can be formulated for storage for up to 2 years (e.g., one month, two months, three months, four months, five months, six months, seven months, eight months, nine months, 10 months, 11 months, 1 year, 1.5 years, or 2 years) at 2-8° C. (e.g., 4° C.). Thus, in some embodiments, the compositions described herein are stable in storage for at least 1 year at 2-8° C. (e.g., 4° C.).

In particular instances, a pharmaceutical composition can be formulated as a solution. In some embodiments, a composition can be formulated, for example, as a buffered solution at a suitable concentration and suitable for storage at 2-8° C. (e.g., 4° C.).

Compositions including one or more engineered antibodies as described herein can be formulated in immunoliposome compositions. Such formulations can be prepared by methods known in the art. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "*Sustained and Controlled Release Drug Delivery Systems,*" Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art. Dry powder inhaler formulations and suitable systems for administration of the formulations are also known in the art. Pulmonary administration may be oral and/or nasal. Examples of pharmaceutical devices for pulmonary delivery include metered dose inhalers, dry powder inhalers (DPIs), and nebulizers. For example, a composition described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TURBO-HALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition described herein can be intrapulmonarily administered by way of a metered dose inhaler. These inhalers rely on a propellant to deliver a discrete dose of a compound to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, compositions can be formulated for delivery to the eye, e.g., in the form of a pharmaceutically acceptable solution, suspension or ointment. A preparation for use in treating an eye can be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents. A preparation as described herein can be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreal cavity of the eye may be appropriate, in certain embodiments, for administration of a composition as described herein. For example, U.S. Publication No. 2002/0026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a trans scleral patch and delivery via contact lenses) for delivery of a therapeutic agent to the eye are described in, e.g., Ambati and Adamis (2002) *Prog Retin Eye Res* 21 (2): 145-151; Ranta and Urtti (2006) *Adv Drug Delivery Rev* 58 (11): 1164-1181; Barocas and Balachandran (2008) *Expert Opin Drug Delivery* 5 (1):

1-10 (10); Gulsen and Chauhan (2004) *Invest Opthalmol Vis Sci* 45:2342-2347; Kim et al. (2007) *Ophthalmic Res* 39:244-254; and PCT publication no. WO 04/073551, the disclosures of which are incorporated herein by reference in their entirety.

In certain embodiments, administration of an antibody as described herein is achieved by administering to a subject a nucleic acid encoding the antibody. Nucleic acids encoding a therapeutic antibody described herein can be incorporated into a gene construct to be used as a part of a gene therapy protocol to deliver nucleic acids that can be used to express and produce antibody within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407). Examples of suitable retroviruses include pLJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc Natl Acad Sci USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) Human Gene Therapy 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; and PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992) *Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and McLaughlin et al. (1989) *J Virol* 62:1963-1973.

In various embodiments, subcutaneous administration can be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with antibody drug for subcutaneous injection.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering solution to a subject with as little pain as possible. One medication delivery pen includes a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits include one or more disposable replacement needles. Pen devices suitable for delivery of any one of the presently featured compositions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition described herein can be therapeutically delivered to a subject by way of local administration. As used herein, "local administration" or "local delivery," can refer to delivery that does not rely upon transport of the composition or agent to its intended target tissue or site via the vascular system. For example, the composition may be delivered by injection or implantation of the composition or agent or by injection or implantation of a device containing the composition or agent. In certain embodiments, following local administration in the vicinity of a target tissue or site, the composition or agent, or one or more components thereof, may diffuse to an intended target tissue or site that is not the site of administration.

In some embodiments, the compositions provided herein are present in unit dosage form, which unit dosage form can be suitable for self-administration. Such a unit dosage form may be provided within a container, typically, for example, a vial, cartridge, prefilled syringe or disposable pen. A doser such as the doser device described in U.S. Pat. No. 6,302,855, may also be used, for example, with an injection system as described herein.

A suitable dose of a composition described herein, which dose is capable of treating or preventing a disorder in a subject, can depend on a variety of factors including, e.g., the age, sex, and weight of a subject to be treated and the particular inhibitor compound used. For example, a different dose of one composition including an antibody as described herein may be required to treat a subject with a BCMA-associated disorder as compared to the dose of a different formulation of that antibody. Other factors affecting the dose administered to the subject include, e.g., the type or severity of the disorder. For example, a subject having one BCMA-associated disorder may require administration of a different dosage than a subject with another BCMA-associated disorder. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject may also be adjusted based upon the judgment of the treating medical practitioner.

In some embodiments, a composition described herein is administered as a fixed dose, or in a milligram per kilogram (mg/kg) dose. In some embodiments, the dose is chosen to reduce or avoid production of antibodies or other host immune responses against one or more of the antibody or an antigen-binding fragment thereof in the composition. While in no way intended to be limiting, exemplary dosages of an antibody, such as a composition described herein include, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition described herein include, without limitation, 0.1 mg/kg, 0.5 mg/kg, 1.0 mg/kg, 2.0 mg/kg, 4 mg/kg, 8 mg/kg, or 20 mg/kg.

In some embodiments, the composition is administered at a dosage and administration interval sufficient to reduce or treat one or more symptoms of a disease associated with aberrant BCMA expression. In some embodiments, the composition is administered every day, twice a day, one per week, twice per week, thrice per week, once every two weeks, once per month, once every 2 months, once every 6 months, or once per year. In some embodiments, treatment comprises a single administration of the antibody.

In some embodiments, the composition is a pharmaceutical composition comprising one or more excipients.

A pharmaceutical solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount of a composition described herein can also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the a BCMA-associated disorder. For example, a therapeutically effective amount of a composition described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by therapeutically beneficial effects.

Suitable human doses of any of the compositions described herein can further be evaluated in, e.g., Phase I dose escalation studies. See, e.g., van Gurp et al. (2008) *Am J Transplantation* 8 (8): 1711-1718; Hanouska et al. (2007) *Clin Cancer Res* 13 (2, part 1): 523-531; and Hetherington et al. (2006) *Antimicrobial Agents and Chemotherapy* 50 (10): 3499-3500.

Toxicity and therapeutic efficacy of compositions can be determined by known pharmaceutical procedures in cell cultures or experimental animals (e.g., animal models of any of the BCMA-associated disorders). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is therapeutic index and it can be expressed as the ratio $LD_{50}/ED_{50}$. A composition described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

Those of skill in the art will appreciate that data obtained from cell culture assays and animal studies can be used in formulating a range of dosage for use in humans. Appropriate dosages of compositions described herein lie generally within a range of circulating concentrations of the compositions that include the $ED_{50}$ with little or no toxicity. The dosage may vary within this range depending upon the dosage form employed and the route of administration utilized. For a composition described herein, therapeutically effective dose can be estimated initially from cell culture assays. A dose can be formulated in animal models to achieve a circulating plasma concentration range that includes the $I_0$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modelling can be used to determine a dose required to achieve a therapeutically effective concentration within the local site.

Combination Therapies

According to the present disclosure, antibodies, antigen binding fragments, CARs, vectors and cells expressing CAR and compositions described herein can be used in combination with other therapies for cancer treatment.

In various embodiments, an anti-BCMA antibody as described herein may be included in a course of treatment that further includes administration of at least one additional agent to a subject. In various embodiments, an additional agent administered in combination with an anti-BCMA antibody as described herein may be a chemotherapy agent.

In some embodiments, the anti-BCMA antibodies, fragments thereof can be conjugated (e.g., linked to) to a therapeutic agent (e.g., a chemotherapeutic agent and a radioactive atom) for binding to a cancer cell, delivering therapeutic agent to the cancer cell, and killing the cancer cell which expresses human BCMA. In some embodiments, an anti-BCMA antibody is linked to a therapeutic agent. In some embodiments, therapeutic agent is a chemotherapeutic agent, a cytokine, a radioactive atom, an siRNA, or a toxin. In some embodiments, therapeutic agent is a chemotherapeutic agent. In some embodiments, the agent is a radioactive atom.

In some embodiments, the methods can be performed in conjunction with other therapies for BCMA-associated disorders. For example, the composition can be administered to a subject at the same time, prior to, or after, chemotherapy. In some embodiments, the composition can be administered to a subject at the same time, prior to, or after, an adoptive therapy method.

In various embodiments, an additional agent administered in combination with an anti-BCMA antibody as described herein may be administered at the same time as an anti-BCMA antibody, on the same day as an anti-BCMA antibody, or in the same week as an anti-BCMA antibody. In various embodiments, an additional agent administered in combination with an anti-BCMA antibody as described herein may be administered in a single formulation with an anti-BCMA antibody. In certain embodiments, an additional agent administered in a manner temporally separated from administration of an anti-BCMA antibody as described herein, e.g., one or more hours before or after, one or more days before or after, one or more weeks before or after, or one or more months before or after administration of an anti-BCMA antibody. In various embodiments, the administration frequency of one or more additional agents may be the same as, similar to, or different from the administration frequency of an anti-BCMA antibody as described herein.

Encompassed within combination therapy is the a treatment regimen that includes administration of two distinct antibodies as described herein and/or a treatment regimen that includes administration of an antibody as described herein by a plurality of formulations and/or routes of administration.

In some embodiments, compositions can be formulated with one or more additional therapeutic agents, e.g., additional therapies for treating or preventing a BCMA-associated disorder (e.g., a cancer or autoimmune disorder) in a subject. Additional agents for treating a BCMA-associated disorder in a subject will vary depending on the particular disorder being treated, but can include, without limitation, rituximab, cyclophosphamide, doxorubicin, vincristine, prednisone, osfamide, carboplatin, etoposide, dexamethasone, cytarabine, cisplatin, cyclophosphamide, or fludarabine.

A composition described herein can replace or augment a previously or currently administered therapy. For example, upon treating with a composition described herein, administration of the one or more additional active agents can cease or diminish, e.g., be administered at lower levels, e.g., lower levels of a reference antibody that cross-competes for BCMA binding) following administration of an anti-BCMA antibody described herein. In some embodiments, administration of the previous therapy can be maintained. In some embodiments, a previous therapy will be maintained until the level of the composition reaches a level sufficient to provide a therapeutic effect. The two therapies can be administered in combination.

In certain embodiments, the compositions and methods of the present embodiments involve an immune cell population (including NK cell population) in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, hormone therapy, oncolytic viruses, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

In particular embodiments, in addition to the inventive cell therapy of the disclosure, the individual may have been provided, may be provided, and/or will be provided a specific additional therapy for cancer, including one or more of surgery, radiation, immunotherapy (other than the cell therapy of the present disclosure), hormone therapy, gene therapy, chemotherapy, and so forth.

An immune cell therapy may be administered before, during, after, or in various combinations relative to an additional cancer therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an immune cell therapy is "A" and an anti-cancer therapy is "B": A/B/A B/A/B B/B/A A/A/B A/B/B B/A/A A/B/B/B B/A/B/B B/B/B/A B/B/A/B A/A/B/B A/B/A/B A/B/B/A B/B/A/A B/A/B/A B/A/A/B A/A/A/B B/A/A/A A/B/A/A A/A/B/A Administration of any compound or cell therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gamma 1I and calicheamicin omega 11); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKDolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carbolplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis*, *Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., costimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, Nat Rev Cancer, 12 (4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell costimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, an art-recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95 (17): 10067-10071; Camacho et al. (2004) J Clin Oncology 22 (145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. U.S. Pat. Nos. 5,844,905, 5,885,796 and International Patent Application Nos. WO1995001994 and WO1998042752; all incorporated herein by reference, and immunoadhesins such as described in U.S. Patent No. U.S. Pat. No. 8,329,867, incorporated herein by reference.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Recombinant Gene Technology

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); *Nucleic Acid Hybridization* (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), *Current Protocols in Molecular Biology*, John Wiley & Sons, Inc. (1994).

Recombinant expression of a gene, such as a nucleic acid encoding a polypeptide, such as an anti-BCMA antibody described herein, can include construction of an expression vector containing a nucleic acid that encodes the polypeptide. In some embodiments, the BCMA nucleic acid sequences may be codon optimized sequences for mammalian cell expression. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques to produce polypeptides. All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

F. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signalling by elevating the number of GAP junctions would increase the anti-hyperproliferative effects on the neighbouring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

Kits of the Disclosure

Any of the compositions described herein may be comprised in a kit. In a non-limiting example, cells, reagents to produce cells, vectors, and reagents to produce vectors and/or components thereof may be comprised in a kit. In certain embodiments, NK cells may be comprised in a kit, and they may or may not yet express a BCMA-CAR comprising (a) CD28 hinge, an optional cytokine, or an optional suicide gene. Such a kit may or may not have one or more reagents for manipulation of cells. Such reagents include small molecules, proteins, nucleic acids, antibodies, buffers, primers, nucleotides, salts, and/or a combination thereof, for example. Nucleotides that encode one or more CARs, suicide gene products, and/or cytokines may be included in the kit. Proteins, such as cytokines or antibodies, including monoclonal antibodies, may be included in the kit. Nucleotides that encode components of engineered CAR receptors may be included in the kit, including reagents to generate same.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the invention.

Example 1: Generation and Binding of Anti-BCMA Monoclonal Antibodies

The present Example demonstrates characterization of anti-BCMA antibodies. Mice (Trianni mouse harboring human transgenic heavy chain locus and kappa locus, 8-10 weeks old) were immunized according to methods described in the literature. For primary immunization, animals were hock injected with 5 µg of recombinant BCMA-Mouse Fc as an emulsion with equal volumes of GerbUMM. The mice were immunized the same way every 3-4 days for a total of 10 boosts. Animals with high antigen specific antibody titers were given a pre-fusion boost with the same immunogen four days prior to spleen and lymph node harvest for further processing for RNA extraction or hybridoma fusion.

Spleens from mice were isolated and transferred to a 50 ml tube containing 10 ml of RPMI, 10% FBS (0.2 µm filtered) and were physically disassociated to isolate lymphocytes. Lymphocytes were harvested by centrifugation at 1200 rpm for 10 minutes. Lymphocytes were suspended in EasySep buffer (2 ml; 0.2 µm filtered).

Anti-BCMA scFv were identified by generation and selection of an immunized scFv phage display library. First, total RNA was purified from single-cell suspension of splenocytes from one individual mouse previously immunized with BCMA expressing CHO cells. From the mouse a scFv library was then generated by random-primed cDNA using total RNA as a template to amplify variable regions from mouse antibody genes. Heavy and kappa chain amplicons were combined and cloned into phagemid vectors. Three rounds of selection were performed against recombinant BCMA proteins (human BCMA-Fc, human BCMA-6His) and/or cells expressing cynomolgus BCMA to identify BCMA-specific scFv phage clones. Periplasmic extracts of selected scFv clones were then screened by ELISA or flow cytometry. Clones were selected for sequencing and binding was confirmed by Octet using periplasmic extract. In total, 19 clones were identified through the phage display. In addition to the 19 clones, other 42 newly identified clones of BCMA antibodies were applied to the antibody selection. Table 2 shows the binding affinities of human BCMA scFv to human BCMA.

Octet Analysis

An Octet binding analysis was performed to evaluate the kinetics of binding with BCMA.

An Octet binding assay was performed using human BCMA protein with a panel of anti-BCMA clones for binding characterization. Human BCMA was first captured onto the appropriately coated Octet sensor tips, then positioned into wells containing the anti-BCMA clones for association. After the sensor tip was placed in the dissociation wells, the response of the interaction was calculated for each anti-BCMA clone and corresponding human BCMA protein.

FACS Analysis

Anti-BCMA clones were tested for on-cell binding by FACS using BCMA overexpressing CHO cells. Cells were incubated with anti-BCMA clones and subsequently with a secondary antibody capable of binding to the anti-BCMA clones. These samples were washed appropriately and assessed on the Attune NxT Flow Cytometer (Thermo Fisher Scientific). FACS analysis was performed in FlowJo.

Table 3 shows the results of Octet and FACS analyses of exemplary anti-BCMA clones on exemplary anti-BCMA antibodies and human BCMA. It was observed that exemplary Fab (IgG) had high $k_{on}$ rates and low $k_{off}$ rates, with $K_D$ values in low pico-molar range.

TABLE 3

Octet Analysis of scFv generated by phage display from periplasmic extract.

| PE ELISA Bio- huBCMA-His | PE ELISA Bio- cyBCMA-His | PE FACS% Binding Hu BCMA | PE Octet $K_{off}$ | VH sequence HCDR sequences bolded | VL sequence LCDR sequences bolded |
|---|---|---|---|---|---|
| 1.104 | 0.147 | 89.01 | 3.69E-04 | QITLRESGGDVVQ PGRSLRLSCAASG FTFSSYAIHWVRQ APGKGLEWVAVT WHDGSNKYYAES VMGRFTISRDNSK NTLYLHMNSLRAE DTGVYYCARAKF GEPQYFQHWGQG TLVTVSS (SEQ ID NO: 88) | DIVMTQSPSFLSASVG DRVTITCRASQGISSY LAWYQQKPGKAPKLL IYAASTLQSGVPSRFS GSGSGTEFTLTISSLQP EDFATYYCQQLNSYP WTFGQGTKVDIK (SEQ ID NO: 89) |
| 1.112 | 0.122 | 54.65 | 4.40E-04 | QITLRESGGDVVQ PGRSLRLSCAASG FTFSSYAIHWVRQ APGKGLEWVAVT WHDGSNKYYAES VMGRFTISRDNSK NTL YLHMNSLRAE DTGVYYCARAKF GEPQYFQHWGQG TLVTVSS (SEQ ID NO: 88) | DIVMTQSPSFLSASVG DRVTITCRASQGINNY LAWYQQKPGIAPKLLI YAASTLQSGVPSRFGG SGSGTEFTLTISSLQPE DFATYYCQQLKSYPF TFGPGTKVEIK (SEQ ID NO: 90) |
| 0.516 | 0.126 | 47.16 | 4.39E-04 | EVQLVESGGDVV QPGRSLRLSCAAS GFTFSSYAIHWVR QAPGKGLEWVAV TWHDGSNKYYAE SVMGRFTISRDNS KNTLYLHMNSLR AEDTGVYYCARA KFGEPQYFQHW QGTTVTVSS (SEQ ID NO: 91) | DIVMTQSPSFLSASVG DRVTITCRASQGISSY LAWYQQKPGKAPKLL IYAASTLQSGVPSRFS GSGSGTEFTLTISSLQP EDFATYYCQQLNSYP FTFGPGTKVDIK (SEQ ID NO: 92) |

TABLE 4

Octet and FACS Analysis of 2 Lead Anti-BCMA Clones.

| | hBCMA-mIgG2a | | | | hBCMA-HIS antigen | | | | hBCMA CHO |
|---|---|---|---|---|---|---|---|---|---|
| Sample | Response | $K_D$ (M) | $k_{on}$(1/Ms) | $k_{dis}$(1/s) | Response | $K_D$ (M) | $k_{on}$(1/Ms) | $k_{dis}$(1/s) | EC50 µg/ml |
| VH: SEQ ID NO: 26, VL: SEQ ID NO: 25 Ab 2 | 0.62 | 1.17E−11 | 3.79E+05 | 4.44E−06 | 1.296 | 7.88E−11 | 4.79E+05 | 3.77E−05 | 0.144 |
| VH: SEQ ID NO: 10, VL: SEQ ID NO: 27 Ab 3 | 0.5813 | <1.0E−12 | 3.08E+05 | <1.0E−07 | 1.3007 | 6.08E−11 | 2.19E+05 | 1.33E−05 | 0.1167 |

Example 2: Constructs of Chimeric Antigen Receptors

This Example shows exemplary CAR constructs for reducing tumor burden. FIG. 1 shows CAR constructs comprising BCMA binder region.

The BCMA CAR comprises an anti-BCMA specific binder, an IgG1 hinge or a CD28 hinge, a CD28 transmembrane domain and IL-15 cytokine (e.g., soluble IL-15). Such CAR may comprise an amino acid of SEQ ID NO: 45, SEQ ID NO: 47, or SEQ ID NO: 49.

Example 3: In Vitro Efficacy of BCMA IgG Hinge and BCMA CD28 Hinge CAR Constructs This Example shows the efficacy of BCMA CAR comprising CD28 hinge domain as SEQ ID NO 45 compared to IgG hinge domain in CB-NK cells.

The cytotoxicity of CB-NK cells was assessed in a standard four-hour 51Chromium (51Cr)-release assay. Briefly, target cells were loaded with 51Cr, washed, and co-cultured with CB-NK cells transduced with different CAR constructs bearing different BCMA specific scFv binders for 4 hours after which supernatant was removed and 51Cr levels were measured using a gamma counter.

BCMA binders were tested in a CAR backbone that contained either an IgG1 Hinge or a CD28 hinge. These CAR were then transduced into CB-NK and in vitro killing efficacy was tested with a chromium release killing assay.

All constructs exhibited higher killing than untransduced CB-NK with slightly enhanced killing demonstrated by constructs containing a CD28 hinge, particularly with lower E:T ratios, as seen in FIG. 2.

Example 4: Comparison of CD28 Hinge Domain and IgG1 Hinge Domain in Reducing Tumor Burden In Vivo This Example exemplifies the benefit of using BCMA-CAR constructs with CD28 hinge for reducing tumor burden in mice.

10 million BCMA CAR-NK cells (~70% CAR+ve), comprising BCMAIg1, BCMAIg2, BCMA28-1 or BCMA28-2, were used for this experiment. 10-12 week old female NSG mice were whole-body irradiated at 150 cGy 24 hours prior to tumor inoculation. MM.1S-ffluc-MDA cells were prepared in PBS suspension at a concentration of $2.5 \times 10^6$ cells/ml, for intravenous inoculation of cells at $0.5 \times 10^6$/animal. Bioluminescent images were taken 1 day prior to dosing, 6 days after tumor inoculation, and animals were randomized based on total flux into groups of 4 or 5 animals per arm. Animals were dosed 0, 1, or 9 days after tumor inoculation. CAR NK cells in the relevant concentrations were resuspended in PBS and transferred to the vivarium on ice in small batches to ensure timely infusion into the animals while maintaining CAR NK cell viability. Bioluminescent images were carried out weekly on a Xenogen IVIS to monitor tumor progression. Body weights were measured three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for pathology assessment.

For qPCR CK, Genomic DNA (gDNA) from mouse whole blood samples (50 µL) were extracted and purified with MagMAX™ DNA Multi-Sample Ultra 2.0 Kit in the presence of RNAse A. The purified gDNA was then analyzed with an optimized digital droplet PCR (ddPCR) based duplex assay method designed to simultaneously determine the copy numbers of CAR construct and a reference a-actin 1 (ACTA1) gene (a single copy gene in both human and mouse genome). The progression of the tumor was monitored and imaged at 7 day intervals. FIG. 3 represents the growth of the tumor in mice following treatment with cord-blood derived NK cells transduced with BCMA-CARs with IgG hinge as compared to BCMA CARs with CD28 hinge domain, relative to growth of untreated mice (tumor alone) and mice treated with untransduced NK cells (NT NK).

It was observed that mice receiving BCMA-CD28 had lower tumor burden when compared to tumor alone or NT NK. Mice receiving BCMA CD28 had superior tumor control compared to BCMA IgG within the first 2 weeks prior to succumbing to non-tumor burden related death. The lungs, liver and spleen were examined for lymphocyte infiltration. FIG. 8 shows an exemplary histopathological slide comparing the lung of a normal mouse to a lung of a mouse treated with BCMA28-2 CAR-NK cells. All tissues were fixed in 10% buffered formalin by immersion as well as tracheal instillation of the lungs. Upon complete fixation (24-48 hrs) the organs were trimmed and processed for paraffin embedding. Paraffin blocks were sectioned at 4-6 microns, and tissue sections mounted on glass slides, stained with hematoxylin and eosin (H&E), and cover-slipped.

The fluctuations in body weights are summarized in FIG. 12.

The pathology evaluation was performed by a board certified (ECVP) veterinary pathologist. Neoplastic lesions were scored according to their presence in the examined organs. Non-neoplastic lesions were scored based on their severity and distribution. The histopathologic findings were captured in Pristima® Software System.

It was observed that infiltration of lymphocytes into lung, liver and spleen was observed and believed to be causative for non-tumor burden related death, as seen in FIG. 8. However, dose reduction to 1 million and 3 million total NK cells significantly ameliorated non-tumor burden related death and enhanced survival, as seen in FIG. 4.

Example 5: Comparison of Antitumor Activity of Co-Dosed BCMA-CARs in MM1s-Tumor Mice This Example compared the anti-tumor activity of exemplary co-dosed BCMA-CAR NK cells.

1 million BCMA CAR-NK cells (~70% CAR+ve), comprising SEQ ID NO: 19, or 20 were co-dosed with MM1s tumor in mice. The progression of the tumor was monitored and imaged at 6-7 day intervals. FIG. 5 shows the pictorial depiction of survival of mice treated with 1M BCMA-NK cells comprising BCMA28-1 or BCMA28-2. It was observed that mice dosed with BCMA-CAR with BCMA28-2 performed best with greater than 50% of mice surviving at day 77 versus tumor-related death, when compared to mice co-dosed with CAR-NK cells comprising BCMA28-1.

Example 6: Delayed Dosing Regimen of BCMA-CARs-NK and BCMA-CAR-T

This Example demonstrated that BCMA28-1 worked best in comparison to other BCMA-CARs tested, however, all CAR constructs provide robust anti-tumor activity.

CAR-T-Cell Production:

For production of CAR-T, human leukapheresis products (leukopaks) were purchased from Stem cell Technologies. PBMCs were isolated from fresh leukopaks using a Ficoll density gradient. EasySep Human T cell Isolation Kit from Stemcell technologies was used to purify T cells which were then activated/expanded using T Cell TransAct beads and research grade IL-2 from Miltenyi Biotec. On Day 2 of T cell activation, cells were transduced with VSVG virus by spinoculation then used on Day 7 for in vitro assays.

CAR-NK Cell Production:

For CAR-NK production, cord blood (CB) units for research were obtained from the MD Anderson Cancer Center Cord Blood Bank. CB mononuclear cells were isolated from frozen CB units by Ficoll density gradient centrifugation. Ex vivo expansion of cord-blood derived NK cells (CB-NK cells) used uAPC stimulation on Day 0 in addition to feeding IL-2 every 2 days. On Day 6, cells were transduced with RD114 virus using spinoculation. Cells were stimulated with a second round of uAPC addition on Day 8 or 9 and fed IL-2 every 2 days until they were used for in vivo or in vitro studies on Day 15.

1 million or 3 million BCMA CAR-NK cells (~70% CAR+ve), comprising BCMA28-2 were administered to mice IV one day following MM1s tumor cell inoculation ("1-day delayed dosing")

The progression of the tumor was monitored and imaged at 7 day intervals. FIG. 6 represents the growth of the tumor in mice treated with non-transduced NK cells or NK cells transduced with BCMA-CARs with CD28 hinge domain as a function of days in 1-day delayed dose regimen. FIG. 7 shows the 1-day delayed dosing Kaplan Meier survival curve of NK cells expressing BCMA28-2. Similar experiment was repeated with a 9-day delayed dosing with a NK-cell expressing BCMA28-2 CAR. It was observed that BCMA28-2 CAR-NK cells yielded extended survival compared to tumor only or untransfected NK cells.

It was observed that a switch from co-dose to delayed dose settings (1 and 9 day delayed dose) continued to show positive anti-tumor impact of BCMA CAR-NK treatment.

Example 7: Secretion of IL-15 in BCMA-CAR-NK Cells

This Example demonstrates that the exemplary BCMA-CAR-IL-15 construct-transduced NK cells persisted in vivo, as measured by monitoring number of copies of CARs per 1000 cells and secretion of IL-15.

Bioanalysis of human IL-15 in NSG mouse plasma samples was performed using a Electrochemiluminescent Immunoassay on the Meso Scale Discovery (MSD®) platform and a U-PLEX Human IL15 assay kit (Catalog Number K151URK/(BRS 20-735), Vendor MSD). In U-PLEX® assays, biotinylated capture antibodies are first coupled to streptavidin on the U-PLEX® plate surface. The calibrators, controls, and samples are added to the plate and incubated with shaking at room temperature. Human IL-15 in calibrators, controls, and samples then bound to the capture antibodies. After washing, a solution containing detection antibodies conjugated with electrochemiluminescent labels (MSD GOLD SULFO-TAG) was added to the plate, followed by another incubation period. After incubation with the detection antibody, the plate is washed and 2× read buffer was added to the wells. The plate was read immediately in the MSD Sector Imager S600. Robust dose-dependent expansion of BCMA CAR-NK cells, expressing BCMA-CAR of SEQ ID NO: 20 and increase in IL-15 production was observed in delayed dose settings, as seen in FIG. 9.

Example 8: Use of the BCMA CAR Constructs for Improving Tumor Cell Killing Among Others in T Cell Setting This Example demonstrated the use of the BCMA CAR constructs (e.g., BCMAIg1, BCMAIg2, BCMA28-1, BCMA28-2) in tumor cell killing activity.

Cytoxicity in T cell setting was assessed utilizing Promega's CellTiter-Glow Luminescent Cell Viability Assay according the manufacturers protocol. For analysis of apoptosis and mitochondrial damage, MM.1S-ffluc-MDA target cells were labelled with CellTracker Deep Red dye from Invitrogen and the MultiCyt Apoptosis Kit from Sartorius was used to measure caspase positivity and mitochondrial damage according to the manufacturers protocol. Briefly, activation of caspase 3 and 7 is detected by the use of Nuc View 488 Caspase-3/7 substrate which fluoresces upon cleavage. Mitochondrial membrane potential was determined by the sequestration of a fluorescent small molecule inside the lumen of the intact mitochondria with an active membrane potential which upon mitochondrial depolarization leaks into the cytoplasm the cell exhibits a decrease in fluorescence. The iQue flow cytometer from Intellicyte was used to obtain flow cytometric readouts.

The BCMA CAR constructs (e.g., BCMAIg1, BCMAIg2, BCMA28-1, BCMA28-2) were tested in the same CAR backbone in human primary T cells against the BCMA positive cell line MM.1S-ffluc-MDA.

All of the BCMA CAR constructs demonstrated killing above that of CD19 CAR expressing T cells (negative control). Additionally, constructs utilizing the CD28 hinge showed enhanced levels of cytotoxicity, apoptosis, and mitochondrial damage when compared the same binder in a CAR backbone containing an IgG1 hinge. The specific killing of tumor cells, based on 3 different assay readouts, are seen in FIG. 10 (A-C).

Example 9: Analysis of Apoptosis in Transfected CAR-NK Cells

This Experiment, was designed to analyze apoptosis in CAR-NK transduced with BCMA28-1 or BCMA28-2 in the presence or absence of soluble BCMA.

For analysis of apoptosis, MM.1S-ffluc-MDA target cells were labelled with CellTracker Deep Red dye from Invitrogen and the MultiCyt Apoptosis Kit from Sartorius was used to measure caspase positivity according to the manufacturers' protocol. Effector cells were coculture with target cells in the presence or absence of 800 ng/ml soluble recombinant BCMA obtained from ACRO Biosciences. Briefly, activation of caspase 3 and 7 is detected by the use of Nuc View 488 Caspase-3/7 substrate which fluoresces upon cleavage. The iQue flow cytometer from Intellicyte was used to obtain flow cytometric readouts.

It was observed that CAR-NK induced lower levels of apoptosis in the target cells in the presence of 800 ng/mL soluble BCMA, particularly at high E:T ratios, as seen in FIG. 11.

Example 10: In Vivo Efficacy of BCMA CAR Constructs Against MM1S Tumor

This Example shows the efficacy of BCMA28-2 containing CAR expressed in CB-NK cells, against MM1S tumor.

10-12 week old female NSG mice were whole-body irradiated at 150 cGy 24 hours prior to tumor inoculation. MM. 1S-ffluc-MDA cells were prepared in PBS suspension at a concentration of $2.5 \times 10^6$ cells/ml, for intravenous inoculation of cells at $0.5 \times 10^6$/animal. Bioluminescent images were taken 1 day prior to dosing, 6 days after tumor inoculation, and animals were randomized based on total flux into groups of 4 animals per arm. Animals were dosed 7 days after tumor inoculation. The CAR expressing NK (i.e., CAR NK) cells, that had been cryopreserved in the cryoformulation (e.g., 38.6% PLASMA-LYTE A+50% CS10+10% HSA+0.8% AA+ Vitamin+30 mM trehalose), were thawed and directly injected with PBS buffer to the mice without washing. Bioluminescent images were carried out weekly on a Xenogen IVIS to monitor tumor progression. Body weights were taken three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis. At humane or study endpoint, necropsy of animals from studies of interest was carried out to obtain various tissues for tox/pathology assessment.

All CAR transduced NK cells showed a survival benefit when compared to tumor alone (FIG. 13).

CAR-NK Cell Manufacturing

For CAR-NK production, cord blood (CB) units for research were obtained from the MD Anderson Cancer Center Cord Blood Bank. CB mononuclear cells were isolated from frozen CB units by Ficoll density gradient centrifugation. Ex vivo expansion of cord-blood derived NK cells (CB-NK cells) used uAPC stimulation on Day 0 in addition to feeding IL-2 every 2 days. On Day 6, cells were transduced with RD114 virus using spinoculation. Cells were stimulated with a second round of uAPC addition on Day 8 or 9 and fed IL-2 every 2 days until they were used for in vivo or in vitro studies on Day 15 or cryopreserved on Day 21 for later use.

Example 11: In Vitro Efficacy of BCMA CAR Constructs Against Multiple Tumor Lines This Example shows the efficacy of BCMA28-2 CAR expressed in CB-NK cells against different tumor cells.

MM1S-Luc, RPMI-8226-Luc, JJN3-Luc and JJN3-Luc BCMA KO cells were washed with PBS once, cells were incubated with cell tracer deep red dye (Invitrogen #C34565) at 1:10,000 dilution in PBS at 37° C. for 20 minutes with the cell density at 2.5 million/ml. At the end of incubation, 20 ml cell culture medium were added to the cells and cells were spun down at 500 g for 5 minutes, supernatant was removed and cells were washed one more time using corresponding cell culture medium. Cells were then re-suspended in culture medium at 0.25 million/ml, and 30μul cells were added to each well of the v-bottom 384 well assay plates (Greiner, Catalog: 781280). Cells were incubated at 37° C. cell culture incubator with 5% $CO_2$ for 1-2 hours. Fresh effector cells were harvested at day 15 and cells were washed once in the cytokine free NK cell medium (CellGenix GMP SCGM with 10% HI-FBS and 2 mM Glutamine), 10 μl effector cells were then added to the assay plates at different E:T ratios. Target cells and effector wells were co-cultured for 20 hours, cells were then spun down and supernatant was collected for cytokine release assay. Cells were incubated with 10 μl caspase3/7 reagent (Intellicyt, catalog: 91035) diluted at 1:500 in corresponding target cell medium for 1 hour in cell culture incubator at 37° C. and then submitted for FACS analysis using either Sartorius iQue3 or Sartorius iQue screener Plus. The percentage of target cells with positive caspase 3/7 staining was used to report the cytotoxicity of effector cells.

In vitro killing activity was demonstrated by different CBU donor-derived BCMA28-2 CAR construct-containing NK cells against multiple tumor cell lines (as shown in FIGS. 14A-D).

Example 12. Ability of BCMA CAR NK Cells to Kill Tumor Cells In Vitro with Multiple Rounds of Restimulation This Example shows the efficacy of BCMA28-2 CAR expressed in CB-NK cells.

Effector cells were harvested and resuspended in SCGM (CellGenix, catalogue no.: 20802-0500) supplemented with 10% Heat Inactivated FBS (Sigma, catalogue no.: F4135-500 mL), 1% L-Glutamine (Gibco, catalogue no.: 25030-081), 1% Penn Strep (Gibco, catalogue no.: 15140-122) and 100 IU/mL Human IL-2 (Miltenyi, catalogue no.: 130-097-748). Effector cells were seeded in triplicate into a 48 well flat bottom non-tissue culture treated plate (Corning, catalogue no.: 3548) at a density of 2e5 cells/well (MM1S model). Target cells previously transduced with NucLight Red Lentivirus (Sartorius, catalogue no.: 4476) and selected with 1 μg/mL puromycin (Sigma, catalogue no.: P8833-10 MG) were harvested and resuspended in the complete media described above and seeded at a density of 5e4 cells/well. Plates were placed in an IncuCyte S3 (Sartorius Inc.) and quadruplicate readings per well were measured in both the bright field and red channel using the 10× objective every 30 minutes. Target cells were prepared as described above and reseeded at a density of 5e4 cells/well every 48-72 hours (MM1S model,) for a total of 9 tumor stimulations/rechallenges. Target cell cytolysis is represented as mean red object count per image (FIG. 15A) and total average area under the curve of the red object count (FIG. 15B).

Example 13: In Vivo Efficacy of BCMA CAR Constructs Against RPMI-8226 Tumor 10-12 week old female NSG mice were whole-body irradiated at 150 cGy 24 hours prior to tumor inoculation. RPMI-8226-luc cells were prepared in PBS suspension at a concentration of $2.5 \times 10^6$ cells/ml, for intravenous inoculation of cells at $0.5 \times 10^6$/animal. Bioluminescent images were taken 1 day prior to dosing, 6 days after tumor inoculation, and animals were randomized based on total flux into groups of 4 animals per arm. Animals were dosed 7 days after tumor inoculation. The CAR expressing NK cells in the relevant concentrations were resuspended in PBS and transferred to the vivarium on ice in small batches to ensure timely infusion into the animals while maintaining the CAR expressing NK cell viability. Bioluminescent images were carried out weekly on a Xenogen IVIS to monitor tumor progression. Body weights were taken three times a week, alongside clinical observations to monitor for any signs of toxicity. Microsampling (via submandibular collection of blood) was carried out once a week for cellular kinetics analysis to quantify CAR NK expansion in vivo, either by ddPCR or flow cytometric analysis.

BCMA28-2 (with CD28 costimulatory domain)-CAR NK treated groups demonstrated anti-tumor activity, compared to UTD NK (FIG. 16).

The invention claimed is:

1. An anti-B-cell maturation antigen (anti-BCMA) antibody or antigen binding fragment thereof, comprising
heavy chain complementarity determining region (CDR) sequences comprising SEQ ID NOs: 2, 3 and 4, and
   (a) light chain CDR sequences comprising SEQ ID NOs: 6, 7 and 8; or
   (b) light chain CDR sequences comprising SEQ ID NOs: 11, 7 and 14; or
   (c) light chain CDR sequences comprising SEQ ID NOs: 11, 7 and 12.

2. The anti-BCMA antibody or antigen binding fragment thereof of claim 1, comprising heavy chain CDR sequences SEQ ID NOs: 2, 3 and 4, and light chain CDR sequences SEQ ID NOs: 6, 7 and 8.

3. The anti-BCMA antibody or antigen binding fragment thereof of claim 1, wherein the anti-BCMA antibody or antigen binding fragment thereof comprises a variable heavy (VH) chain having at least 85% identity to the amino acid sequence of SEQ ID NO: 1 or 9 and a variable light (VL) chain having at least 85% identity to the amino acid sequence of SEQ ID NO: 5, 10 or 13.

4. The anti-BCMA antibody or antigen binding fragment thereof of claim 1, wherein the anti-BCMA antibody or antigen binding fragment thereof comprises a variable heavy (VH) chain having the amino acid sequence of SEQ ID NO: 1 or 9 and a variable light (VL) chain having the amino acid sequence of SEQ ID NO: 5, 10 or 13.

5. The anti-BCMA antibody or antigen binding fragment thereof of claim 1, wherein the anti-BCMA antibody or antigen binding fragment thereof comprises a linker selected from SEQ ID NOs: 15-18.

6. The anti-BCMA antibody or antigen binding fragment thereof of claim 1, wherein the anti-BCMA antibody or antigen binding fragment thereof comprises a scFv of SEQ ID NO: 85, 86 or 87.

* * * * *

```
                            SEQUENCE LISTING

Sequence total quantity: 92
SEQ ID NO: 1            moltype = AA  length = 120
FEATURE                 Location/Qualifiers
source                  1..120
                        mol_type = protein
                        organism = synthetic construct
SEQUENCE: 1
QITLRESGGD VVQPGRSLRL SCAASGFTFS SYAIHWVRQA PGKGLEWVAV TWHDGSNKYY   60
AESVMGRFTI SRDNSKNTLY LHMNSLRAED TGVYYCARAK FGEPQYFQHW GQGTLVTVSS  120

SEQ ID NO: 2            moltype = AA  length = 5
FEATURE                 Location/Qualifiers
source                  1..5
                        mol_type = protein
                        organism = synthetic construct
SEQUENCE: 2
SYAIH                                                                5

SEQ ID NO: 3            moltype = AA  length = 17
FEATURE                 Location/Qualifiers
source                  1..17
                        mol_type = protein
                        organism = synthetic construct
SEQUENCE: 3
VTWHDGSNKY YAESVMG                                                  17

SEQ ID NO: 4            moltype = AA  length = 11
FEATURE                 Location/Qualifiers
source                  1..11
                        mol_type = protein
                        organism = synthetic construct
SEQUENCE: 4
AKFGEPQYFQ H                                                        11

SEQ ID NO: 5            moltype = AA  length = 107
FEATURE                 Location/Qualifiers
source                  1..107
                        mol_type = protein
                        organism = synthetic construct
SEQUENCE: 5
DIVMTQSPSF LSASVGDRVT ITCRASQGIN NYLAWYQQKP GIAPKLLIYA ASTLQSGVPS   60
RFGGSGSGTE FTLTISSLQP EDFATYYCQQ LKSYPFTFGP GTKVEIK                107

SEQ ID NO: 6            moltype = AA  length = 11
FEATURE                 Location/Qualifiers
source                  1..11
                        mol_type = protein
                        organism = synthetic construct
SEQUENCE: 6
RASQGINNYL A                                                        11

SEQ ID NO: 7            moltype = AA  length = 7
FEATURE                 Location/Qualifiers
source                  1..7
                        mol_type = protein
                        organism = synthetic construct
```

```
SEQUENCE: 7
AASTLQS                                                                        7

SEQ ID NO: 8            moltype = AA   length = 9
FEATURE                 Location/Qualifiers
source                  1..9
                        mol_type = protein
                        organism = synthetic construct
SEQUENCE: 8
QQLKSYPFT                                                                      9

SEQ ID NO: 9            moltype = AA   length = 120
FEATURE                 Location/Qualifiers
source                  1..120
                        mol_type = protein
                        organism = synthetic construct
SEQUENCE: 9
EVQLVESGGD VVQPGRSLRL SCAASGFTFS SYAIHWVRQA PGKGLEWVAV TWHDGSNKYY               60
AESVMGRFTI SRDNSKNTLY LHMNSLRAED TGVYYCARAK FGEPQYFQHW GQGTTVTVSS              120

SEQ ID NO: 10           moltype = AA   length = 107
FEATURE                 Location/Qualifiers
source                  1..107
                        mol_type = protein
                        organism = synthetic construct
SEQUENCE: 10
DIVMTQSPSF LSASVGDRVT ITCRASQGIS SYLAWYQQKP GKAPKLLIYA ASTLQSGVPS               60
RFSGSGSGTE FTLTISSLQP EDFATYYCQQ LNSYPFTFGP GTKVDIK                            107

SEQ ID NO: 11           moltype = AA   length = 11
FEATURE                 Location/Qualifiers
source                  1..11
                        mol_type = protein
                        organism = synthetic construct
SEQUENCE: 11
RASQGISSYL A                                                                   11

SEQ ID NO: 12           moltype = AA   length = 9
FEATURE                 Location/Qualifiers
source                  1..9
                        mol_type = protein
                        organism = synthetic construct
SEQUENCE: 12
QQLNSYPFT                                                                      9

SEQ ID NO: 13           moltype = AA   length = 107
FEATURE                 Location/Qualifiers
source                  1..107
                        mol_type = protein
                        organism = synthetic construct
SEQUENCE: 13
DIVMTQSPSF LSASVGDRVT ITCRASQGIS SYLAWYQQKP GKAPKLLIYA ASTLQSGVPS               60
RFSGSGSGTE FTLTISSLQP EDFATYYCQQ LNSYPWTFGQ GTKVDIK                            107

SEQ ID NO: 14           moltype = AA   length = 9
FEATURE                 Location/Qualifiers
source                  1..9
                        mol_type = protein
                        organism = synthetic construct
SEQUENCE: 14
QQLNSYPWT                                                                      9

SEQ ID NO: 15           moltype = AA   length = 15
FEATURE                 Location/Qualifiers
source                  1..15
                        mol_type = protein
                        organism = synthetic construct
SEQUENCE: 15
GGGGSGGGGS GGGGS                                                               15

SEQ ID NO: 16           moltype = AA   length = 19
FEATURE                 Location/Qualifiers
source                  1..19
                        mol_type = protein
                        organism = synthetic construct
SEQUENCE: 16
GGGGSGGGGS GGGSGGGGS                                                           19

SEQ ID NO: 17           moltype = AA   length = 24
```

| FEATURE | Location/Qualifiers |
|---|---|
| source | 1..24<br>mol_type = protein<br>organism = synthetic construct |

SEQUENCE: 17
```
GGGGSGGGGS GGGGSGGGSG GGGS                                           24
```

| SEQ ID NO: 18 | moltype = AA  length = 20 |
|---|---|
| FEATURE | Location/Qualifiers |
| source | 1..20<br>mol_type = protein<br>organism = synthetic construct |

SEQUENCE: 18
```
GGGGSGGGGS GGGGSGGGGS                                                20
```

| SEQ ID NO: 19 | moltype = AA  length = 488 |
|---|---|
| FEATURE | Location/Qualifiers |
| source | 1..488<br>mol_type = protein<br>organism = synthetic construct |

SEQUENCE: 19
```
MEFGLSWLFL VAILKGVQCE VQLVESGGDV VQPGRSLRLS CAASGFTFSS YAIHWVRQAP     60
GKGLEWVAVT WHDGSNKYYA ESVMGRFTIS RDNSKNTLYL HMNSLRAEDT GVYYCARAKF    120
GEPQYFQHWG QGTTVTVSSG GGGSGGGGSG GGGSDIVMTQ SPSFLSASVG DRVTITCRAS    180
QGISSYLAWY QQKPGKAPKL LIYAASTLQS GVPSRFSGSG SGTEFTLTIS SLQPEDFATY    240
YCQQLNSYPF TFGPGTKVDI KRAAAIEVMY PPPYLDNEKS NGTIIHVKGK HLCPSPLFPG    300
PSKPKDPKFW VLVVVGGVLA CYSLLVTVAF IIFWVRSKRS RLLHSDYMNM TPRRPGPTRK    360
HYQPYAPPRD FAAYRSRVKF SRSADAPAYQ QGQNQLYNEL NLGRREEYDV LDKRRGRDPE    420
MGGKPRRKNP QEGLYNELQK DKMAEAYSEI GMKGERRRGK GHDGLYQGLS TATKDTYDAL    480
HMQALPPR                                                            488
```

| SEQ ID NO: 20 | moltype = AA  length = 488 |
|---|---|
| FEATURE | Location/Qualifiers |
| source | 1..488<br>mol_type = protein<br>organism = synthetic construct |

SEQUENCE: 20
```
MEFGLSWLFL VAILKGVQCQ ITLRESGGDV VQPGRSLRLS CAASGFTFSS YAIHWVRQAP     60
GKGLEWVAVT WHDGSNKYYA ESVMGRFTIS RDNSKNTLYL HMNSLRAEDT GVYYCARAKF    120
GEPQYFQHWG QGTLVTVSSG GGGSGGGGSG GGGSDIVMTQ SPSFLSASVG DRVTITCRAS    180
QGINNYLAWY QQKPGIAPKL LIYAASTLQS GVPSRFGGSG SGTEFTLTIS SLQPEDFATY    240
YCQQLKSYPF TFGPGTKVEI KRAAAIEVMY PPPYLDNEKS NGTIIHVKGK HLCPSPLFPG    300
PSKPKDPKFW VLVVVGGVLA CYSLLVTVAF IIFWVRSKRS RLLHSDYMNM TPRRPGPTRK    360
HYQPYAPPRD FAAYRSRVKF SRSADAPAYQ QGQNQLYNEL NLGRREEYDV LDKRRGRDPE    420
MGGKPRRKNP QEGLYNELQK DKMAEAYSEI GMKGERRRGK GHDGLYQGLS TATKDTYDAL    480
HMQALPPR                                                            488
```

| SEQ ID NO: 21 | moltype = AA  length = 688 |
|---|---|
| FEATURE | Location/Qualifiers |
| source | 1..688<br>mol_type = protein<br>organism = synthetic construct |

SEQUENCE: 21
```
MEFGLSWLFL VAILKGVQCQ ITLRESGGDV VQPGRSLRLS CAASGFTFSS YAIHWVRQAP     60
GKGLEWVAVT WHDGSNKYYA ESVMGRFTIS RDNSKNTLYL HMNSLRAEDT GVYYCARAKF    120
GEPQYFQHWG QGTLVTVSSG GGGSGGGGSG GGGSDIVMTQ SPSFLSASVG DRVTITCRAS    180
QGISSYLAWY QQKPGKAPKL LIYAASTLQS GVPSRFSGSG SGTEFTLTIS SLQPEDFATY    240
YCQQLNSYPW TFGQGTKVDI KRTVTVSSQD PAEPKSPDKT HTCPPCPAPE LLGGPSVFLF    300
PPKPKDTLMI SRTPEVTCVV VDVSHEDPEV KFNWYVDGVE VHNAKTKPRE EQYNSTYRVV    360
SVLTVLHQDW LNGKEYKCKV SNKALPAPIE KTISKAKGQP REPQVYTLPP SRDELTKNQV    420
SLTCLVKGFY PSDIAVEWES NGQPENNYKT TPPVLDSDGS FFLYSKLTVD KSRWQQGNVF    480
SCSVMHEALH NHYTQKSLSL SPGKKDPKFW VLVVVGGVLA CYSLLVTVAF IIFWVRSKRS    540
RLLHSDYMNM TPRRPGPTRK HYQPYAPPRD FAAYRSRVKF SRSADAPAYQ QGQNQLYNEL    600
NLGRREEYDV LDKRRGRDPE MGGKPRRKNP QEGLYNELQK DKMAEAYSEI GMKGERRRGK    660
GHDGLYQGLS TATKDTYDAL HMQALPPR                                      688
```

| SEQ ID NO: 22 | moltype = AA  length = 184 |
|---|---|
| FEATURE | Location/Qualifiers |
| source | 1..184<br>mol_type = protein<br>organism = Homo sapiens |

SEQUENCE: 22
```
MLQMAGQCSQ NEYFDSLLHA CIPCQLRCSS NTPPLTCQRY CNASVTNSVK GTNAILWTCL     60
GLSLIISLAV FVLMFLLRKI SSEPLKDEFK NTGSGLLGMA NIDLEKSRTG DEIILPRGLE    120
YTVEECTCED CIKSKPKVDS DHCFPLPAME EGATILVTTK TNDYCKSLPA ALSATEIEKS    180
ISAR                                                                184
```

| SEQ ID NO: 23 | moltype = AA  length = 133 |
|---|---|
| FEATURE | Location/Qualifiers |

```
source                          1..133
                                mol_type = protein
                                organism = Homo sapiens
SEQUENCE: 23
GIHVFILGCF SAGLPKTEAN WVNVISDLKK IEDLIQSMHI DATLYTESDV HPSCKVTAMK    60
CFLLELQVIS LESGDASIHD TVENLIILAN NSLSSNGNVT ESGCKECEEL EEKNIKEFLQ   120
SFVHIVQMFI NTS                                                      133

SEQ ID NO: 24                   moltype = AA   length = 60
FEATURE                         Location/Qualifiers
source                          1..60
                                mol_type = protein
                                organism = synthetic construct
SEQUENCE: 24
GGTGGTGGTG GTTCTGGTGG TGGTGGTTCT GGCGGCGGCG GCTCCGGTGG TGGTGGATCC    60

SEQ ID NO: 25                   moltype = AA   length = 233
FEATURE                         Location/Qualifiers
source                          1..233
                                mol_type = protein
                                organism = Homo sapiens
SEQUENCE: 25
MSTESMIRDV ELAEEALPKK TGGPQGSRRC LFLSLFSFLI VAGATTLFCL LHFGVIGPQR    60
EEFPRDLSLI SPLAQAVRSS SRTPSDKPVA HVVANPQAEG QLQWLNRRAN ALLANGVELR   120
DNQLVVPSEG LYLIYSQVLF KGQGCPSTHV LLTHTISRIA VSYQTKVNLL SAIKSPCQRE   180
TPEGAEAKPW YEPIYLGGVF QLEKGDRLSA EINRPDYLDF AESGQVYFGI IAL          233

SEQ ID NO: 26                   moltype = AA   length = 27
FEATURE                         Location/Qualifiers
source                          1..27
                                mol_type = protein
                                organism = synthetic construct
SEQUENCE: 26
FWVLVVVGGV LACYSLLVTV AFIIFWV                                        27

SEQ ID NO: 27                   moltype = DNA  length = 81
FEATURE                         Location/Qualifiers
source                          1..81
                                mol_type = other DNA
                                organism = synthetic construct
SEQUENCE: 27
ttttgggtgc tggtggtggt tggtggagtc ctggcttgct atagcttgct agtaacagtg    60
gcctttatta ttttctgggt g                                              81

SEQ ID NO: 28                   moltype = AA   length = 41
FEATURE                         Location/Qualifiers
source                          1..41
                                mol_type = protein
                                organism = synthetic construct
SEQUENCE: 28
RSKRSRLLHS DYMNMTPRRP GPTRKHYQPY APPRDFAAYR S                        41

SEQ ID NO: 29                   moltype = DNA  length = 123
FEATURE                         Location/Qualifiers
source                          1..123
                                mol_type = other DNA
                                organism = synthetic construct
SEQUENCE: 29
aggagtaaga ggagcaggct cctgcacagt gactacatga acatgactcc ccgccgcccc    60
gggcccaccc gcaagcatta ccagccctat gccccaccac gcgacttcgc agcctatcgc   120
tca                                                                 123

SEQ ID NO: 30                   moltype = AA   length = 112
FEATURE                         Location/Qualifiers
source                          1..112
                                mol_type = protein
                                organism = synthetic construct
SEQUENCE: 30
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 31                   moltype = DNA  length = 336
FEATURE                         Location/Qualifiers
source                          1..336
                                mol_type = other DNA
                                organism = synthetic construct
SEQUENCE: 31
cgcgtgaagt tcagcaggag cgcagacgcc ccgcgtacc agcagggcca gaaccagctc    60
tataacgagc tcaatctagg acgaagagag gagtacgatg ttttggacaa aagacgtggc   120
```

```
cgggaccctg agatggggg  aaagccgaga aggaagaacc ctcaggaagg cctgtacaat    180
gaactgcaga aagataagat ggcgaggcc  tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

SEQ ID NO: 32         moltype = AA   length = 29
FEATURE               Location/Qualifiers
source                1..29
                      mol_type = protein
                      organism = synthetic construct
SEQUENCE: 32
MRISKPHLRS ISIQCYLCLL LNSHFLTEA                                      29

SEQ ID NO: 33         moltype = DNA  length = 87
FEATURE               Location/Qualifiers
source                1..87
                      mol_type = other DNA
                      organism = synthetic construct
SEQUENCE: 33
atgcgcatta gcaagcccca cctgcggagc atcagcatcc agtgctacct gtgcctgctg    60
ctgaacagcc acttcctgac cgaggcc                                        87

SEQ ID NO: 34         moltype = DNA  length = 399
FEATURE               Location/Qualifiers
source                1..399
                      mol_type = other DNA
                      organism = synthetic construct
SEQUENCE: 34
ggcatccacg tgttcatcct ggctgcttc  agcgccggac tgcccaagac cgaggccaac    60
tgggtgaacg tgatcagcga cctgaagaag atcgaggacc tgatccagag catgcacatc    120
gacgccaccc tgtacaccga gagcgacgtg cacccagct  gcaaggtgac cgccatgaag    180
tgctttctgc tggaactgca ggtgatcagc tggaaagcg  gcgacgccag catccacgac    240
accgtggaga acctgatcat cctggccaac aacagcctga gcagcaacgg caacgtgacc    300
gagagcggct gcaaagagtg cgaggaactg aagagaaga  acatcaaaga gtttctgcag    360
agcttcgtgc acatcgtgca gatgttcatc aacaccagc                           399

SEQ ID NO: 35         moltype = DNA  length = 141
FEATURE               Location/Qualifiers
source                1..141
                      mol_type = other DNA
                      organism = synthetic construct
SEQUENCE: 35
cgggcggccg caattgaagt tatgtatcct cctccttacc tagacaatga gaagagcaat    60
ggaaccatta tccatgtgaa agggaaacac ctttgtccaa gtcccctatt tcccggacct    120
tctaagccca agatcccaa  a                                              141

SEQ ID NO: 36         moltype = AA   length = 47
FEATURE               Location/Qualifiers
source                1..47
                      mol_type = protein
                      organism = synthetic construct
SEQUENCE: 36
RAAAIEVMYP PYLDNEKSN GTIIHVKGKH LCPSPLFPGP SKPKDPK                   47

SEQ ID NO: 37         moltype = AA   length = 247
FEATURE               Location/Qualifiers
source                1..247
                      mol_type = protein
                      organism = synthetic construct
SEQUENCE: 37
RTVTVSSQDP AEPKSPDKTH TCPPCPAPEL LGGPSVFLFP PKPKDTLMIS RTPEVTCVVV    60
DVSHEDPEVK FNWYVDGVEV HNAKTKPREE QYNSTYRVVS VLTVLHQDWL NGKEYKCKVS    120
NKALPAPIEK TISKAKGQPR EPQVYTLPPS RDELTKNQVS LTCLVKGFYP SDIAVEWESN    180
GQPENNYKTT PPVLDSDGSF FLYSKLTVDK SRWQQGNVFS CSVMHEALHN HYTQKSLSLS    240
PGKKDPK                                                              247

SEQ ID NO: 38         moltype = DNA  length = 741
FEATURE               Location/Qualifiers
source                1..741
                      mol_type = other DNA
                      organism = synthetic construct
SEQUENCE: 38
cgtacggtca ctgtctcttc acaggatccc gccgagccca aatctcctga caaaactcac    60
acatgcccac cgtgcccagc acctgaactc ctggggggac cgtcagtctt cctcttcccc    120
ccaaaaccca aggacaccct catgatctcc cggaccctg  aggtcacatg cgtggtggtg    180
gacgtgagcc acgaagaccc tgaggtcaag ttcaactggt acgtggacgg cgtggaggtg    240
cataatgcca agacaaagcc gcgggaggag cagtacaaca gcacgtaccg tgtggtcagc    300
gtcctcaccg tcctgcacca ggactggctg aatggcaagg agtacaagtg caaggtctcc    360
aacaaagccc tcccagcccc catcgagaaa accatctcca aagccaaagg gcagcccga    420
```

```
gaaccacagg tgtacaccct gcccccatcc cgggatgagc tgaccaagaa ccaggtcagc    480
ctgacctgcc tggtcaaagg cttctatccc agcgacatcg ccgtggagtg ggagagcaat    540
gggcaaccgg agaacaacta caagaccacg cctcccgtgc tggactccga cggctccttc    600
ttcctctaca gcaagctcac cgtggacaag agcaggtggc agcaggggaa cgtcttctca    660
tgctccgtga tgcatgaggc tctgcacaac cactacacgc agaagagcct ctccctgtct    720
ccgggtaaaa aagatcccaa a                                              741

SEQ ID NO: 39           moltype = AA  length = 22
FEATURE                 Location/Qualifiers
source                  1..22
                        mol_type = protein
                        organism = synthetic construct
SEQUENCE: 39
GPQCTNYALL KLAGDVESNP GP                                              22

SEQ ID NO: 40           moltype = DNA  length = 66
FEATURE                 Location/Qualifiers
source                  1..66
                        mol_type = other DNA
                        organism = synthetic construct
SEQUENCE: 40
ggaccgcagt gtactaatta tgctctcttg aaattggctg gagatgttga gagcaatccc    60
gggccc                                                                66

SEQ ID NO: 41           moltype =    length =
SEQUENCE: 41
000

SEQ ID NO: 42           moltype = DNA  length = 1467
FEATURE                 Location/Qualifiers
source                  1..1467
                        mol_type = other DNA
                        organism = synthetic construct
SEQUENCE: 42
atggaatttg gactgtcatg gcttttctct gtcgccatcc tgaaaggggt acagtgtgaa    60
gtgcaactgg tcgaatctgg gggagacgtt gtccagcccg ggaggtcttt gcggttgtca    120
tgcgcagctt caggttttac tttctcttca tacgccatcc attgggttcg gcaagcgcct    180
ggtaagggac tcgaatgggt tgcagtgacc tggcatgacg gatcaaacaa gtattatgca    240
gaatcagtaa tgggcaggtt taccatttca cgcgacaata gcaaaaatac actttatttg    300
cacatgaatt cactcagagc cgaagatacc ggcgtctatt attgcgccag agcaaaattt    360
ggggagccac agtacttcca acattgggga caaggcacta ccgtcaccgt gagttcaggc    420
ggggggggat caggcggagg aggttcaggc ggcggcggca gtgacatagt gatgactcag    480
agtccttcat ttttgagcgc aagtgttggg gataggtca ctataacgtg tagagcatct    540
caaggcattt cttcatattt ggcctggtat aacagaaac ctggaaaggc ccaaaagctc    600
cttatttacg ctgcatcaac cctgcaatct ggcgtcccaa gccgattctc tgggtctgga    660
agcggcacag aatttaccct gactatatca tctctccaac tgaagatttt gccaccat     720
tattgtcagc aattgaattc atacccgttc acattcggcc agggaactaa agtcgacatc    780
aagcgggcgg ccgcaattga agttatgtat cctcctcctt acctagacaa tgagaagagc    840
aatggaacca ttatccatgt gaaagggaaa cacctttgtc caagtcccct atttcccgga    900
ccttctaagc ccaaagatcc caaatttttgg gtgctggtgg tggttggtgg agtcctggct    960
tgctatagct tgctagtaac agtggccttt attattttct gggtgaggag taagaggagc    1020
aggctcctgc acagtgacta catgaacatg actccccgcc gccccgggcc caccccgaag    1080
cattaccagc cctatgcccc accacgcgac ttcgcagcct atcgctcacg cgtgaagttc    1140
agcaggagcg cagacgcccc cgcgtaccag cagggccaga accagctcta taacgagctc    1200
aatctaggac gaagagagga gtacgatgtt ttggacaaga cgtggccga ggaccctgag    1260
atgggggaa agccgagaag gaagaaccct caggaaggcc tgtacaatga actgcagaaa    1320
gataagatgg cggaggccta cagtgagatt gggatgaaag cgagcgccg gaggggcaag    1380
gggcacgatg gcctttacca gggtctcagt acagccacca aggacaccta cgacgccctt    1440
cacatgcagg ccctgccccc tcgctga                                        1467

SEQ ID NO: 43           moltype = DNA  length = 1467
FEATURE                 Location/Qualifiers
source                  1..1467
                        mol_type = other DNA
                        organism = synthetic construct
SEQUENCE: 43
atggaattcg gctgtcctg gcttttcttg gtcgcaattc ttaagggcgt ccaatgtcag    60
ataactctgc gcgagtcagg aggagacgtg gtgcaaccgg gcagatctct caggctttca    120
tgtgccgcca gtggcttcac atttagctct tatgcaatac attgggtcag gcaggctcct    180
ggcaagggct tggaatgggt agcggttacc tggcatgatg gatctaacaa atactacgcc    240
gagtctgtta tgggtcgatt cacaatttct cgagacaatt caaaaaacac actctacctg    300
catatgaact cacttagagc agaggacact ggtgtctatt actgcgccag agcaaaattc    360
ggcgagccac agtatttcca gcactgggga caaggaaccc tcgtaacagt atctagtggg    420
ggaggggt ctgaggagg gggaagcggg ggaggcggca gtgatattgt tatgacccaa    480
tcaccatctt ttctgagcgc tagtgtcggg acagggtta acaatcacatg ccgagcaagc    540
caaggaatca acaattatct cgcatggtat aacaaaaac caggtatcgc cccgaaactt    600
cttatttacg cagcatcaac cctgcaaagc ggagttcctt ctagatttgg tggcagcggc    660
tccgggactg aattcactct tactatttcc tcccttcaac ccgaagattt cgccacatat    720
tactgccagc agcttaagtc atacccctca acttttggcc aggaactaa agttgaaatc    780
```

```
aaacgggcgg ccgcaattga agttatgtat cctcctcctt acctagacaa tgagaagagc  840
aatggaacca ttatccatgt gaaagggaaa cacctttgtc caagtcccct atttcccgga  900
ccttctaagc ccaaagatcc caaatttggg gtgctggtgg tggttggtgg agtcctggct  960
tgctatagct tgctagtaac agtggccttt attattttct gggtgaggag taagaggagc 1020
aggctcctgc acagtgacta catgaacatg actccccgcc gccccgggcc cacccgcaag 1080
cattaccagc cctatgcccc accacgcgac ttcgcagcct atcgctcacg cgtgaagttc 1140
agcaggagcg cagacgcccc cgcgtaccag cagggccaga accagctcta taacgagctc 1200
aatctaggac gaagagagga gtacgatgtt ttggacaaaa gacgtggccg ggaccctgag 1260
atgggggaa agccgagaag gaagaaccct caggaaggcc tgtacaatga actgcagaaa 1320
gataagatgg cggaggccta cagtgagatt gggatgaaag cgagcgccg gaggggcaag 1380
gggcacgatg gcctttacca gggtctcagt acagccacca aggacaccta cgacgccctt 1440
cacatgcagg ccctgccccc tcgctga                                    1467

SEQ ID NO: 44           moltype = DNA  length = 1467
FEATURE                 Location/Qualifiers
source                  1..1467
                        mol_type = other DNA
                        organism = synthetic construct
SEQUENCE: 44
atggaattcg ggctgtcctg gctttttctg gtcgcaattc ttaagggcgt ccaatgtcag   60
ataactctgc gcgagtcagg aggagacgtg gtgcaaccgg gcagatctct caggctttca  120
tgtgccgcca gtggcttcac atttagctct tatgcaatac attgggtcag gcaggctcct  180
ggcaagggct tggaatgggt agcggttacc tggcatgatg gatctaacaa atactacgcc  240
gagtctgtta tgggtcgatt cacaatttct cgagacaatt caaaaaacac actctacctg  300
catatgaact cacttagagc agaggacact ggtgtctatt actgcgccag agcaaaattc  360
ggcgagccac agtatttcca gcactgggga caaggaaccc tcgtaacagt atctagtggg  420
ggcggagggt ctggaggagg ggggagcggg ggaggcggct ctgatattgt tatgacccaa  480
tcaccatctt ttctgagcgc tagtgtcggc gacagggtta caatcacatg ccgagcaagc  540
caaggaatca caattatctc gcatggtat caacaaaaac caggtatcgc cccgaaactt  600
cttatttacg cagcatcaac cctgcaaagc ggagttcctt ctagatttgg tggcagcggc  660
tccgggactg aattcactct tactatttcc tcccttcaac ccgaagattt cgccacatat  720
tactgccagc agcttaagtc ataccccttc acttttggcc caggaactaa agttgaaatc  780
aaacgggcgg ccgcaattga agttatgtat cctcctcctt acctagacaa tgagaagagc  840
aatggaacca ttatccatgt gaaagggaaa cacctttgtc caagtcccct atttcccgga  900
ccttctaagc ccaaagatcc caaatttggg gtgctggtgg tggttggtgg agtcctggct  960
tgctatagct tgctagtaac agtggccttt attattttct gggtgaggag taagaggagc 1020
aggctcctgc acagtgacta catgaacatg actccccgcc gccccgggcc cacccgcaag 1080
cattaccagc cctatgcccc accacgcgac ttcgcagcct atcgctcacg cgtgaagttc 1140
agcaggagcg cagacgcccc cgcgtaccag cagggccaga accagctcta taacgagctc 1200
aatctaggac gaagagagga gtacgatgtt ttggacaaaa gacgtggccg ggaccctgag 1260
atgggggaa agccgagaag gaagaaccct caggaaggcc tgtacaatga actgcagaaa 1320
gataagatgg cggaggccta cagtgagatt gggatgaaag cgagcgccg gaggggcaag 1380
gggcacgatg gcctttacca gggtctcagt acagccacca aggacaccta cgacgccctt 1440
cacatgcagg ccctgccccc tcgctga                                    1467

SEQ ID NO: 45           moltype = AA  length = 672
FEATURE                 Location/Qualifiers
source                  1..672
                        mol_type = protein
                        organism = synthetic construct
SEQUENCE: 45
MEFGLSWLFL VAILKGVQCE VQLVESGGDV VQPGRSLRLS CAASGFTFSS YAIHWVRQAP   60
GKGLEWVAVT WHDGSNKYYA ESVMGRFTIS RDNSKNTLYL HMNSLRAEDT GVYYCARAKF  120
GEPQYFQHWG QGTTVTVSSG GGGSGGGGSG GGGSDIVMTQ SPSFLSASVG DRVTITCRAS  180
QGISSYLAWY QQKPGKAPKL LIYAASTLQS GVPSRFSGSG SGTEFTLTIS SLQPEDFATY  240
YCQQLNSYPF TFGPGTKVDI KRAAAIEVMY PPPYLDNEKS NGTIIHVKGK HLCPSPLFPG  300
PSKPKDPKFW VLVVVGGVLA CYSLLVTVAF IIFWVRSKRS RLLHSDYMNM TPRRPGPTRK  360
HYQPYAPPRD FAAYRSRVKF SRSADAPAYQ QGQNQLYNEL NLGRREEYDV LDKRRGRDPE  420
MGGKPRRKNP QEGLYNELQK DKMAEAYSEI GMKGERRRGK GHDGLYQGLS TATKDTYDAL  480
HMQALPPRGP QCTNYALLKL AGDVESNPGP MRISKPHLRS ISIQCYLCLL LNSHFLTEAG  540
IHVFILGCFS AGLPKTEANW VNVISDLKKI EDLIQSMHID ATLYTESDVH PSCKVTAMKC  600
FLLELQVISL ESGDASIHDT VENLIILANN SLSSNGNVTE SGCKECEELE EKNIKEFLQS  660
FVHIVQMFIN TS                                                     672

SEQ ID NO: 46           moltype = DNA  length = 2019
FEATURE                 Location/Qualifiers
source                  1..2019
                        mol_type = other DNA
                        organism = synthetic construct
SEQUENCE: 46
atggaatttg gactgtcatg gcttttcctt gtcgccatcc tgaaaggggt acagtgtgaa   60
gtgcaactgg tcgaatctgg gggagacgtt gtccagcccg ggaggtcttt gcggttgtca  120
tgcgcagctt caggttttac tttctcttca tacgccatcc attgggttcg gcaagcgcct  180
ggtaagggac tcgaatgggt tgcagtgacc tggcatgacg gatcgaacaa gtattatgca  240
gaatcagtaa tgggcaggtt taccatttca cgcgacaata gcaaaaatac actttatttg  300
cacatgaatt cactcagagc cgaagatacc ggcgtctatt attgcgccag agcaaaattt  360
ggggagccac agtacttcca acattgggga caaggcacta ccgtcaccgt gagttcaggc  420
gggggggat caggcggagg aggttcaggc ggcgcggca gtgacatagt gatgactcag  480
agtccttcat ttttgagcgc aagtgttggg atagggtca ctataacgtg tagagcatct  540
```

```
caaggcattt cttcatattt ggcctggtat caacagaaac ctggaaaggc cccaaagctc    600
cttatttacg ctgcatcaac cctgcaatct ggcgtcccaa gccgattctc tgggtctgga    660
agcggcacag aatttaccct gactatatca tctctccaac ctgaagattt tgccaccat    720
tattgtcagc aattgaattc atacccgttc acattcggcc ctggaactaa agtcgacatc    780
aagcggccgg ccgcaattga agttatgtat cctcctcctt acctagacaa tgagaagagc    840
aatgaaacca ttatccatgt gaaagggaaa caccttttgtc caagtcccct atttcccgga    900
ccttctaagc ccaaagatcc caaatttttgg gtgctggtgg tggttggtgg agtcctggct    960
tgctatagct tgctagtaac agtggccttt attattttct gggtgaggag taagaggagc   1020
aggctcctgc acagtgacta catgaacatg actccccgcc gccccgggcc cacccgcaag   1080
cattaccagc cctatgcccc accacgcgac ttcgcagcct atcgctcacg cgtgaagttc   1140
agcaggagcg cagacgcccc cgcgtaccag cagggccaga accagctcta taacgagctc   1200
aatctaggac gaagagagga gtacgatgtt ttggacaaaa gacgtggccg ggaccctgag   1260
atgggggggaa agccgagaag gaagaaccct caggaaggcc tgtacaatga actgcagaaa   1320
gataagatgg cggaggccta cagtgagatt gggatgaaga gcgagcgccg gagggggcaag   1380
gggcacgatg gcctttacca gggtctcagt acagccacca aggacaccta cgacgccctt   1440
cacatgcagg ccctgccccc tcgcggaccg cagtgtacta attatgctct cttgaaattg   1500
gctggagatg ttgagagcaa tcccgggccc atgcgcatta gcaagcccca cctgcggagc   1560
atcagcatcc agtgctacct gtgcctgctg ctgaacagcc acttcctgac cgaggccggc   1620
atccacgtgt tcatcctggg ctgcttcagc gccggactgc ccaagaccga ggccaactgg   1680
gtgaacgtga tcagcgacct gaagaagatc gaggacctga tccagagcat gcacatcgac   1740
gccacctctg acaccgagag cgacgtgcac cccagctgca aggtgaccgc catgaagtgc   1800
tttctgctgg aactgcaggt gatcagcctg gaaagcggcg acgccagcat ccacgacact   1860
gtggagaacc tgatcatcct ggccaacaac agcctgagca gcaacggcaa cgtgaccgag   1920
agcggctgca aagagtgcga ggaactggaa gagaagaaca tcaaagagtt tctgcagagc   1980
ttcgtgcaca tcgtgcagat gttcatcaac accagctga                         2019

SEQ ID NO: 47         moltype = AA  length = 672
FEATURE               Location/Qualifiers
source                1..672
                      mol_type = protein
                      organism = synthetic construct
SEQUENCE: 47
MEFGLSWLFL VAILKGVQCQ ITLRESGGDV VQPGRSLRLS CAASGFTFSS YAIHWVRQAP    60
GKGLEWVAVT WHDGSNKYYA ESVMGRFTIS RDNSKNTLYL HMNSLRAEDT GVYYCARAKF   120
GEPQYFQHWG QGTLVTVSSG GGGSGGGGSG GGGSDIVMTQ SPSFLSASVG DRVTITCRAS   180
QGINNYLAWY QQKPGIAPKL LIYAASTLQS GVPSRFGGSG SGTEFTLTIS SLQPEDFATY   240
YCQQLKSYPF TFGPGTKVEI KRAAAIEVMY PPPYLDNEKS NGTIIHVKGK HLCPSPLFPG   300
PSKPKDPKFW VLVVVGGVLA CYSLLVTVAF IIFWVRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPRRKNP QEGLYNELQK DKMAEAYSEI GMKGERRRGK GHDGLYQGLS TATKDTYDAL   480
HMQALPPRGP QCTNYALLKL AGDVESNPGP MRISKPHLRS ISIQCYLCLL LNSHFLTEAG   540
IHVFILGCFS AGLPKTEANW VNVISDLKKI EDLIQSMHID ATLYTESDVH PSCKVTAMKC   600
FLLELQVISL ESGDASIHDT VENLIILANN SLSSNGNVTE SGCKECEELE EKNIKEFLQS   660
FVHIVQMFIN TS                                                       672

SEQ ID NO: 48         moltype = DNA length = 2019
FEATURE               Location/Qualifiers
source                1..2019
                      mol_type = other DNA
                      organism = synthetic construct
SEQUENCE: 48
atggaattcg gctgtcctg gcttttcttg gtcgcaattc ttaagggcgt ccaatgtcag      60
ataactctgc gcgagtcagg aggagacgtg gtgcaaccgg gcagatctct caggcttttca   120
tgtgccgcca gtggcttcac atttagctct tatgcaatac attgggtcag gcaggctcct   180
ggcaagggct tggaatgggt agcggttacc tggcatgatg gatctaacaa atactacgcc   240
gagtctgtta tgggtcgatt cacaattttct cgagacaatt caaaaaacac actctacctg   300
catatgaact cacttagagc agaggacact ggtgtctatt actgcgccag agcaaaattc   360
ggcgagccac agtatttcca gcactgggga caaggaaccc tcgtaacagt atctagtggg   420
ggcggagggt ctgaggaggg ggggagcggg ggaggcggct ctgatattgt tatgacccaa   480
tcaccatctt ttctgagcgc tagtgtcggc gacagggtta caattcactg ccgagcaagc   540
caaggaatca acaattatct cgcatggtat caacaaaaac caggtatcgc cccgaaactt   600
cttatttacg cagcatcaac cctgcaaagc ggagttcctt ctagatttgg tggcagcggc   660
tccgggactg aattcactct tactatttcc tcccttcaac ccgaagattt cgccacatat   720
tactgccagc agcttaagtc ataccccttc acttttggcc ctggaactaa agttgaaatc   780
aaacggcgg ccgcaattga agttatgtat cctcctcctt acctagacaa tgagaagagc    840
aatgaaacca ttatccatgt gaaagggaaa caccttttgtc caagtcccct atttcccgga    900
ccttctaagc ccaaagatcc caaatttttgg gtgctggtgg tggttggtgg agtcctggct    960
tgctatagct tgctagtaac agtggccttt attattttct gggtgaggag taagaggagc   1020
aggctcctgc acagtgacta catgaacatg actccccgcc gccccgggcc cacccgcaag   1080
cattaccagc cctatgcccc accacgcgac ttcgcagcct atcgctcacg cgtgaagttc   1140
agcaggagcg cagacgcccc cgcgtaccag cagggccaga accagctcta taacgagctc   1200
aatctaggac gaagagagga gtacgatgtt ttggacaaaa gacgtggccg ggaccctgag   1260
atgggggggaa agccgagaag gaagaaccct caggaaggcc tgtacaatga actgcagaaa   1320
gataagatgg cggaggccta cagtgagatt gggatgaaga gcgagcgccg gagggggcaag   1380
gggcacgatg gcctttacca gggtctcagt acagccacca aggacaccta cgacgccctt   1440
cacatgcagg ccctgccccc tcgcggaccg cagtgtacta attatgctct cttgaaattg   1500
gctggagatg ttgagagcaa tcccgggccc atgcgcatta gcaagcccca cctgcggagc   1560
atcagcatcc agtgctacct gtgcctgctg ctgaacagcc acttcctgac cgaggccggc   1620
atccacgtgt tcatcctggg ctgcttcagc gccggactgc ccaagaccga ggccaactgg   1680
```

-continued

```
gtgaacgtga tcagcgacct gaagaagatc gaggacctga tccagagcat gcacatcgac 1740
gccaccctgt acaccgagag cgacgtgcac cccagctgca aggtgaccgc catgaagtgc 1800
tttctgctgg aactgcaggt gatcagcctg gaaagcggcg acgccagcat ccacgacacc 1860
gtggagaacc tgatcatcct ggccaacaac agcctgagca gcaacggcaa cgtgaccgag 1920
agcggctgca aagagtgcga ggaactggaa gagaagaaca tcaaagagtt tctgcagagc 1980
ttcgtgcaca tcgtgcagat gttcatcaac accagctga                         2019
```

| SEQ ID NO: 49 | moltype = AA length = 872 |
|---|---|
| FEATURE | Location/Qualifiers |
| source | 1..872 |
| | mol_type = protein |
| | organism = synthetic construct |

SEQUENCE: 49
```
MEFGLSWLFL VAILKGVQCQ ITLRESGGDV VQPGRSLRLS CAASGFTFSS YAIHWVRQAP  60
GKGLEWVAVT WHDGSNKYYA ESVMGRFTIS RDNSKNTLYL HMNSLRAEDT GVYYCARAKF 120
GEPQYFQHWG QGTLVTVSSG GGGSGGGGSG GGGSDIVMTQ SPSFLSASVG DRVTITCRAS 180
QGISSYLAWY QQKPGKAPKL LIYAASTLQS GVPSRFSGSG SGTEFTLTIS SLQPEDFATY 240
YCQQLNSYPW TFGQGTKVDI KRTVTVSSQD PAEPKSPDKT HTCPPCPAPE LLGGPSVFLF 300
PPKPKDTLMI SRTPEVTCVV VDVSHEDPEV KFNWYVDGVE VHNAKTKPRE EQYNSTYRVV 360
SVLTVLHQDW LNGKEYKCKV SNKALPAPIE KTISKAKGQP REPQVYTLPP SRDELTKNQV 420
SLTCLVKGFY PSDIAVEWES NGQPENNYKT TPPVLDSDGS FFLYSKLTVD KSRWQQGNVF 480
SCSVMHEALH NHYTQKSLSL SPGKKDPKFW VLVVVGGVLA CYSLLVTVAF IIFWVRSKRS 540
RLLHSDYMNM TPRRPGPTRK HYQPYAPPRD FAAYRSRVKF SRSADAPAYQ QGQNQLYNEL 600
NLGRREEYDV LDKRRGRDPE MGGKPRRKNP QEGLYNELQK DKMAEAYSEI GMKGERRRGK 660
GHDGLYQGLS TATKDTYDAL HMQALPPRGP QCTNYALLKL AGDVESNPGP MRISKPHLRS 720
ISIQCYLCLL LNSHFLTEAG IHVFILGCFS AGLPKTEANW VNVISDLKKI EDLIQSMHID 780
ATLYTESDVH PSCKVTAMKC FLLELQVISL ESGDASIHDT VENLIILANN SLSSNGNVTE 840
SGCKECEELE EKNIKEFLQS FVHIVQMFIN TS                               872
```

| SEQ ID NO: 50 | moltype = DNA length = 2619 |
|---|---|
| FEATURE | Location/Qualifiers |
| source | 1..2619 |
| | mol_type = other DNA |
| | organism = synthetic construct |

SEQUENCE: 50
```
atggaattcg gattgtcatg gttgttcctc gtcgcaattc tcaagggcgt gcagtgccaa   60
attactcttc gagagtccgg cggagatgtg gtacagccag ggagaagcct gagactctcc  120
tgtgcagcaa gcggatttac ctttcttct tacgctatcc actgggttag acaggctccc  180
ggtaagggac tggaatgggt cgcagtaaca tggcacgacg gttcaaataa gtactacgca  240
gagtcagtca tgggaaggtt tactatttca cgggacaatt ctaagaacac actctacctg  300
catatgaact ccctcagagc tgaagacacc ggcgtatatt attgtgctag agctaaattt  360
ggagaaccac agtattttca acactggggc caaggcacac ttgtaacggt ttcaagcggt  420
ggtgggggt ctggcggagg aggtagtgga ggtggagcc cgatatcgt tatgacacaa  480
tcacccagct tcttgtcagc ttctgttggt gatcgggtaa caattacttg tcgcgcatct  540
cagggtatca gttcatatct ggcatggtat cagcaaaagc ctggaaaagc ccctaaactt  600
ctgatttacg ccgcgagcac actgcaaagt ggagttccgt caagattctc tggctctggg  660
tccggtaccg aatttacttt gactatcagc tcactccacc ctgaggattt cgccacgtac  720
tattgccaac agcttaactc ctatccttgg acatttggtc agggcactaa agttgatatt  780
aaacgtacgg tcactgtctc ttcacaggat cccgccgagc ccaaatctcc tgacaaaact  840
cacacatgcc caccgtgccc agcacctgaa ctcctggggg gaccgtcagt cttcctcttc  900
ccccccaaaac ccaaggacac cctcatgatc tcccggaccc ctgaggtcac atgcgtggtg  960
gtggacgtga gccacgaaga ccctgaggtc aagttcaact ggtacgtgga cggcgtggag 1020
gtgcataatg ccaagacaaa gccgcgggag gagcagtaca acagcacgta ccgtgtggtc 1080
agcgtcctca ccgtcctgca ccaggactgg ctgaatggca aggagtacaa gtgcaaggtc 1140
tccaacaaag ccctcccagc ccccatcgag aaaaccatct ccaaagccag agggcagccc 1200
cgagaaccac aggtgtacac cctgccccca tcccgggatg agctgaccaa gaaccaggtc 1260
agcctgacct gcctggtcaa aggcttctat cccagcgaca tcgccgtgga gtgggagagc 1320
aatgggcaac ggagaacaa ctacaagacc acgcctcccg tgctggactc cgacggctcc 1380
ttcttcctct acagcaagct caccgtggac aagagcaggt ggcagcaggg gaacgtcttc 1440
tcatgctccg tgatgcatga ggctctgcac aaccactaca cgcagaagag cctctccctg 1500
tctccgggta aaaaagatcc caaattttgg gtgctggtgg tggttggtgg agtcctggct 1560
tgctatagct tgctagtaac agtggccttt attattttct gggtgaggag taagaggagc 1620
aggctcctgc acagtgacta catgaacatg actccccgcc gccccgggcc cacccgcaag 1680
cattaccagc cctatgcccc accacgcgac ttcgcagcct atcgctcacg cgtgaagttc 1740
agcaggagcg cagacgcccc cgcgtaccag cagggccaga accagctcta taacgagctc 1800
aatctaggac gaagagagga gtacgatgtt ttggacaaaa gacgtggccg ggaccctgag 1860
atgggggaa agccgagaag gaagaaccct caggaaggcc tgtacaatga actgcagaaa 1920
gataagatgg cggaggccta cagtgagatt gggatgaaag gcgagcgccg gaggggcaag 1980
gggcacgatg gcctttacca gggtctcagt acagccacca aggacactac cgacgccctt 2040
cacatgcagg ccctgccccc tcgcggaccc cagtgtacta attatgctct cttgaaattg 2100
gctggagatg ttgagagcaa tccgggccc atgcgcatta gcaagcccca cctgcggagc 2160
atcagcatcc agtgctacct gtgcctgctg ctgaacagcc acttcctgac cgaggccggc 2220
atccacgtgt tcatcctggg ctgcttcagc gccggactgc ccaagaccga ggccaactgg 2280
gtgaacgtga tcagcgacct gaagaagatc gaggacctga tccagagcat gcacatcgac 2340
gccaccctgt acaccgagag cgacgtgcac cccagctgca aggtgaccgc catgaagtgc 2400
tttctgctgg aactgcaggt gatcagcctg gaaagcggcg acgccagcat ccacgacacc 2460
gtggagaacc tgatcatcct ggccaacaac agcctgagca gcaacggcaa cgtgaccgag 2520
agcggctgca aagagtgcga ggaactggaa gagaagaaca tcaaagagtt tctgcagagc 2580
ttcgtgcaca tcgtgcagat gttcatcaac accagctga                        2619
```

```
SEQ ID NO: 51            moltype = AA   length = 19
FEATURE                  Location/Qualifiers
source                   1..19
                         mol_type = protein
                         organism = synthetic construct
SEQUENCE: 51
MEFGLSWLFL VAILKGVQC                                                      19

SEQ ID NO: 52            moltype = DNA  length = 57
FEATURE                  Location/Qualifiers
source                   1..57
                         mol_type = other DNA
                         organism = synthetic construct
SEQUENCE: 52
atggaattcg gattgtcatg gttgttcctc gtcgcaattc tcaagggcgt gcagtgc            57

SEQ ID NO: 53            moltype = AA   length = 20
FEATURE                  Location/Qualifiers
source                   1..20
                         mol_type = protein
                         organism = synthetic construct
SEQUENCE: 53
QCTNYALLKL AGDVESNPGP                                                     20

SEQ ID NO: 54            moltype = AA   length = 449
FEATURE                  Location/Qualifiers
source                   1..449
                         mol_type = protein
                         organism = synthetic construct
SEQUENCE: 54
QITLRESGGD VVQPGRSLRL SCAASGFTFS SYAIHWVRQA PGKGLEWVAV TWHDGSNKYY   60
AESVMGRFTI SRDNSKNTLY LHMNSLRAED TGVYYCARAK FGEPQYFQHW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 55            moltype = DNA  length = 360
FEATURE                  Location/Qualifiers
source                   1..360
                         mol_type = other DNA
                         organism = synthetic construct
SEQUENCE: 55
cagatcactt taagggagag cggaggcgat gtggtgcagc ccggtcgttc tttaagactg   60
agctgtgccg ccagcggctt caccttcagc agctacgcca tccactgggt gagacaagct  120
cccggtaaag gtttagagtg ggtggctgtg acttggcacg acggctccaa caagtactat  180
gccgagagcg tgatgggtcg tttcaccatc tctcgtgaca cagcaagaa cacttttat   240
ttacacatga actcttttaag ggccgaggac accggcgtgt actactgcgc cagagccaag  300
ttcggcgagc ccagtacttt ccagcactgg ggccaaggta cactggtgac cgtgtccagc  360

SEQ ID NO: 56            moltype = DNA  length = 1347
FEATURE                  Location/Qualifiers
source                   1..1347
                         mol_type = other DNA
                         organism = synthetic construct
SEQUENCE: 56
cagatcactt taagggagag cggaggcgat gtggtgcagc ccggtcgttc tttaagactg   60
agctgtgccg ccagcggctt caccttcagc agctacgcca tccactgggt gagacaagct  120
cccggtaaag gtttagagtg ggtggctgtg acttggcacg acggctccaa caagtactat  180
gccgagagcg tgatgggtcg tttcaccatc tctcgtgaca cagcaagaa cacttttat   240
ttacacatga actcttttaag ggccgaggac accggcgtgt actactgcgc cagagccaag  300
ttcggcgagc ccagtacttt ccagcactgg ggccaaggta cactggtgac cgtgtccagc  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagag agttgagccc  660
aaatcttgtg acaaaactca cacatgccca ccgtgcccag cacctgaact cctgggggga  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcaaggtctc caacaaagcc ctcccagccc ccatcgagaa aaccatctcc  1020
aaagccaaag gcagccccg agaaccacag gtgtataccc tgcccccatc ccgggaggag  1080
atgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
```

```
ctggactccg acggctcctt cttcctctat agcaagctca ccgtggacaa gagcaggtgg    1260
cagcagggga acgtcttctc atgctccgtg atgcatgagg ctctgcacaa ccactacacg    1320
cagaagagcc tctccctgtc cccgggt                                        1347

SEQ ID NO: 57          moltype = AA   length = 449
FEATURE                Location/Qualifiers
source                 1..449
                       mol_type = protein
                       organism = synthetic construct
SEQUENCE: 57
EVQLVESGGD VVQPGRSLRL SCAASGFTFS SYAIHWVRQA PGKGLEWVAV TWHDGSNKYY     60
AESVMGRFTI SRDNSKNTLY LHMNSLRAED TGVYYCARAK FGEPQYFQHW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKRVEP KSCDKTHTCP PCPAPELLGG    240
PSVFLFPPKP KDTLMISRTP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSREE    360
MTKNQVSLTC LVKGFYPSDI AVEWESNGQP ENNYKTTPPV LDSDGSFFLY SKLTVDKSRW    420
QQGNVFSCSV MHEALHNHYT QKSLSLSPG                                     449

SEQ ID NO: 58          moltype = DNA   length = 360
FEATURE                Location/Qualifiers
source                 1..360
                       mol_type = other DNA
                       organism = synthetic construct
SEQUENCE: 58
gaggtgcagt tagtggagag cggaggcgat gtggtgcagc ccggtcgttc tttaagactg     60
agctgtgccg ccagcggctt caccttcagc agctacgcca tccactgggt gagacaagct    120
cccggtaaag gtttagagtg ggtggctgtg acttggcacg acggctccaa caagtactat    180
gccgagagct gatgggtcg tttcaccatc tctcgtgaca acagcaagaa cactttatat    240
ttacacatga actctttaag ggccgaggac accggcgtgt actactgcgc cagagccaag    300
ttcggcgagc cccagtactt ccagcactgg ggccaaggta caaccgtgac cgtgtccagc    360

SEQ ID NO: 59          moltype = DNA   length = 1347
FEATURE                Location/Qualifiers
source                 1..1347
                       mol_type = other DNA
                       organism = synthetic construct
SEQUENCE: 59
gaggtgcagt tagtggagag cggaggcgat gtggtgcagc ccggtcgttc tttaagactg     60
agctgtgccg ccagcggctt caccttcagc agctacgcca tccactgggt gagacaagct    120
cccggtaaag gtttagagtg ggtggctgtg acttggcacg acggctccaa caagtactat    180
gccgagagct gatgggtcg tttcaccatc tctcgtgaca acagcaagaa cactttatat    240
ttacacatga actctttaag ggccgaggac accggcgtgt actactgcgc cagagccaag    300
ttcggcgagc cccagtactt ccagcactgg ggccaaggta caaccgtgac cgtgtccagc    360
gctagcacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtataccc tgcccccatc ccgggaggag   1080
atgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctat agcaagctca ccgtggacaa gagcaggtgg   1260
cagcagggga acgtcttctc atgctccgtg atgcatgagg ctctgcacaa ccactacacg   1320
cagaagagcc tctccctgtc cccgggt                                       1347

SEQ ID NO: 60          moltype = DNA   length = 15
FEATURE                Location/Qualifiers
source                 1..15
                       mol_type = other DNA
                       organism = synthetic construct
SEQUENCE: 60
agctacgcca tccac                                                      15

SEQ ID NO: 61          moltype = DNA   length = 51
FEATURE                Location/Qualifiers
source                 1..51
                       mol_type = other DNA
                       organism = synthetic construct
SEQUENCE: 61
gtgacttggc acgacggctc caacaagtac tatgccgaga gcgtgatggg t              51

SEQ ID NO: 62          moltype = DNA   length = 33
```

```
FEATURE            Location/Qualifiers
source             1..33
                   mol_type = other DNA
                   organism = synthetic construct
SEQUENCE: 62
gccaagttcg gcgagcccca gtacttccag cac                                    33

SEQ ID NO: 63      moltype = DNA   length = 321
FEATURE            Location/Qualifiers
source             1..321
                   mol_type = other DNA
                   organism = synthetic construct
SEQUENCE: 63
gacatcgtga tgacccagag ccccagcttt ctgagcgcca gcgtgggcga tcgtgtgacc        60
atcacttgtc gtgccagcca aggtatcagc agctatttag cttggtacca gcagaagccc       120
ggcaaggccc ccaagctgct gatctacgcc gccagcactt tacagagcgg cgtgccttct       180
cgttttttctg gcagcggctc tggcaccgag ttcactttaa ccatcagctc tttacagccc      240
gaggacttcg ccacctatta ctgccagcag ctgaactcct acccttggac cttcggccaa       300
ggtaccaagg tggacatcaa g                                                 321

SEQ ID NO: 64      moltype = DNA   length = 32
FEATURE            Location/Qualifiers
source             1..32
                   mol_type = other DNA
                   organism = synthetic construct
SEQUENCE: 64
cgtgccagcc aaggtatcag cagctattta gc                                     32

SEQ ID NO: 65      moltype = DNA   length = 21
FEATURE            Location/Qualifiers
source             1..21
                   mol_type = other DNA
                   organism = synthetic construct
SEQUENCE: 65
gccgccagca ctttacagag c                                                 21

SEQ ID NO: 66      moltype = DNA   length = 27
FEATURE            Location/Qualifiers
source             1..27
                   mol_type = other DNA
                   organism = synthetic construct
SEQUENCE: 66
cagcagctga actcctaccc ttggacc                                           27

SEQ ID NO: 67      moltype = DNA   length = 321
FEATURE            Location/Qualifiers
source             1..321
                   mol_type = other DNA
                   organism = synthetic construct
SEQUENCE: 67
gacatcgtga tgacccagag ccctagcttt ttaagcgcca gcgtgggcga cagagtgacc        60
atcacttgtc gtgccagcca aggtatcaac aactatttag cttggtacca gcagaagccc       120
ggtatcgccc ccaagctgct gatctacgcc gccagcacac tgcagagcgg cgtgcctagc       180
agatttggtg gcagcggctc tggcacagag ttcactttaa ccatcagctc tttacagccc       240
gaggacttcg ccacctacta ctgccagcag ctgaagagct accccttcac cttcggcccc       300
ggcaccaagg tggagatcaa g                                                 321

SEQ ID NO: 68      moltype = DNA   length = 33
FEATURE            Location/Qualifiers
source             1..33
                   mol_type = other DNA
                   organism = synthetic construct
SEQUENCE: 68
cgtgccagcc aaggtatcaa caactattta gct                                    33

SEQ ID NO: 69      moltype = DNA   length = 21
FEATURE            Location/Qualifiers
source             1..21
                   mol_type = other DNA
                   organism = synthetic construct
SEQUENCE: 69
gccgccagca cactgcagag c                                                 21

SEQ ID NO: 70      moltype = DNA   length = 27
FEATURE            Location/Qualifiers
source             1..27
                   mol_type = other DNA
                   organism = synthetic construct
SEQUENCE: 70
```

```
cagcagctga agagctaccc cttcacc                                          27

SEQ ID NO: 71              moltype = DNA  length = 321
FEATURE                    Location/Qualifiers
source                     1..321
                           mol_type = other DNA
                           organism = synthetic construct
SEQUENCE: 71
gacatcgtga tgacccagag ccctagcttt ttaagcgcca gcgtgggcga cagagtgacc      60
atcacttgtc gtgccagcca aggtatcagc agctatttag cttggtacca gcagaagccc     120
ggcaaggccc ccaagctgct gatctacgcc gccagcactt tacagagcgg agtgcctagc     180
agattcagcg gcagcggctc cggcaccgag ttcactttaa ccatcagctc tttacagccc     240
gaggacttcg ccacctacta ctgccagcag ctgaacagct accccttcac cttcggcccc     300
ggcaccaagg tggacatcaa g                                               321

SEQ ID NO: 72              moltype = DNA  length = 27
FEATURE                    Location/Qualifiers
source                     1..27
                           mol_type = other DNA
                           organism = synthetic construct
SEQUENCE: 72
cagcagctga acagctaccc cttcacc                                          27

SEQ ID NO: 73              moltype = AA  length = 214
FEATURE                    Location/Qualifiers
source                     1..214
                           mol_type = protein
                           organism = synthetic construct
SEQUENCE: 73
DIVMTQSPSF LSASVGDRVT ITCRASQGIS SYLAWYQQKP GKAPKLLIYA ASTLQSGVPS      60
RFSGSGSGTE FTLTISSLQP EDFATYYCQQ LNSYPWTFGQ GTKVDIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 74              moltype = AA  length = 214
FEATURE                    Location/Qualifiers
source                     1..214
                           mol_type = protein
                           organism = synthetic construct
SEQUENCE: 74
DIVMTQSPSF LSASVGDRVT ITCRASQGIN NYLAWYQQKP GIAPKLLIYA ASTLQSGVPS      60
RFGGSGSGTE FTLTISSLQP EDFATYYCQQ LKSYPFTFGP GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 75              moltype = AA  length = 214
FEATURE                    Location/Qualifiers
source                     1..214
                           mol_type = protein
                           organism = synthetic construct
SEQUENCE: 75
DIVMTQSPSF LSASVGDRVT ITCRASQGIS SYLAWYQQKP GKAPKLLIYA ASTLQSGVPS      60
RFSGSGSGTE FTLTISSLQP EDFATYYCQQ LNSYPFTFGP GTKVDIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 76              moltype = DNA  length = 642
FEATURE                    Location/Qualifiers
source                     1..642
                           mol_type = other DNA
                           organism = synthetic construct
SEQUENCE: 76
gacatcgtga tgacccagag ccccagcttt ctgagcgcca gcgtgggcga tcgtgtgacc      60
atcacttgtc gtgccagcca aggtatcagc agctatttag cttggtacca gcagaagccc     120
ggcaaggccc ccaagctgct gatctacgcc gccagcactt tacagagcgg cgtgccttct     180
cgttttctg gcagcggctc tggcaccgag ttcactttaa ccatcagctc tttacagccc     240
gaggacttcg ccacctatta ctgccagcag ctgaactcct acccttggac cttcggccaa     300
ggtaccaagg tggacatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

SEQ ID NO: 77              moltype = DNA  length = 642
FEATURE                    Location/Qualifiers
source                     1..642
                           mol_type = other DNA
                           organism = synthetic construct
```

```
SEQUENCE: 77
gacatcgtga tgacccagag ccctagcttt ttaagcgcca gcgtgggcga cagagtgacc   60
atcacttgtc gtgccagcca aggtatcaac aactatttag cttggtacca gcagaagccc  120
ggtatcgccc ccaagctgct gatctacgcc gccagcacac tgcagagcgg cgtgcctagc  180
agatttggtg gcagcggctc tggcacagag ttcactttaa ccatcagctc tttacagcct  240
gaggacttcg ccacctacta ctgccagcag ctgaagagct acccttcac cttcggcccc   300
ggcaccaagg tggagatcaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 78              moltype = DNA   length = 642
FEATURE                    Location/Qualifiers
source                     1..642
                           mol_type = other DNA
                           organism = synthetic construct
SEQUENCE: 78
gacatcgtga tgacccagag ccctagcttt ttaagcgcca gcgtgggcga cagagtgacc   60
atcacttgtc gtgccagcca aggtatcagc agctatttag cttggtacca gcagaagccc  120
ggcaaggccc ccaagctgct gatctacgcc gccagcactt tacagagcgg agtgcctagc  180
agattcagcg gcagcggctc cggcaccgag ttcactttaa ccatcagctc tttacagccc  240
gaggacttcg ccacctacta ctgccagcag ctgaacagct accccttcac cttcggcccc  300
ggcaccaagg tggacatcaa gcgtacggtg gctgcaccat ctgtcttcat cttcccgcca  360
tctgatgagc agttgaaatc tggaactgcc tctgttgtgt gcctgctgaa taacttctat  420
cccagagagg ccaaagtaca gtggaaggtg gataacgccc tccaatcggg taactcccag  480
gagagtgtca cagagcagga cagcaaggac agcacctaca gcctcagcag caccctgacg  540
ctgagcaaag cagactacga gaaacacaaa gtctacgcct gcgaagtcac ccatcagggc  600
ctgagctcgc ccgtcacaaa gagcttcaac aggggagagt gt                     642

SEQ ID NO: 79              moltype = AA   length = 11
FEATURE                    Location/Qualifiers
source                     1..11
                           mol_type = protein
                           organism = synthetic construct
SEQUENCE: 79
RASQGIXXYL A                                                        11

SEQ ID NO: 80              moltype = AA   length = 9
FEATURE                    Location/Qualifiers
source                     1..9
                           mol_type = protein
                           organism = synthetic construct
SEQUENCE: 80
QQLXSYPXT                                                           9

SEQ ID NO: 81              moltype = DNA   length = 45
FEATURE                    Location/Qualifiers
source                     1..45
                           mol_type = other DNA
                           organism = synthetic construct
SEQUENCE: 81
ggaggggcg gtagcggagg gggaggatct gggggtgggg gctcc                    45

SEQ ID NO: 82              moltype = DNA   length = 57
FEATURE                    Location/Qualifiers
source                     1..57
                           mol_type = other DNA
                           organism = synthetic construct
SEQUENCE: 82
gggggggggg ggagcggagg ggggggagt ggtgggggt caggagggg aggaagt         57

SEQ ID NO: 83              moltype = DNA   length = 72
FEATURE                    Location/Qualifiers
source                     1..72
                           mol_type = other DNA
                           organism = synthetic construct
SEQUENCE: 83
ggggagggg gatcaggagg cggtgggagc ggggaggtg gatccggtgg agggtcagga     60
ggtggagggt cc                                                        72

SEQ ID NO: 84              moltype = DNA   length = 87
FEATURE                    Location/Qualifiers
source                     1..87
                           mol_type = other DNA
                           organism = synthetic construct
SEQUENCE: 84
ggtggtggcg gcagcggcgg cggcggtagc ggtggcggcg gttctggagg aggaggcagc   60
```

```
ggtggaggaa gcggaggtgg aggctcc                                          87

SEQ ID NO: 85              moltype = AA   length = 242
FEATURE                    Location/Qualifiers
source                     1..242
                           mol_type = protein
                           organism = synthetic construct
SEQUENCE: 85
EVQLVESGGD VVQPGRSLRL SCAASGFTFS SYAIHWVRQA PGKGLEWVAV TWHDGSNKYY        60
AESVMGRFTI SRDNSKNTLY LHMNSLRAED TGVYYCARAK FGEPQYFQHW GQGTTVTVSS       120
GGGGSGGGGS GGGGSDIVMT QSPSFLSASV GDRVTITCRA SQGISSYLAW YQQKPGKAPK       180
LLIYAASTLQ SGVPSRFSGS GSGTEFTLTI SSLQPEDFAT YYCQQLNSYP FTFGPGTKVD       240
IK                                                                     242

SEQ ID NO: 86              moltype = AA   length = 242
FEATURE                    Location/Qualifiers
source                     1..242
                           mol_type = protein
                           organism = synthetic construct
SEQUENCE: 86
QITLRESGGD VVQPGRSLRL SCAASGFTFS SYAIHWVRQA PGKGLEWVAV TWHDGSNKYY        60
AESVMGRFTI SRDNSKNTLY LHMNSLRAED TGVYYCARAK FGEPQYFQHW GQGTLVTVSS       120
GGGGSGGGGS GGGGSDIVMT QSPSFLSASV GDRVTITCRA SQGINNYLAW YQQKPGIAPK       180
LLIYAASTLQ SGVPSRFGGS GSGTEFTLTI SSLQPEDFAT YYCQQLKSYP FTFGPGTKVE       240
IK                                                                     242

SEQ ID NO: 87              moltype = AA   length = 242
FEATURE                    Location/Qualifiers
source                     1..242
                           mol_type = protein
                           organism = synthetic construct
SEQUENCE: 87
QITLRESGGD VVQPGRSLRL SCAASGFTFS SYAIHWVRQA PGKGLEWVAV TWHDGSNKYY        60
AESVMGRFTI SRDNSKNTLY LHMNSLRAED TGVYYCARAK FGEPQYFQHW GQGTLVTVSS       120
GGGGSGGGGS GGGGSDIVMT QSPSFLSASV GDRVTITCRA SQGISSYLAW YQQKPGKAPK       180
LLIYAASTLQ SGVPSRFSGS GSGTEFTLTI SSLQPEDFAT YYCQQLNSYP WTFGQGTKVD       240
IK                                                                     242

SEQ ID NO: 88              moltype = AA   length = 120
FEATURE                    Location/Qualifiers
source                     1..120
                           mol_type = protein
                           organism = synthetic construct
SEQUENCE: 88
QITLRESGGD VVQPGRSLRL SCAASGFTFS SYAIHWVRQA PGKGLEWVAV TWHDGSNKYY        60
AESVMGRFTI SRDNSKNTLY LHMNSLRAED TGVYYCARAK FGEPQYFQHW GQGTLVTVSS       120

SEQ ID NO: 89              moltype = AA   length = 107
FEATURE                    Location/Qualifiers
source                     1..107
                           mol_type = protein
                           organism = synthetic construct
SEQUENCE: 89
DIVMTQSPSF LSASVGDRVT ITCRASQGIS SYLAWYQQKP GKAPKLLIYA ASTLQSGVPS        60
RFSGSGSGTE FTLTISSLQP EDFATYYCQQ LNSYPWTFGQ GTKVDIK                     107

SEQ ID NO: 90              moltype = AA   length = 107
FEATURE                    Location/Qualifiers
source                     1..107
                           mol_type = protein
                           organism = synthetic construct
SEQUENCE: 90
DIVMTQSPSF LSASVGDRVT ITCRASQGIN NYLAWYQQKP GIAPKLLIYA ASTLQSGVPS        60
RFGGSGSGTE FTLTISSLQP EDFATYYCQQ LKSYPFTFGP GTKVEIK                     107

SEQ ID NO: 91              moltype = AA   length = 120
FEATURE                    Location/Qualifiers
source                     1..120
                           mol_type = protein
                           organism = synthetic construct
SEQUENCE: 91
EVQLVESGGD VVQPGRSLRL SCAASGFTFS SYAIHWVRQA PGKGLEWVAV TWHDGSNKYY        60
AESVMGRFTI SRDNSKNTLY LHMNSLRAED TGVYYCARAK FGEPQYFQHW GQGTTVTVSS       120
```

```
SEQ ID NO: 92          moltype = AA  length = 107
FEATURE                Location/Qualifiers
source                 1..107
                       mol_type = protein
                       organism = synthetic construct
SEQUENCE: 92
DIVMTQSPSF LSASVGDRVT ITCRASQGIS SYLAWYQQKP GKAPKLLIYA ASTLQSGVPS  60
RFSGSGSGTE FTLTISSLQP EDFATYYCQQ LNSYPFTFGP GTKVDIK               107
```